United States Patent
Scott et al.

(10) Patent No.: US 10,919,844 B2
(45) Date of Patent: Feb. 16, 2021

(54) ANTIBACTERIALS AND/OR MODULATORS OF BIOFILM FORMATION AND METHODS OF USING THE SAME

(71) Applicant: Indiana University Research and Technology Corporation, Indianapolis, IN (US)

(72) Inventors: William L. Scott, Indianapolis, IN (US); Martin J. O'Donnell, Indianapolis, IN (US); Jack Geno Samaritoni, Avon, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/869,865

(22) Filed: Jan. 12, 2018

(65) Prior Publication Data

US 2018/0215704 A1 Aug. 2, 2018

Related U.S. Application Data

(62) Division of application No. 15/237,258, filed on Aug. 15, 2016, now abandoned.

(60) Provisional application No. 62/205,367, filed on Aug. 14, 2015.

(51) Int. Cl.

| | | |
|---|---|---|
| *C07C 237/20* | (2006.01) | |
| *C07C 229/34* | (2006.01) | |
| *C07D 213/40* | (2006.01) | |
| *C07D 295/13* | (2006.01) | |
| *C07D 211/32* | (2006.01) | |
| *C07D 207/08* | (2006.01) | |

(52) U.S. Cl.
CPC .......... *C07C 237/20* (2013.01); *C07C 229/34* (2013.01); *C07D 207/08* (2013.01); *C07D 211/32* (2013.01); *C07D 213/40* (2013.01); *C07D 295/13* (2013.01)

(58) Field of Classification Search
CPC ... C07C 237/20; C07C 229/34; C07D 213/40; C07D 295/13; C07D 211/32; C07D 207/08
See application file for complete search history.

(56) References Cited

U.S. PATENT DOCUMENTS

| 3,813,317 A | 5/1974 | Benoiton |
| 2017/0044097 A1 | 2/2017 | Scott |

FOREIGN PATENT DOCUMENTS

| WO | 97/19908 | | 6/1997 |
| WO | WO 2005/023368 | * | 3/2005 |
| WO | WO 2014/118779 | * | 8/2014 |
| WO | WO 2014/142748 | * | 9/2014 |

OTHER PUBLICATIONS

Fura, A. DDT, 2006, 11, pp. 133-142.*
Anari et al. DDT 2005, 10, pp. 711-717.*
Nedderman, A.N.R. Biopham, Drug Dispos., 2009, 30, pp. 152-162.*
Persson et al., Ther Umsch, Feb. 2008; 65(2): 121-6.*

* cited by examiner

*Primary Examiner* — Rebecca L Anderson
(74) *Attorney, Agent, or Firm* — Faegre Drinker Biddle & Reath LLP

(57) ABSTRACT

Amides substituted with aromatic groups were synthesized and some were purified to create enantiomer pure compounds. The compounds were tested to determine their ability to inhibit the growth of bacteria and the formation of biofilms created by bacteria. Some of these compounds were found to be effective antibacterials and to effectively inhibit the formation of biofilms.

14 Claims, 38 Drawing Sheets

ANTIBACTERIALS AND/OR MODULATORS OF BIOFILM FORMATION AND METHODS OF USING THE SAME

CROSS-REFERENCE TO RELATED APPLICATIONS

This application is a divisional of U.S. patent application Ser. No. 15/237,258, filed Aug. 15, 2016, which claims the benefit of U.S. Provisional Patent Application No. 62/205,367, filed Aug. 14, 2015, the entire disclosures of both of which are hereby expressly incorporated by reference herein.

STATEMENT OF GOVERNMENTAL RIGHTS

This invention was made with government support under GM028193 awarded by the National Institutes of Health and 1140602 awarded by the National Science Foundation. The government has certain rights in the invention.

FIELD OF THE INVENTION

This invention relates generally to compounds that can inhibit the growth of bacterial and/or inhibit or reduce the formation of biofilms formed by some types of bacteria and methods of using these compounds to treat bacterial infection and outbreaks and/or to reduce the formation of biofilms.

BACKGROUND AND SUMMARY

Bacterial infections may cause severe suffering and even death. While virtually all humans and animals are susceptible to bacterial infections certain sub-population are especially vulnerable to such infections. Vulnerable populations of human include the very young, the very old, persons with poorly developed or weakened immune systems or patients that already have underlying health challenges such as Cystic Fibrosis that make them susceptible to certain bacterial infections. Since the introduction of penicillin in the 1940s, antibiotics have served as one of the major treatments for pathogenic bacterial infections.

Unfortunately not all bacteria are susceptible to treatment with antibiotics. Classes of bacteria that are especially pathogenic include bacteria that readily form biofilms. Some of the uses of these biofilms in the pathogenic setting include helping to anchor bacteria to a portion of the body and to help the bacteria existing in conjunction with the biofilm to evade the body's immune system. Moreover, the widespread use of broad spectrum antibiotics has helped to give rise to antibiotic resistant strains of pathogenic bacteria which were once easily controlled with such compounds. Accordingly, there exists a need for compounds that have the ability to stop or at least slow the growth of pathogenic bacteria.

Biofilms are present everywhere, on man-made structures, in nature, and even in the mouth of an animal or a human. A biofilm is a community of bacteria which adhere to a solid surface and other bacteria. Biofilms allow bacteria to remain in a favorable niche, act as a defense, and allow bacterial cells to live in close association with each other (increasing genetic exchange).

The biofilm itself is composed of polysaccharides, proteins, various signaling molecules, and amino acids, all produced by the bacterial cells within. Bacteria begin forming the biofilms in the presence of valuable nutrient resources and begin to rapidly grow in size and population.

Biofilms form in three stages: attachment, colonization, and development. During attachment, a few cells adhere to a solid surface. Adhering to the solid surface causes the cell to express biofilm-specific genes. Next, the biofilm begins colonization. In this stage, intercellular communication is essential, along with bacterial multiplication and polysaccharide secretion. Lastly, the biofilm matures into a large structure with numerous bacteria encased in a matrix of polysaccharide, DNA, and protein. Biofilms can trap nutrients for the microbial population and prevent detachment of the population in flowing systems, such as the saliva running across your teeth or water flowing down a stream. As the biofilm ages, and nutrients become depleted, dispersal of the bacterial cells within the biofilm allows them to spread to other resource rich areas.

Although many biofilms are relatively harmless, some can be very malicious and cause serious illnesses. They have been associated with urinary tract infections, ear infections, and colonization of implanted medical devices. For example, one culprit which produces biofilms is *Pseudomonas aeruginosa* (PA). PA is particularly dangerous to those suffering from cystic fibrosis. Cystic fibrosis is a recessively inherited genetic disease caused by a mutation in the gene which codes for the protein cystic fibrosis transmembrane conductance regulator (CFTR). The malfunction of CFTR leads to increased mucus accumulation in the lungs and other organs, which is an ideal medium for *P. aeruginosa* and other bacteria to colonize into biofilms.

The study of biofilms has afforded a new strategy in combating virulent bacteria, such as *P. aeruginosa*. Instead of formulating drugs to kill harmful bacteria, biofilms can be treated with drugs which signal the bacteria to leave the biofilm and disperse or reduce biofilm formation. Causing the bacteria to disperse comes with the benefit of reducing them to a benign and defenseless state, allowing the body's own immune system to destroy the invaders without side effects from drugs and without inducing antibiotic resistance in the bacteria. Accordingly, the ability of a drug to inhibit or reduce formation of biofilms of bacteria provides an excellent indication that the drug will likely inhibit or reduce the growth of the bacteria.

For more information about biofilm composition and development, see Flemming, H. C. et al., The Biofilm Matrix. NATURE REVIEWS MICROBIOLOGY 2010, 8, 623-633, Hall-Stoodley, L. et al., Bacterial Biofilms: From the Natural Environment to Infectious Diseases. NATURE REVIEWS MICROBIOLOGY 2004, 2, 95-108; Kolodkin-Gal, I. et al., D-Amino Acids Trigger Biofilm Disassembly. SCIENCE 2010 328, 627-629, disclosures of which are incorporated by reference in its entirety to the extent that they are not inconsistent with the explicit teachings of this specification.

Aspects of the instant invention include compounds that inhibit or reduce the growth of bacteria including certain pathogenic bacteria some of these compounds also reduce or inhibit the development of biofilms that may contribute to the pathology of certain strains of bacteria. These compounds include amide derivatives of fluorinated phenyl groups, in some instances specific enantiomers of such compounds are especially effective anti-bacterial agents. One such compound is an amide derivative of 4-fluorophenylalanine; this and related compounds exhibit the ability stop or at least slow the growth of *Pseudomonas aeruginosa*, a pathogen known to be responsible for severe bacterial infection in patient who has Cystic Fibrosis.

Some aspects of the invention include methods of synthesizing such compounds and using the same to treat bacterial infections and to eliminate or at least reduce the formation of biofilms associated with the growth of certain types of bacteria.

A first embodiments of the present disclosure includes at least one compound of the following Formula or a pharmaceutically acceptable salt thereof, or a metabolite thereof:

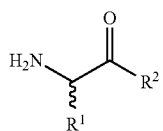

wherein $R^1$ is selected from the group consisting of: biphenyl, —$(CH_2)_n$-biphenyl, biphenyl ketone, naphthalene, anthracene, benzyl, benzyl substituted with 1 to 3 halogens, $C_1$-$C_6$ alkyl, $C_1$-$C_6$ alkoxy, —$NH_2$, —$NO_2$, —CN, or —$CF_3$, phenyl, and phenyl substituted with 1 to 3 halogens, $C_1$-$C_6$ alkyl, $C_1$-$C_6$ alkoxy, —$NH_2$, —$NO_2$, —CN, or —$CF_3$;

$R^2$ is selected from the group consisting of: —OH, —$NH_2$, —$NHR^3$, and —$NR^3R^4$;

$R^3$ and $R^4$ are independently selected from the group consisting of: H, halogen, —$NH_2$, —$NO_2$, $C_1$-$C_6$ alkyl being unbranched, branched or cyclic, $C_1$-$C_6$ alkoxy, $C_1$-$C_6$ haloalkoxy, hydroxyl, acyl, acyl amides, carboxyl, tetrazolyl, and —$(CH_2)_n$—$R^5$;

Alternatively, $R^3$ and $R^4$ are taken together to form a pyridine, a piperidine, a pyrrolidine, or a pyrrole ring;

$R^5$ is —OH, —$CF_3$, morpholinyl, pyridinyl, benzyl, benzyl substituted with 1 to 3 halogens, $C_1$-$C_6$ alkyl, $C_1$-$C_6$ alkoxy, —$NH_2$, —$NO_2$, —CN, or —$CF_3$, phenyl, or phenyl optionally substituted with 1 to 3 halogen, $C_1$-$C_6$ alkyl, $C_1$-$C_6$ alkoxy, —OH, —$NH_2$, —$NO_2$, —CN, or —$CF_3$; and n is 1, 2, 3, or 4.

A second embodiment includes the compound of the first embodiment, wherein: $R^1$ is benzyl substituted with 1 to 3 halogens, —$NH_2$, —$NO_2$, —CN, or —$CF_3$; and $R^2$ is —OH or —$NH_2$; or a pharmaceutically acceptable salt thereof, or a metabolite thereof.

A third embodiment includes the compound of the first and the second embodiments, wherein: $R^1$ is benzyl substituted with 1 to 3 halogens, —$NH_2$, —$NO_2$, —CN, or —$CF_3$; $R^2$ is —$NHR^3$; $R^3$ is —$(CH_2)_n$—$R^5$; $R^5$ is —OH, —$CF_3$, morpholinyl, pyridinyl, or benzyl optionally substituted with 1 to 3 halogen, $C_1$-$C_6$ alkyl, $C_1$-$C_6$ alkoxy, —OH, —$NH_2$, —$NO_2$, —CN, or —$CF_3$; and n is 1, 2, 3, or 4; or a pharmaceutically acceptable salt thereof, or a metabolite thereof.

A fourth embodiment includes the compound of any of the first to the third embodiments, wherein the compound is at least one enantiomer of at least one compound selected from the group consisting of:

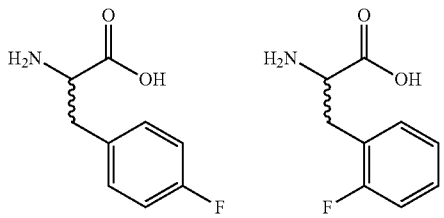

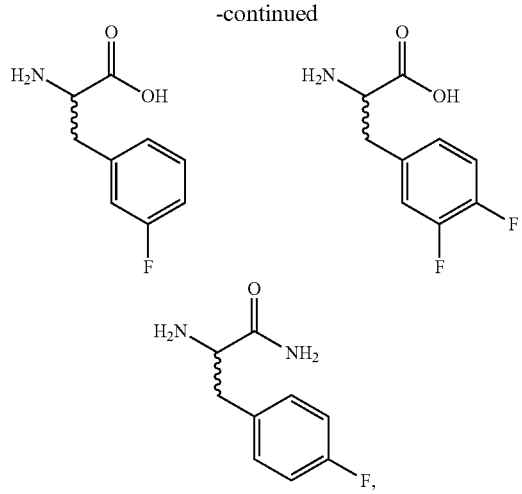

or a pharmaceutically acceptable salt thereof, or a metabolite thereof.

A fifth embodiment includes the compound of any of the first to the third embodiments, wherein the compound is selected from the group consisting of:

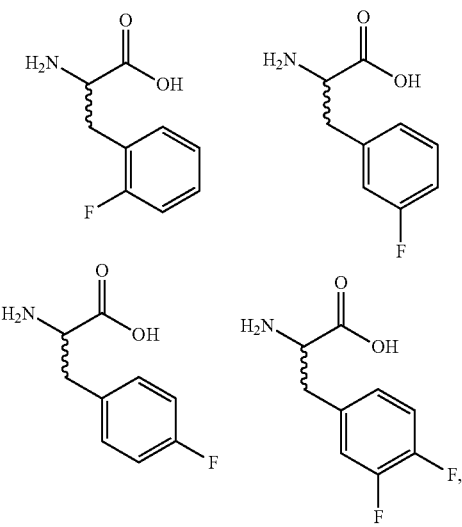

or a pharmaceutically acceptable salt thereof, or a metabolite thereof.

A sixth embodiment includes the compound of any of the first to the third embodiments, wherein the compound is selected from the group consisting of:

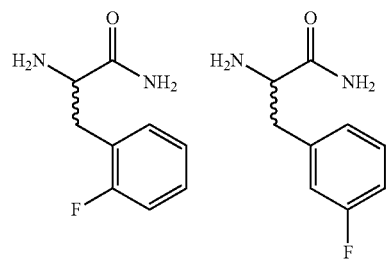

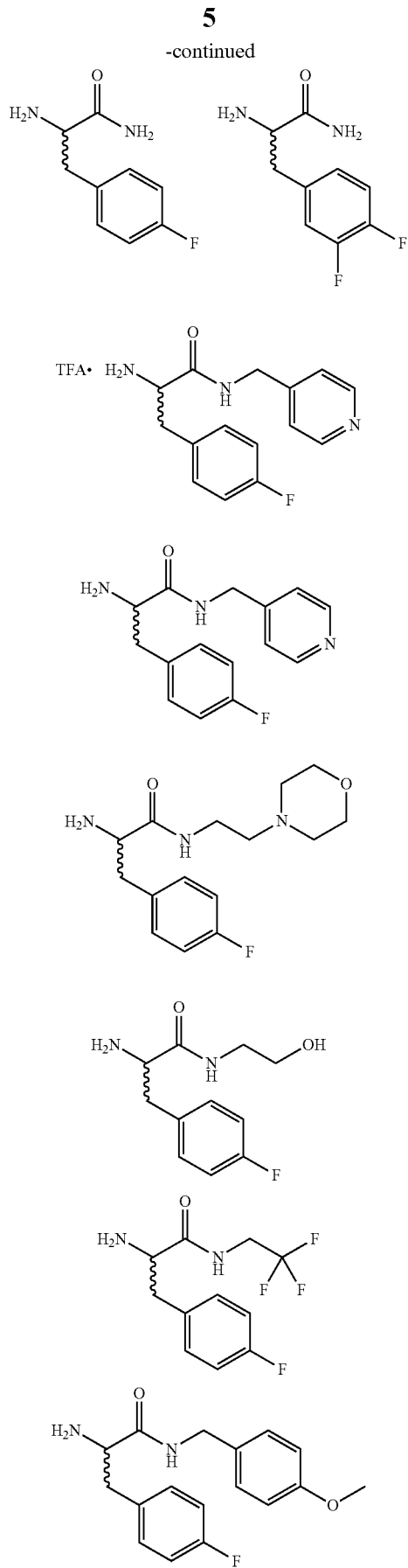

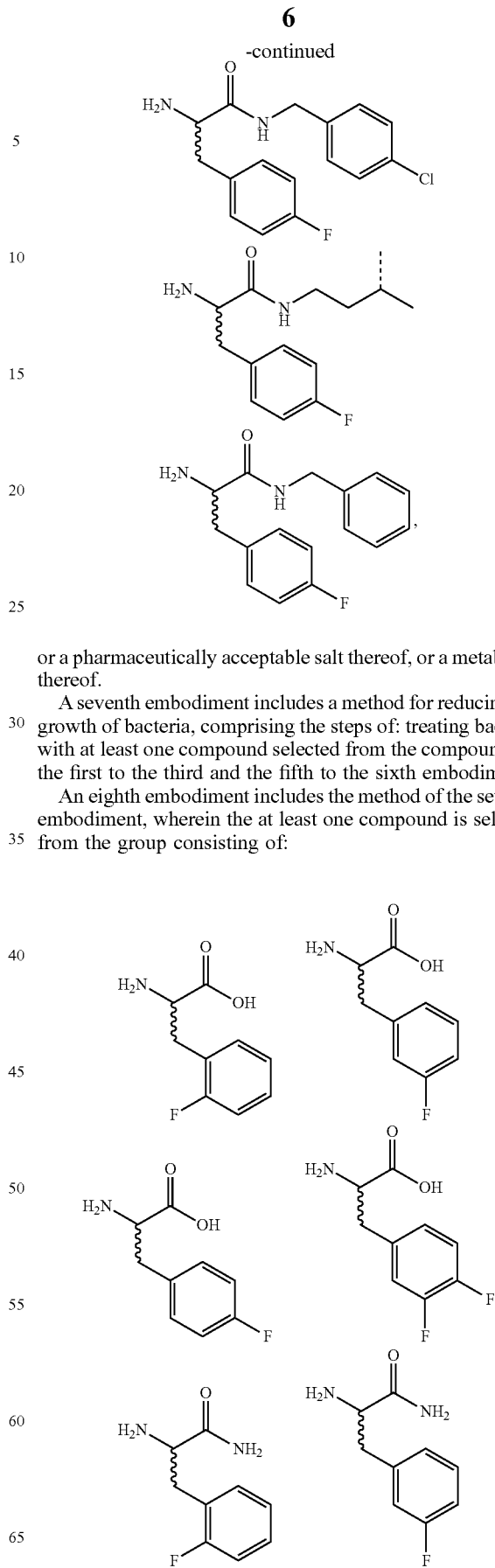

or a pharmaceutically acceptable salt thereof, or a metabolite thereof.

A seventh embodiment includes a method for reducing the growth of bacteria, comprising the steps of: treating bacteria with at least one compound selected from the compounds of the first to the third and the fifth to the sixth embodiments.

An eighth embodiment includes the method of the seventh embodiment, wherein the at least one compound is selected from the group consisting of:

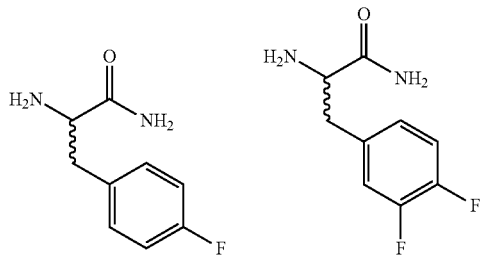
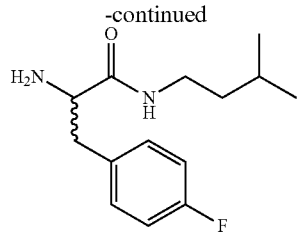

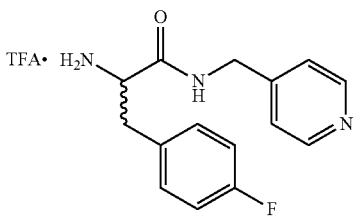

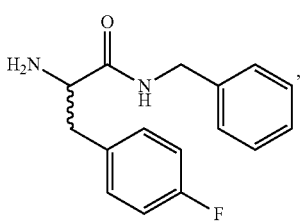

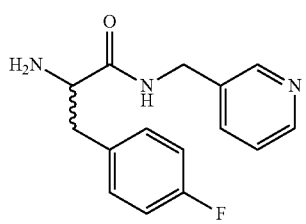

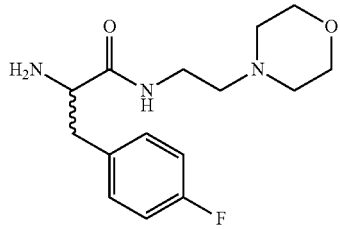

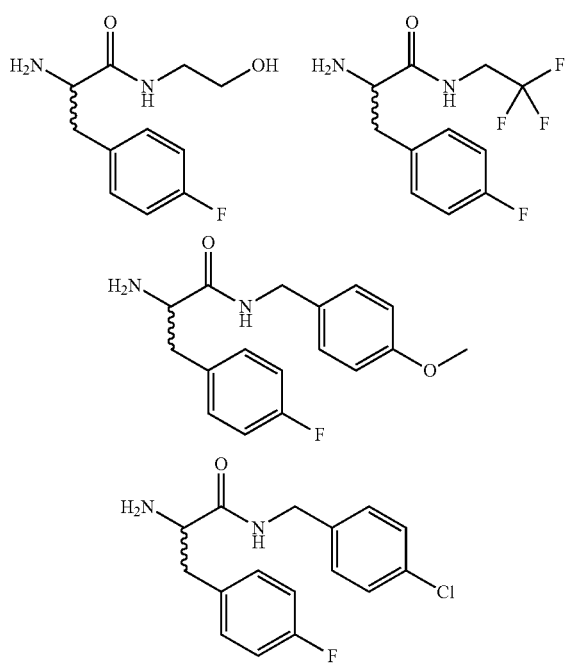

or a pharmaceutically acceptable salt thereof, or a metabolite thereof.

A ninth embodiment includes at least one method according to any of the seventh and the eighth embodiments, wherein the bacteria are gram-negative bacteria.

A tenth embodiment includes at least one method according to any of the seventh to the ninth embodiments, wherein the bacteria is *Pseudomonas aeruginosa*.

An eleventh embodiment includes at least one method according to any of the seventh to the tenth embodiments, further comprising the step of: reducing biofilm formation of the bacteria.

A twelfth embodiment includes at least one method according to any of the seventh to the eleventh embodiments, further comprising the step of: treating an area that has been infected by the bacteria.

A thirteenth embodiment includes at least one method according to the twelfth embodiment, wherein the area comprises wet or dry wet or dry surfaces including the skin, hair or fur of animals and/or humans, or the outside of seeds or plants including leaves, stems, shoots, roots, branches, blooms, fruits and the like, or any inanimate object surfaces.

A fourteenth embodiment includes a method of treating bacterial infections, comprising the steps of: providing at least one therapeutically effective dose of at least one compound selected from the compounds of the first to the third and/or the compounds of the fifth to the sixth embodiments to a patient.

A fifteenth embodiment includes the method according to the fourteenth embodiment, further comprising the step of: diagnosing a patient with bacterial infections, wherein the bacterial infections are caused by gram-negative bacteria.

A sixteenth embodiment includes the method according to the fifteenth embodiment, wherein the gram-negative bacteria is *Pseudomonas aeruginosa*.

A seventeenth embodiment includes at least one method according to any one of the fourteenth to the sixteenth embodiments, wherein the at least one compound is selected from the group consisting of:

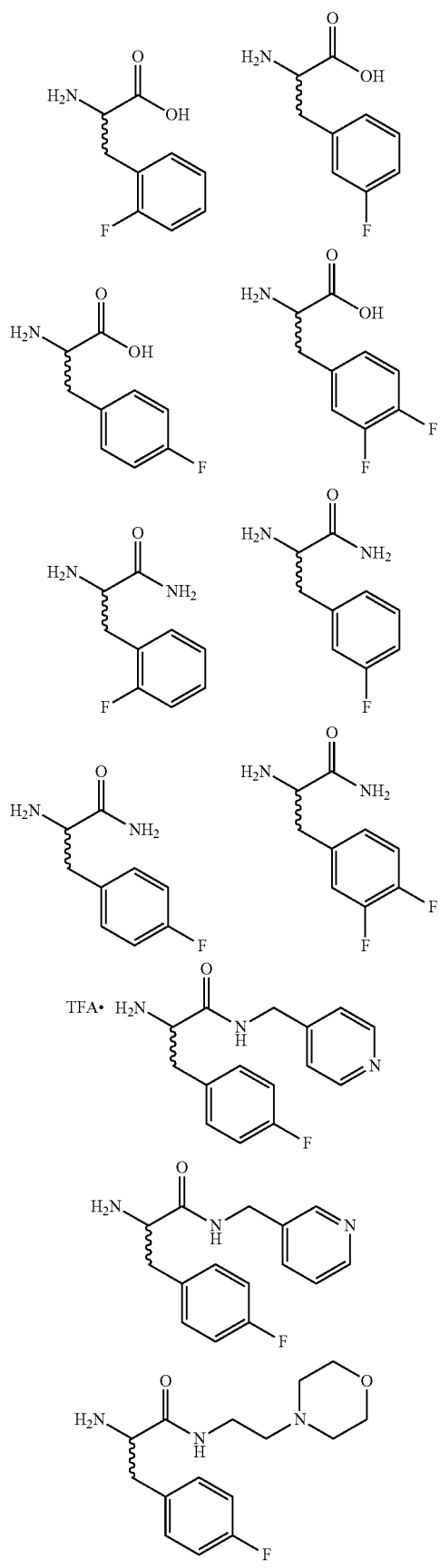
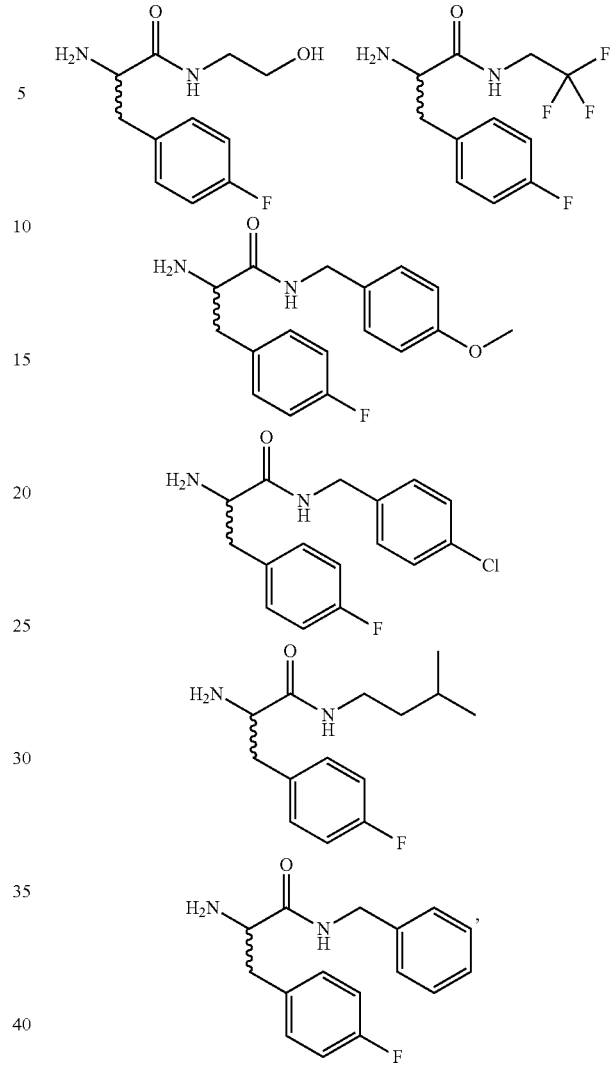

or a pharmaceutically acceptable salt thereof, or a metabolite thereof.

An eighteenth embodiment includes at least one method according to any one of the fourteenth to the seventeenth embodiments, wherein the therapeutically effective dose of the compound selected from the compounds of claim 1 is on the order of between about 1 mg/kg to about 7 mg/kg and the dose of the compound is administered to the patient at least once per day.

A nineteenth embodiment includes the eighteenth embodiment, wherein the therapeutically effective dose of the compound selected from the compounds of claim 1 is on the order of between about 3 mg/kg to about 5 mg/kg and the dose of the compound is administered to the patient at least once per day.

A twentieth embodiment includes at least one method according to any one of the fourteenth to the nineteenth embodiments, wherein the therapeutically effective dose of the compound selected from the compounds of the first to the third and/or the compounds of the fifth to the sixth embodiments is administered by intravenous or intramuscular injections.

DESCRIPTION

Figure 1:
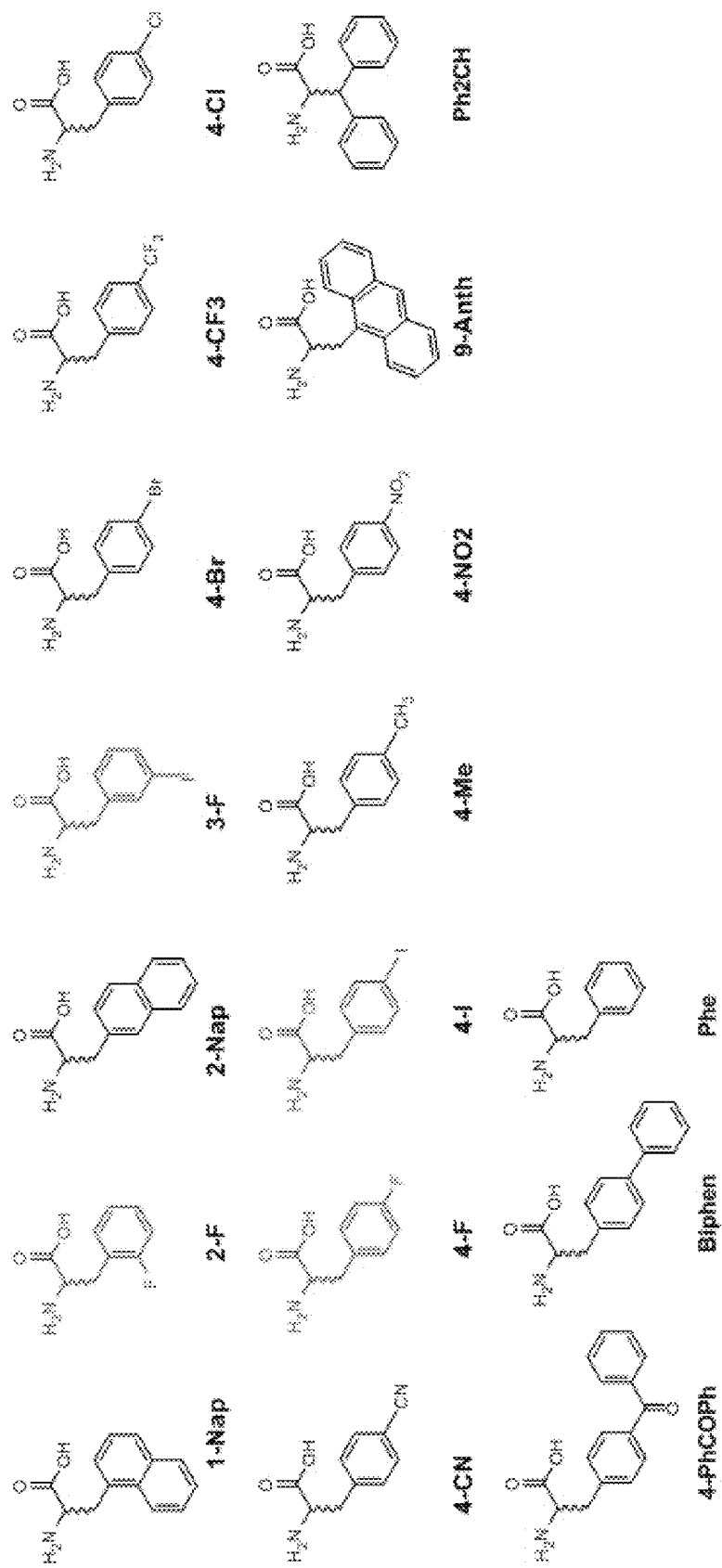
FIG. 1. Various compounds and their corresponding chemical structures.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

As used herein, unless explicitly stated otherwise or clearly implied otherwise the term 'about' refers to a range of values plus or minus 10 percent, e.g. about 1.0 encompasses values from 0.9 to 1.1.

As used herein, unless explicitly stated otherwise or clearly implied otherwise the meaning of the terms "treatment" or "treating" used in conjunction with various compounds and methods disclosed and claimed herein include, but are not limited to, applying certain compounds to various either wet or dry surfaces including, but not limited to the skin, hair or fur of animals or the outside of seeds or plants including leaves, stems, shoots, roots, branches, blooms, fruits and the like, or any inanimate object either directly or indirectly. The terms "treatment" or "treating" also includes adding compounds to liquids, either aqueous or non-aqueous or mixtures thereof including simple mixtures of such or emulsions. The terms "treatment" or "treating" used in also include administering compounds to plants, cells, animals and humans. The terms "treatment" or "treating" include but are not limited to contacting bacteria or the biofilms of bacteria, directly or indirectly and may affect the growth of bacteria, and either directly or indirectly the formation of bacteria biofilms. The terms "treatment" or "treating" as used herein may include administering a 'therapeutically effective dose or doses of compounds.

As used herein, unless explicitly stated otherwise or clearly implied otherwise the terms 'therapeutically effective dose,' 'therapeutically effective amounts,' and the like, refers to a portion of a compound that has a net positive effect on the health and wellbeing of a human or other animal. Therapeutic effects may include an improvement in longevity, quality of life and the like these effects also may also include a reduced susceptibility to developing disease or deteriorating health or well being. The effects may be immediately realized after a single dose and/or treatment or they may be cumulatively realized after a series of doses and/or treatments.

Pharmaceutically acceptable salts include salts of compounds of the invention that are safe and effective for use in mammals and that possess a desired therapeutic activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, trifluoroacetic acid, and pamoate (i.e., 1,1'-methylene-bis-(2-hydroxy-3-naphthoate)) salts. Certain compounds of the invention may form pharmaceutically acceptable salts with various amino acids. Suitable base salts include, but are not limited to, aluminum, calcium, lithium, magnesium, potassium, sodium, zinc, and diethanolamine salts. For addition information on some pharmaceutically acceptable salts that can be used to practice the invention please reviews such as Berge, et al., 66 J. PHARM. SCI. 1-19 (1977), and Haynes, et al, J. Pharma. Sci., Vol. 94, No. 10, October 2005, pgs. 2111-2120.

Bacteria are known to communicate via small molecules. Through this communication they are able to create complex, highly-organized communities responsible for biofilm formation, antibiotic resistance, and other important processes. These biofilms are involved in many disease states, including cystic fibrosis, which is a genetically inherited disease affecting approximately 70,000 people worldwide. Dr. Richard Losick and colleagues at Harvard have reported that certain D-amino acids (1, $R^1$=naturally occurring amino acid side chains in the D configuration) are a trigger for the disassembly of bacterial biofilms (*Science*, 2010, 328, 627-629). D-Tyrosine was reported to be particularly active:

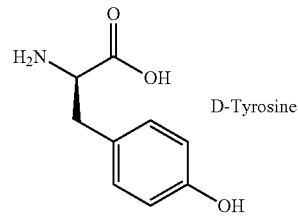 [SMILES: N[C@H](Cc1ccc(O)cc1)C(=O)O]

Using the synthetic procedure discussed herein compounds such as 1 and 2 were

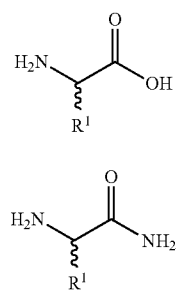

wherein $R^1$ is selected from the group consisting of a benzyl group optionally substituted with a halogen, methyl group, or a nitro group, a bi-phenyl, a naphthalene, and an anthracene.

Experiments and Results

Scheme 1: Synthesis of unnatural amino acids 1 using synthesis procedure D3-6.

One aspect of this approach uses D3-6 (Scheme 1) developed for our Distributed Drug Discovery (D3) project to synthesize analogs of compound 1. This approach employs solid-phase chemistry, Bill-Board equipment, and alkylating agents R¹X to synthesize a small "library" of unnatural amino acids 1.

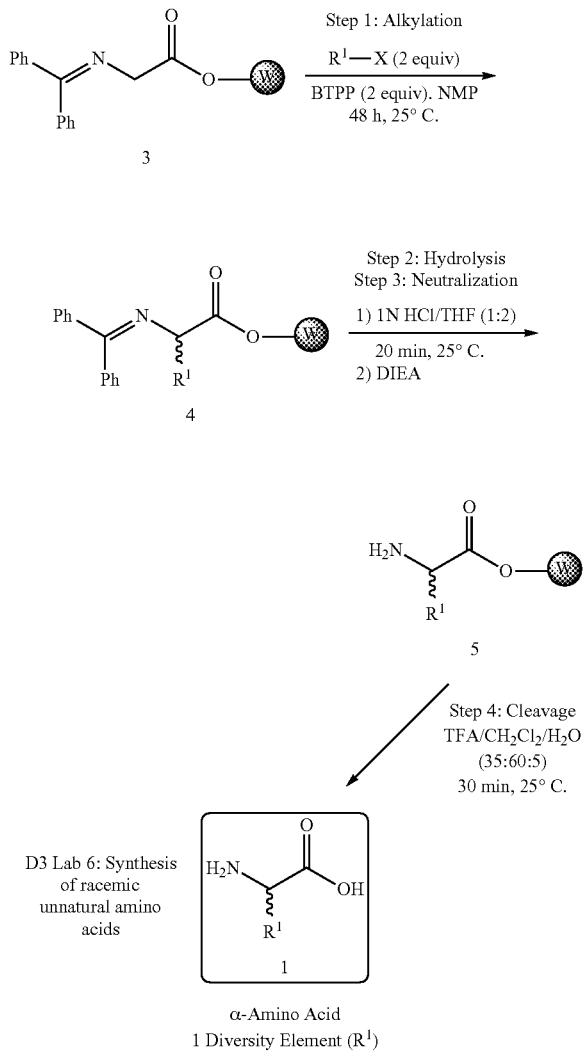

α-Amino Acid
1 Diversity Element (R¹)

A straightforward biological assay was developed to provide for the study these important bacterial biofilm communities. This assay also provided an efficient means for screening for compounds that have an effect on bacterial growth and/or biofilm formation.

The racemic amino acid derivatives 1 (synthesized in row A of each Bill-Board) are then screened for biological activity (antibacterial activity in a Kirby-Bauer disc plate assay) and/or K357 laboratory (assay for biofilm formation by *Pseudomonas aeruginosa*).

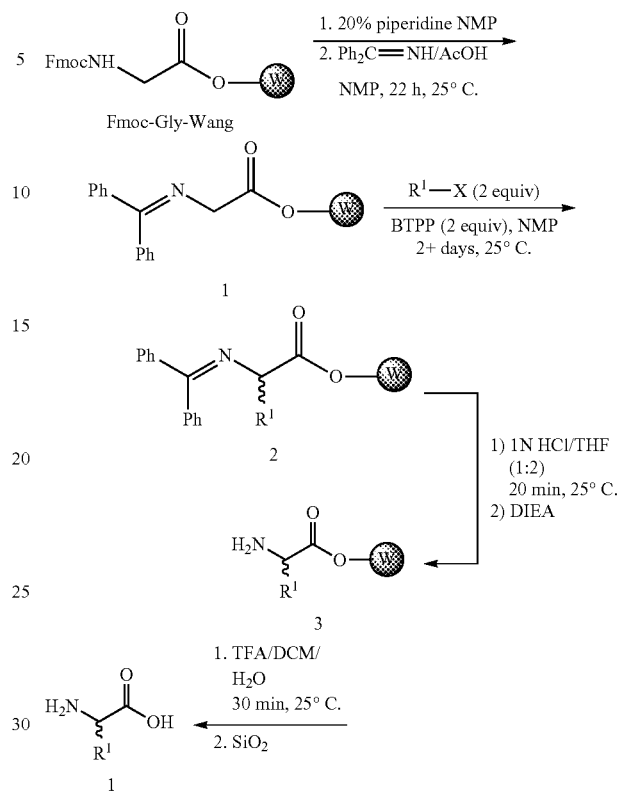

Scheme 2: Preparation of Amino Acids 4.

Fmoc-Gly-Wang resin (15.725 g, 12.108 mmol) was swelled for 30 minutes with 100 mL of NMP in a 250-mL solid-phase peptide synthesis vessel. The vessel was drained and the resin was treated with 70 mL of 20% piperidine in NMP for 2 minutes. The vessel was drained and the resin was treated with 120 mL of 20% piperidine and was rocked for 45 minutes on an orbital shaker. The vessel was drained, the resin was washed with 6×75 mL×2 min NMP. The deprotected resin was then treated with 20.32 mL of benzophenone imine in 110 mL of NMP followed by 6.02 mL of acetic acid. The vessel was rocked overnight at room temperature. After 22 h the vessel was drained and the resin was washed with 4×75 mL×2 min NMP and dichloromethane each. The resin 1 was dried under a slow stream of dry nitrogen gas for approximately 30 h and was then stored at 2° C.

50 μmols of resin 1 was treated with 100 μmols of 0.20 M BTPP in NMP followed by 100 μmols of 0.20 M fluorinated benzyl bromide R¹X in NMP. After two days the reaction mixture was filtered and the resulting resin 2 was washed once with 3 mL of THF. To the resin was then added 2.5 mL of 1.0 N HCl in THF (1:2). After 20 minutes the resin was filtered and was washed with 3 mL of THF followed by 2×2.5 mL of 0.20 M diisopropylethylamine in NMP, 2×2.5 mL of NMP, 3×2 mL of THF and 3×3 mL of dichloromethane to give resin 3. Treatment of resin 3 with 2 mL of 35:60:5 TFA/DCM/H₂O for 30 minutes was followed by filtering and washing the resin with 2 mL of 35:60:5 TFA/DCM/H₂O and 2 mL of DCM. The combined filtrates were evaporated to a residue which was chromatographed on silica gel using iPrOH/MeOH/NH₄OH mobile phases to elute the free bases 4.

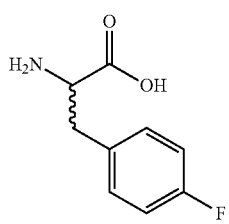 [SMILES: NC(Cc1ccc(F)cc1)C(=O)O]

2-Amino-3-(4-fluorophenyl)propanoic acid (4a)

6.9 mg (75%), ¹HNMR (D$_2$O) δ 3.04 (dd, 1H, J=14.7 and 7.8 Hz), 3.18 (dd, 1H, J=14.6 and 5.3 Hz), 3.89 (dd, 1H, J=7.8 and 5.3 Hz), 7.06 (t, 2H, J=8.9 Hz), 7.21 (m, 2H).

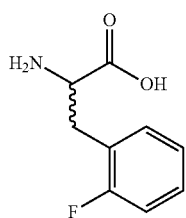 [SMILES: NC(Cc1ccccc1F)C(=O)O]

2-Amino-3-(2-fluorophenyl)propanoic acid (4b)

9.1 mg (99%), ¹HNMR (D$_2$O) δ 3.08 (dd, 1H, J=14.6 and 7.9 Hz), 3.30 (dd, 1H, J=14.6 and 5.4 Hz), 3.94 (t, 1H, J=6.6 Hz), 7.11-7.17 (m, 2H), 7.26-7.36 (m, 2H).

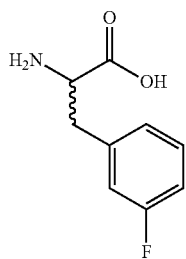 [SMILES: NC(Cc1cccc(F)c1)C(=O)O]

2-Amino-3-(3-fluorophenyl)propanoic acid (4c)

7.5 mg (82%), ¹HNMR (D$_2$O) δ 3.03 (dd, 1H, J=14.5 and 7.9 Hz), 3.18 (dd, 1H, J=14.6 and 5.3 Hz), 3.89 (dd, 1H, J=7.9 and 5.4 Hz), 6.96-7.00 (m, 2H), 7.02 (d, 1H, J=7.5 Hz), 7.28-7.32 (m, 1H).

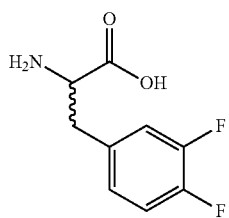 [SMILES: NC(Cc1ccc(F)c(F)c1)C(=O)O]

2-Amino-3-(3,4-difluorophenyl)propanoic acid (4d)

4.0 mg (40%), ¹HNMR (D$_2$O) δ 3.03 (dd, 1H, J=14.6 and 7.7 Hz), 3.16 (dd, 1H, J=14.4 and 5.1 Hz), 3.88 (t, 1H, J=6.5 Hz), 6.99-7.01 (br m, 1H), 7.11-7.21 (m, 2H).

Scheme 3: Alternate Preparation of 4a-4d.

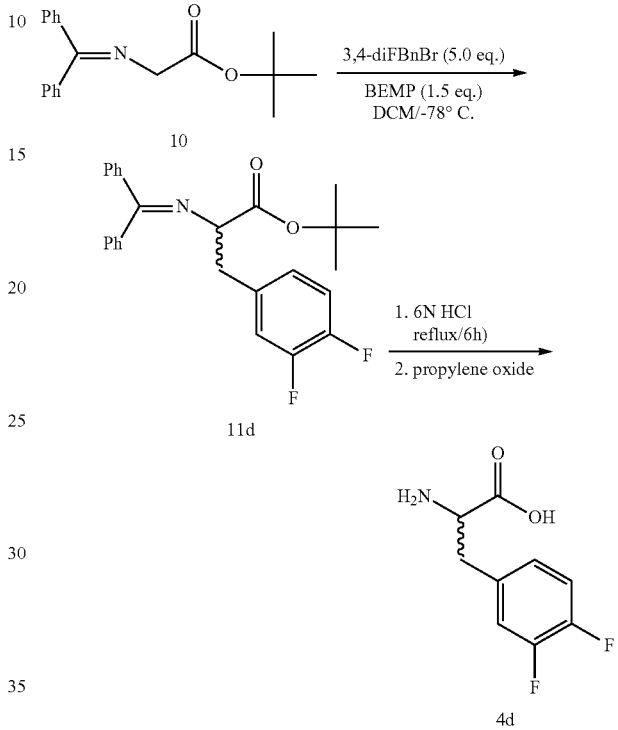

A 50-mL round-bottom flask sealed with a rubber septum and charged with 501 mg of 10 in 5 mL of dichloromethane under dry argon gas was treated dropwise via syringe 1.08 mL of 3,4-difluorobenzyl bromide. The contents were cooled to −78° C. and 0.734 mL of 2-tert-butylimino-2-diethylamino-1,3-dimethylperhydro-1,3,2-diazaphosphorine (BEMP) was added dropwise via syringe over 10 min. The solution was stirred at −78° C. for 8 h and was then stored at −20° C. overnight. The solution was concentrated to an oil which was chromatographed on silica gel using hexanes to remove the excess benzyl bromide and 95/5 hexanes/ethyl acetate to elute 11d (575 mg, 80%). Imine 11d (572 mg) was heated under reflux in 8 mL of 6N HCl for 6 h and was allowed to cool. The solution was washed with 2×5 mL of diethyl ether (106 mg of an insoluble solid was collected and later identified as the hydrochloride salt of the desired product). The solution was then transferred to a 200-mL rb flask and was concentrated to dryness in vacuo. Approximately 5 mL of boiling ethanol was used to transfer the residue to a 25-mL Erlenmeyer flask as a solution. Upon cooling the solution was treated with 400 uL of propylene oxide and was allowed to stand. The precipitate was collected by filtration and dried in vacuo to afford 104 mg (38%) of 4d.

Scheme 4: Preparation of N-Benzylamides 9.

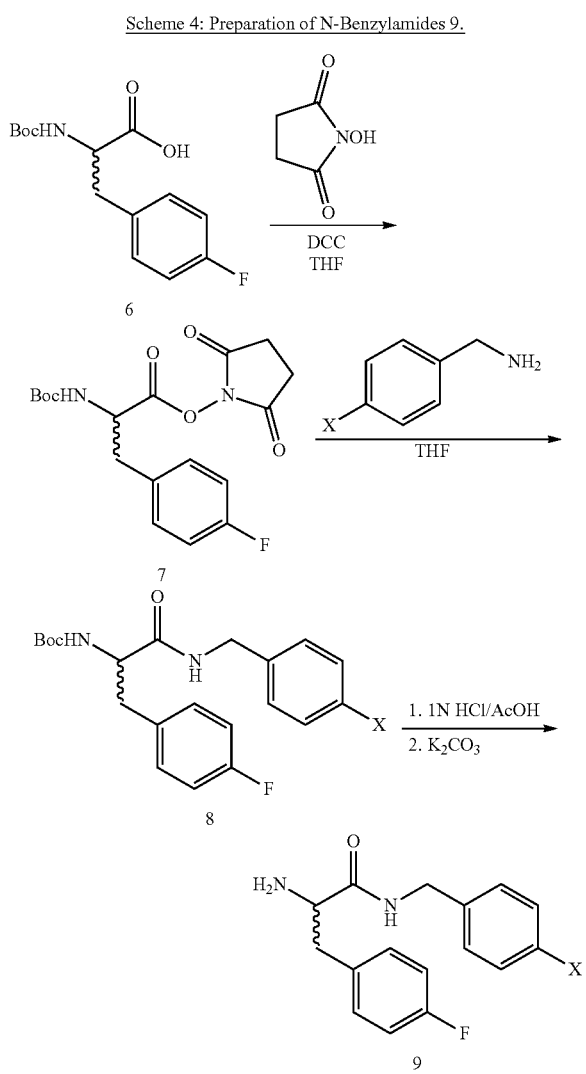

A 50-mL round-bottom flask was charged with 500.4 mg of protected amino acid 6 and 10 mL of THF. To the solution was added 204.1 mg of N-hydroxysuccinimide. The solution was chilled in an ice bath and 367 mg of dicyclohexylcarbodiimide was added. The mixture was stirred at 0-5° C. for 4 h and then was allowed to warm to room temperature and stand overnight. The mixture was chilled in an ice bath, was filtered, and the filtrate was concentrated to give 7 quantitatively as a white solid. Compound 7 (20-30 mg) was dissolved in 1 mL of THF and was treated with 1.2 equivalents of the benzylamine (X=H, Cl, or OMe) and the mixture was allowed to stand overnight. The reaction mixture was then filtered and the filtrate was evaporated to dryness. The residue was then chromatographed on 500 mg of silica gel using a step gradient as follows to give 8; dichloromethane, 99/1, 98/2, 97/3, 96/4, and 95/5 DCM/MeOH. Compound 8 was then treated with 500-700 uL of 1.0 M HCl in acetic acid and 50-70 uL of anisole and the solution was stirred for 1.5-2 h. The solution was added dropwise to 5 mL of cold, saturated potassium carbonate (pH9) and was extracted two times with 15 mL of diethyl ether. The combined extracts were washed once with 5 mL of potassium carbonate and once with brine and were dried over sodium sulfate. Concentration gave crude amides 9 which were chromatographed on 500 mg of silica gel using a step gradient as follows; dichloromethane, 99/1, 98/2, 97/3, 96/4, and 95/5 DCM/MeOH.

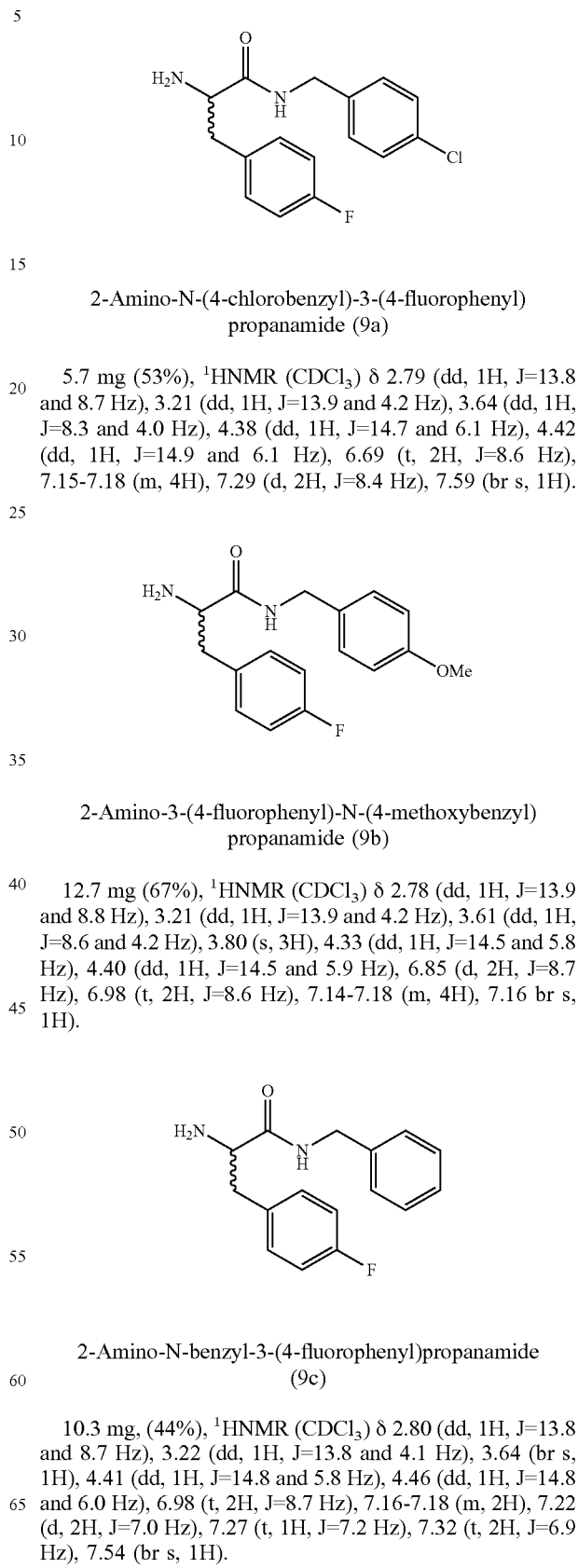

2-Amino-N-(4-chlorobenzyl)-3-(4-fluorophenyl) propanamide (9a)

5.7 mg (53%), $^1$HNMR (CDCl$_3$) δ 2.79 (dd, 1H, J=13.8 and 8.7 Hz), 3.21 (dd, 1H, J=13.9 and 4.2 Hz), 3.64 (dd, 1H, J=8.3 and 4.0 Hz), 4.38 (dd, 1H, J=14.7 and 6.1 Hz), 4.42 (dd, 1H, J=14.9 and 6.1 Hz), 6.69 (t, 2H, J=8.6 Hz), 7.15-7.18 (m, 4H), 7.29 (d, 2H, J=8.4 Hz), 7.59 (br s, 1H).

2-Amino-3-(4-fluorophenyl)-N-(4-methoxybenzyl) propanamide (9b)

12.7 mg (67%), $^1$HNMR (CDCl$_3$) δ 2.78 (dd, 1H, J=13.9 and 8.8 Hz), 3.21 (dd, 1H, J=13.9 and 4.2 Hz), 3.61 (dd, 1H, J=8.6 and 4.2 Hz), 3.80 (s, 3H), 4.33 (dd, 1H, J=14.5 and 5.8 Hz), 4.40 (dd, 1H, J=14.5 and 5.9 Hz), 6.85 (d, 2H, J=8.7 Hz), 6.98 (t, 2H, J=8.6 Hz), 7.14-7.18 (m, 4H), 7.16 br s, 1H).

2-Amino-N-benzyl-3-(4-fluorophenyl)propanamide (9c)

10.3 mg, (44%), $^1$HNMR (CDCl$_3$) δ 2.80 (dd, 1H, J=13.8 and 8.7 Hz), 3.22 (dd, 1H, J=13.8 and 4.1 Hz), 3.64 (br s, 1H), 4.41 (dd, 1H, J=14.8 and 5.8 Hz), 4.46 (dd, 1H, J=14.8 and 6.0 Hz), 6.98 (t, 2H, J=8.7 Hz), 7.16-7.18 (m, 2H), 7.22 (d, 2H, J=7.0 Hz), 7.27 (t, 1H, J=7.2 Hz), 7.32 (t, 2H, J=6.9 Hz), 7.54 (br s, 1H).

Scheme 5.

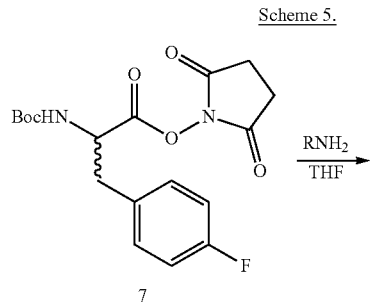

Compound 7 (20-30 mg) was dissolved in 1 mL of THF and was treated with 3.0 equivalents of isopropylamine or isobutylamine and the mixture was allowed to stand overnight. The reaction mixture was evaporated to dryness. The residue was then chromatographed on 500 mg of silica gel using a step gradient as follows; dichloromethane, 99/1, 98/2, 97/3, 96/4, and 95/5 DCM/MeOH. Compounds 14 were then treated with 500-700 uL of 1.0 M HCl in acetic acid and 50-70 uL of anisole and the solution was stirred for 1.5-2 h. The solution was added dropwise to 5 mL of cold, saturated potassium carbonate (pH9) and was extracted two times with 15 mL of diethyl ether. The combined extracts were washed once with 5 mL of potassium carbonate and once with brine and were dried over sodium sulfate. Concentration gave crude amides of 5g/5h which were chromatographed on 500 mg of silica gel using a step gradient as follows; dichloromethane, 99/1, 98/2, 97/3, 96/4, and 95/5 DCM/MeOH.

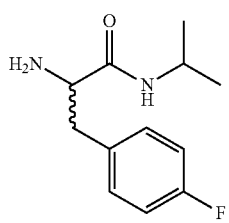 [SMILES: CC(C)NC(=O)C(N)Cc1ccc(F)cc1]

2-Amino-3-(4-fluorophenyl)-N-isopropylpropanamide (5g)

7.0 mg (38%), $^1$HNMR (CDCl$_3$) δ 1.12 (d, 3H, J=6.1 Hz), 1.13 (d, 3H, J=6.1 Hz), 1.50 (br s, 2H), 2.74 (dd, 1H, J=13.8 and 8.7 Hz), 3.17 (dd, 1H, J=13.8 and 4.3 Hz), 3.54 (dd, 1H, J=8.3 and 4.0 Hz), 4.05 (octet, 1H, J=7.1 Hz), 6.96-7.02 (m, 3H), 7.17-7.19 (m, 2H).

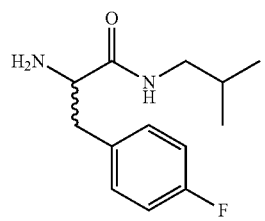

2-Amino-3-(4-fluorophenyl)-N-isobutylpropanamide (5h)

6.7 mg (38%), $^1$HNMR (CDCl$_3$) δ 0.89 (d, 3H, J=6.7 Hz), 0.94 (d, 3H, J=6.7 Hz), 1.75 (nonet, 1H, J=6.7 Hz), 2.74 (dd, 1H, J=13.8 and 8.9 Hz), 3.08 (nonet, 2H, J=6.5 Hz), 3.21 (dd, 1H, J=13.9 and 4.0 Hz), 3.59 (br s, 1H), 7.00 (t, 2H, J=8.7 Hz), 7.17-7.20 (m, 2H), 7.31 (br s, 1H).

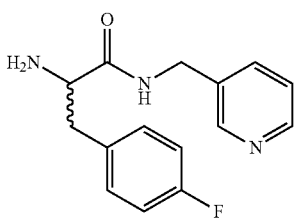 [SMILES: NC(Cc1ccc(F)cc1)C(=O)NCc1cccnc1]

2-Amino-3-(4-fluorophenyl)-N-(pyridin-3-ylmethyl)propanamide (5i)

Using the procedure above for 5g and 5h gave 2-3 mg of crude product. The aqueous phase was concentrated to dryness and was then continuously extracted for six hours in a Soxhlet extractor using dichloromethane affording 13 mg of material which was chromatographed as above for 5g/5h to give 7.0 mg (41%), $^1$HNMR (CDCl$_3$) δ 2.79 (dd, 1H, J=13.9 and 8.7 Hz), 3.22 (dd, 1H, J=13.9 and 4.1 Hz), 3.65 (dd, 1H, J=8.7 and 4.2 Hz), 4.43 (dd, 1H, J=15.0 and 6.0 Hz), 4.48 (dd, 1H, J=15.0 and 6.1 Hz), 6.99 (t, 2H, J=8.7 Hz), 7.15-7.18 (m, 2H), 7.26 (dd, 1H, J=7.8 and 4.9 Hz), 7.57 (d, 1H, J=7.8 Hz), 7.70 (br s, 1H), 8.52 (br s, 2H).

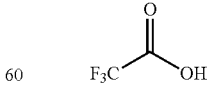 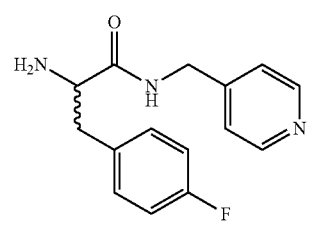

2-amino-3-(4-fluorophenyl)-N-(pyridin-4-ylmethyl) propanamide 2,2,2-trifluoroacetate (5j)

Using the procedure above for 5g and 5h gave intermediate 14j. The Boc group was removed by treatment with 25% trifluoroacetic acid in dichloromethane over three hours. The reaction mixture was evaporated to 32.9 mg of a residue which was chromatographed of silica gel using 18:2:1 isopropanol:methanol:ammonium hydroxide and proceeding to 9:2:1 to give 4.2 mg (14%) and 19.3 mg of contaminated target material, $^1$HNMR (CD$_3$OD) δ 3.13 (dd, 1H, J=13.9 and 8.7 Hz), 3.20 (dd, 1H, J=13.8 and 7.9 Hz), 4.13 (t, 1H, J=7.5 Hz), 4.37 (d, 1H, J=16.0 Hz), 4.48 (d, 1H, J=16.0 Hz), 7.08 (t, 2H, J=8.7 Hz), 7.27-7.29 (m, 4H), 8.55 (br s, 2H).

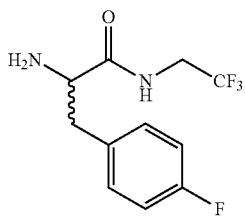 [SMILES: NC(Cc1ccc(F)cc1)C(=O)NCC(F)(F)F]

2-Amino-3-(4-fluorophenyl)-N-(2,2,2-trifluoroethyl) propanamide (5k)

8.8 mg (42%), $^1$HNMR (CDCl$_3$) δ 2.79 (dd, 1H, J=14.0 and 8.8 Hz), 3.21 (dd, 1H, J=13.9 and 3.9 Hz), 3.67 (br s, 1H), 3.82-4.00 (m, 2H), 7.01 (t, 2H, J=8.6 Hz), 7.16-7.18 (m, 2H), 7.79 (br s, 1H).

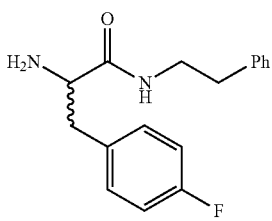 [SMILES: NC(Cc1ccc(F)cc1)C(=O)NCCc1ccccc1]

2-Amino-3-(4-fluorophenyl)-N-phenethylpropanamide (5l)

14.4 mg (64%); $^1$HNMR (CDCl$_3$) δ 2.69 (dd, 1H, J=13.9 and 8.8 Hz), 2.79 (t, 2H, J=7.0 Hz), 3.17 (dd, 1H, J=13.9 and 4.2 Hz), 3.46-3.57 (m, 3H), 6.99 (t, 2H, J=8.6 Hz), 7.14-7.16 (m, 4H), 7.20-7.25 (m, 2H), 7.26-7.30 (m, 2H).

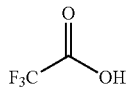 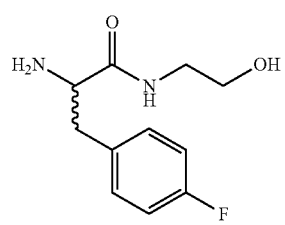

2-Amino-3-(4-fluorophenyl)-N-(2-hydroxyethyl) propanamide 2,2,2-trifluoroacetate (5m)

Using the procedure above for 5g and 5h gave intermediate 14m. The Boc group was removed by treatment with 25% trifluoroacetic acid in dichloromethane over three hours. The reaction mixture was evaporated to a residue which was chromatographed of silica gel using 95:5 and 9:1 dichloromethane:methanol to give 18.7 mg (69%) of 5m; $^1$HNMR (D$_2$O) δ 3.11 (m, 2H), 3.22 (m, 2H), 3.44 (m, 1H), 3.50 (m, 1H), 4.08 (t, 1H, J=7.4 Hz), 7.07 (t, 2H, J=8.9 Hz), 7.20-7.22 (m, 2H); $^1$HNMR (CD$_3$OD) δ 3.06 (dd, 1H, J=13.8 and 7.3 Hz), 3.19 (dd, 1H, J=12.8 and 6.5 Hz), 3.27-3.37 (m, 2H), 3.52-3.62 (m, 2H), 4.00 (br t, 1H, J=5.9 Hz), 7.11 (t, 2H, J=8.7 Hz), 7.29-7.32 (m, 2H).

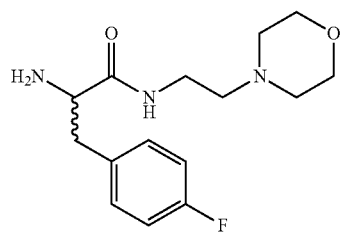

2-Amino-3-(4-fluorophenyl)-N-(2-morpholinoethyl) propanamide (5n)

Appreciable water-solubility required three extractions of the basic aqueous phase with dichloromethane to give 10.9 mg (47%); $^1$HNMR (CDCl$_3$) δ 2.41-2.46 (m, 6H), 2.76 (dd, 1H, J=13.8 and 8.6 Hz), 3.17 (dd, 1H, J=13.8 and 4.6 Hz), 3.35 (q, 2H, J=5.9 Hz), 3.57 (dd, 1H, J=8.4 and 4.6 Hz), 3.67 (t, 4H, J=4.6 Hz), 7.00 (t, 2H, J=8.6 Hz), 7.17-7.20 (m, 2H), 7.35 (br s, 1H).

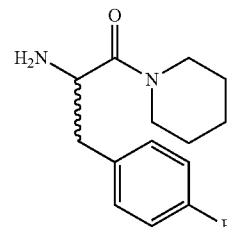

2-Amino-3-(4-fluorophenyl)-1-(piperidin-1-yl)propan-1-one (5o)

10.1 mg (59%); $^1$HNMR (CDCl$_3$) δ 1.14-1.22 (m, 1H), 1.40-1.63 (m, 5H), 2.74 (dd, 1H, J=13.4 and 7.2 Hz), 2.91 (dd, 1H, J=13.4 and 6.7 Hz), 3.12-3.16 (m, 1H), 3.27-3.32 (m, 1H), 3.49-3.58 (m, 2H), 3.93 (br s, 1H), 6.98 (t, 2H, J=8.6 Hz), 7.15-7.18 (m, 2H).

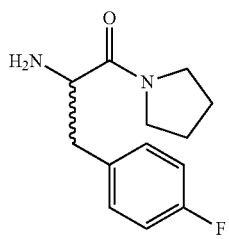 [SMILES: NC(Cc1ccc(F)cc1)C(=O)N1CCCC1]

2-Amino-3-(4-fluorophenyl)-1-(pyrrolidin-1-yl)propan-1-one (5p)

Appreciable water-solubility required three extractions of the basic aqueous phase with dichloromethane to give 10.8 mg (58%); $^1$HNMR (CDCl$_3$) δ 1.67-1.86 (m, 4H), 2.77 (dd, 1H, J=13.3 and 7.0 Hz), 2.82-2.86 (m, 1H), 2.92 (dd, 1H, J=13.2 and 7.4 Hz), 3.35-3.40 (m, 2H), 3.45-3.50 (m, 1H), 3.69 (t, 1H, J=7.1 Hz), 6.97 (t, 2H, J=8.6 Hz), 7.15-7.18 (m, 2H).

(dd, 1H, J=8.3 and 5.8 Hz), 6.96 (br s, 1H), 7.10-7.14 (m, 2H), 7.23-7.27 (m, 1H), 7.29-7.32 (m, 1H), 7.34 (br s, 1H).

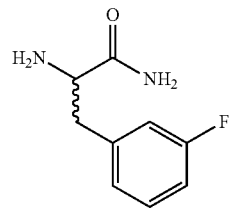

2-Amino-3-(3-fluorophenyl)propanamide (5b)

9.0 mg (99%), $^1$HNMR (DMSO-d$_6$) δ 2.65 (dd, 1H, J=13.2 and 8.2 Hz), 2.93 (dd, 1H, J=13.3 and 4.9 Hz), 3.39

Scheme 6: Preparation of Amino Acid Amides 5

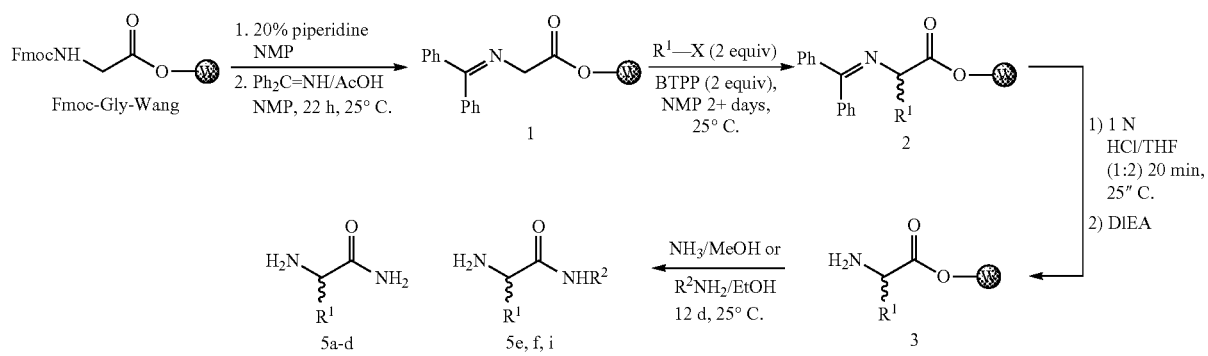

The procedure in Scheme 2 for the preparation of resins 3 was used. Resins 3 were then treated with 7N methanolic ammonia or 33% methylamine in ethanol or isoamylamine in ethanol for four to twelve days. The vessels were drained and the resins washed with THF. The filtrates were then evaporated to dryness to afford crude amides 5a-f, and i.

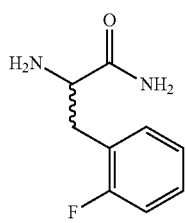 [SMILES: NC(=O)C(N)Cc1ccccc1F]

2-Amino-3-(2-fluorophenyl)propanamide (5a)

7.1 mg (78%), $^1$HNMR (DMSO-d$_6$) δ 2.65 (dd, 1H, J=13.3 and 8.3 Hz), 2.94 (dd, 1H, J=13.3 and 5.2 Hz), 3.36

(dd, 1H, J=7.9 and 5.2 Hz), 7.01-7.04 (m, 2H), 7.06 (d, 2H, J=7.9 Hz), 7.29-7.33 (m, 1H), 7.36 (br s, 1H).

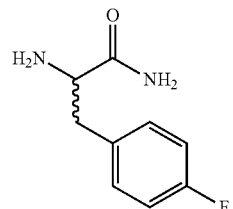

2-Amino-3-(4-fluorophenyl)propanamide (5c)

15.2 mg (38%), $^1$HNMR (D$_2$O) δ 2.82 (dd, 1H, J=13.7 and 6.9 Hz), 2.87 (dd, 1H, J=13.6 and 6.7 Hz), 3.57 (t, 1H, J=6.8 Hz), 7.02 (t, 2H, J=8.9 Hz), 7.18 (m, 2H).

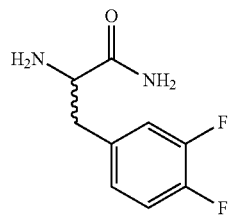 [SMILES: NC(=O)C(N)Cc1ccc(F)c(F)c1]

2-Amino-3-(3,4-difluorophenyl)propanamide (5d)

4.0 mg, (40%), ¹HNMR (5% CD₃OD in CDCl₃) δ 2.75 (dd, 1H, J=13.5 and 8.7 Hz), 3.14 (br d, 1H, J=13.1 Hz), 3.61 (br s, 1H), 6.00 (br s, 1H), 6.94-6.96 (br m, 1H), 7.05-7.14 (m, 2H), 7.18 (br s, 1H).

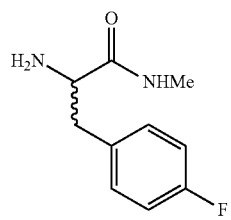 [SMILES: CNC(=O)C(N)Cc1ccc(F)cc1]

2-Amino-3-(4-fluorophenyl)-N-methylpropanamide (5e)

3.9 mg (40%), ¹HNMR (CD₃OD) 2.60 (s, 3H), 2.73 (dd, 1H, J=13.5 and 7.0 Hz), 2.88 (dd, 1H, J=13.5 and 6.7 Hz), 3.40 (t, 1H, J=6.6 Hz), 6.94 (t, 2H, J=8.8 Hz), 7.12-7.15 (m, 2H).

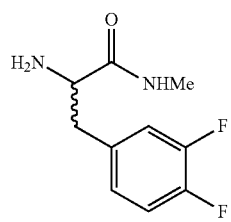 [SMILES: CNC(=O)C(N)Cc1ccc(F)c(F)c1]

2-Amino-3-(3,4-difluorophenyl)-N-methylpropanamide (5i)

4.4 mg (41%), ¹HNMR (CDCl₃) 2.73 (dd, 1H, J=13.9 and 8.9 Hz), 2.82 (d, 3H, J=4.9 Hz), 3.20 (dd, 1H, J=13.9 and 4.1 Hz), 3.58 (dd, 1H, J=8.8 and 4.1 Hz), 6.91-6.94 (br m, 1H), 7.04 (ddd, 1H, J=10.6, 7.5, and 1.9 Hz), 7.07-7.13 (m, 1H), 7.21 (br s, 1H).

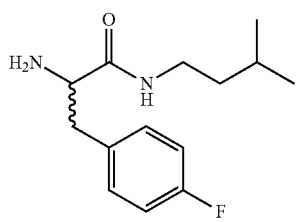 [SMILES: CC(C)CCNC(=O)C(N)Cc1ccc(F)cc1]

2-Amino-3-(4-fluorophenyl)-N-isopentylpropanamide (5f)

5.6 mg (44%), ¹HNMR (CDCl₃) δ 0.91 (d, 6H, J=6.7 Hz), 1.37 (q, 2H, J=7.3 Hz), 1.58 (heptet, 1H, J=6.7 Hz), 2.73 (dd, 1H, J=13.9 and 8.9 Hz), 3.20 (dd, 1H, J=13.9 and 4.2 Hz), 3.26 (ddd, 2H, J=9.1, 7.1, 1.3 Hz), 3.56 (dd, 1H, J=8.8 and 4.2 Hz), 7.00 (t, 2H, J=8.6 Hz), 7.14 (br s, 1H), 7.14-7.19 (m, 2H).

Scheme 7: Alternate Preparation of Primary amides (5a-5d).

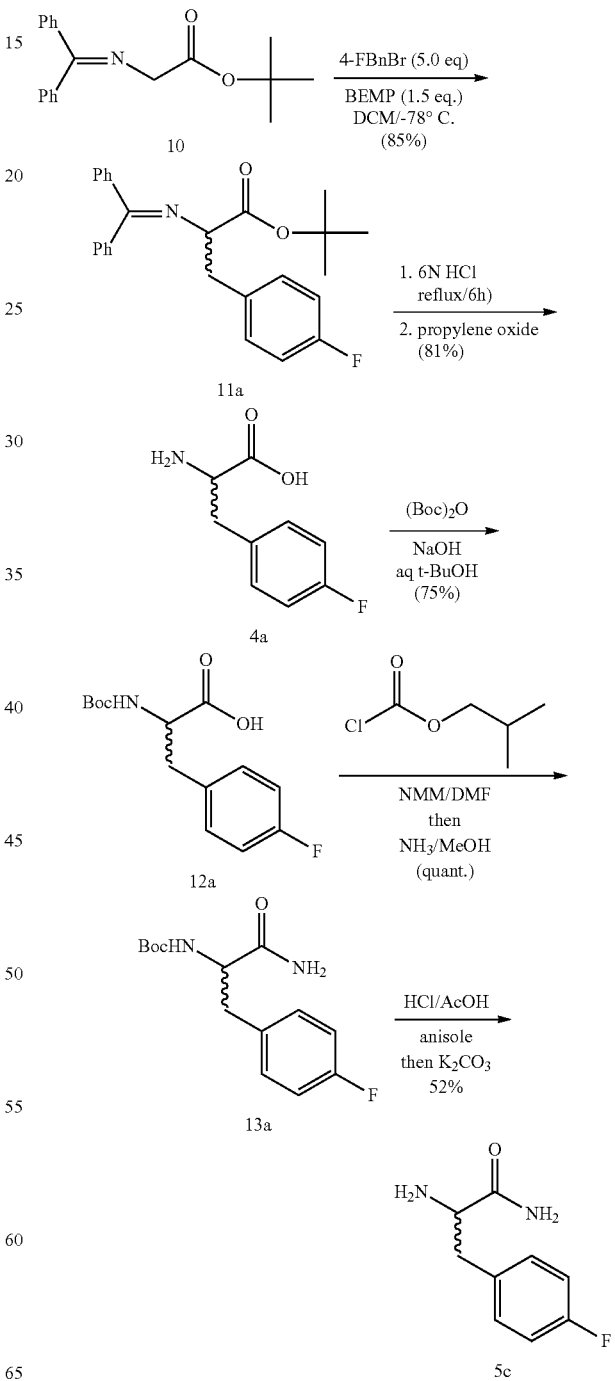

Compound 4a (prepared as described above for 4d), 209.1 mg, was treated with 711 µL of t-butanol, 142.8 µL of water, and 570.2 µL of 2.0 N NaOH. To this solution was added 268.5 µL of di-t-butyl-dicarbonate. The solution was stirred overnight and was then transferred to a separatory funnel containing 10 mL of diethylether and mixed. The layers were separated and the aqueous phase was washed with 5 mL of diethyl ether and was adjusted to pH2-3 with 1N HCl. The mixture was extracted with 2×10 mL of ethyl acetate. The combined extracts were washed with 2 mL of water and were dried (MgSO$_4$). Concentration gave 242.4 mg of 12a. Compound 12a (117 mg) under dry argon gas was dissolved in 874 µL of DMF and the solution was chilled to −9° C. To the solution was then added 45.6 µL of N-methylmorpholine followed by 56.6 µL of isobutyl chloroformate. After 5-10 min, 600 µL of 7N ammonia in methanol was added. The mixture was stirred at −15 to 2° C. over a 4.5 h period and was then added to 20-25 mL of crushed ice and saturated sodium bicarbonate. The mixture was extracted with 2×15 mL of ethyl acetate. The combined extracts were washed once with 5 mL of water, once with 5 mL of 10% citric acid, and once with water and were dried (MgSO$_4$). Concentration gave 123.8 mg of 13a as a white solid. To 121.8 mg of 13a was added a solution of 782 µL of 1.0 M HCl in acetic acid and 77.2 µL of anisole. After one hour, 5 mL of diethyl ether was added. The precipitate was collected and was dried in vacuo to afford 70 mg of 5c as its hydrochloride salt. A portion (35.3 mg) was stirred in 3 mL of saturated potassium carbonate for 3 h. Collection afforded 15.2 mg of 5c. For additional information, see U.S. Pat. No. 4,265,808, disclosure of which is incorporated by reference in its entirety to the extent that it is not inconsistent with the explicit teachings of this specification.

Referring now to FIG. 1, compounds were synthesized and tested for the chemical activity. Compounds in red (i.e., 2-F, 3-F, 4-F, and 4-I) showed activity in preliminary screens.

Figure 2:
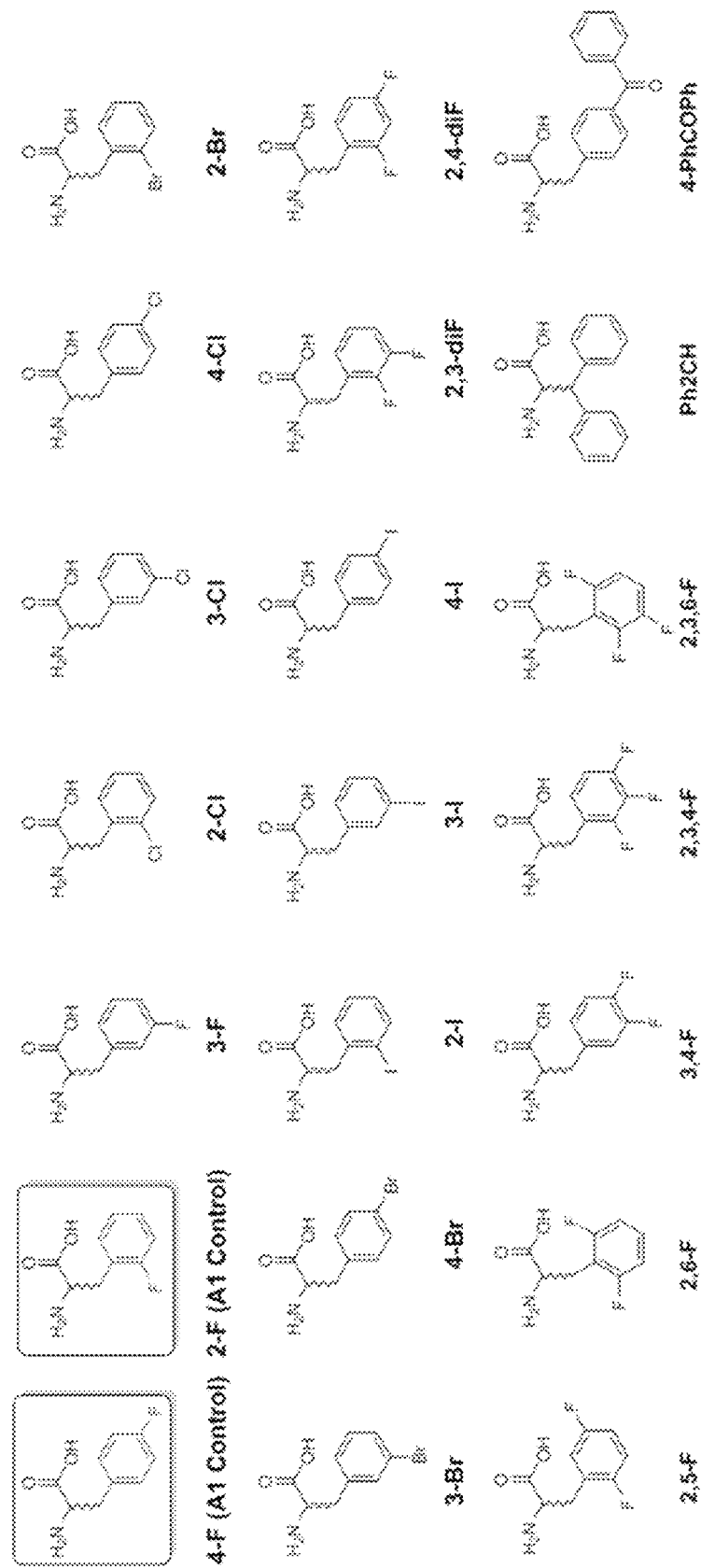
FIG. 2. A list showing a structure index for some 4-F-Phe and 2-F-Phe analogs.

Referring now to FIG. 2, twenty-one "unnatural" amino acids were synthesized.

Effect of Some Exemplary Compounds on Biofilm Formation

Figure 3:
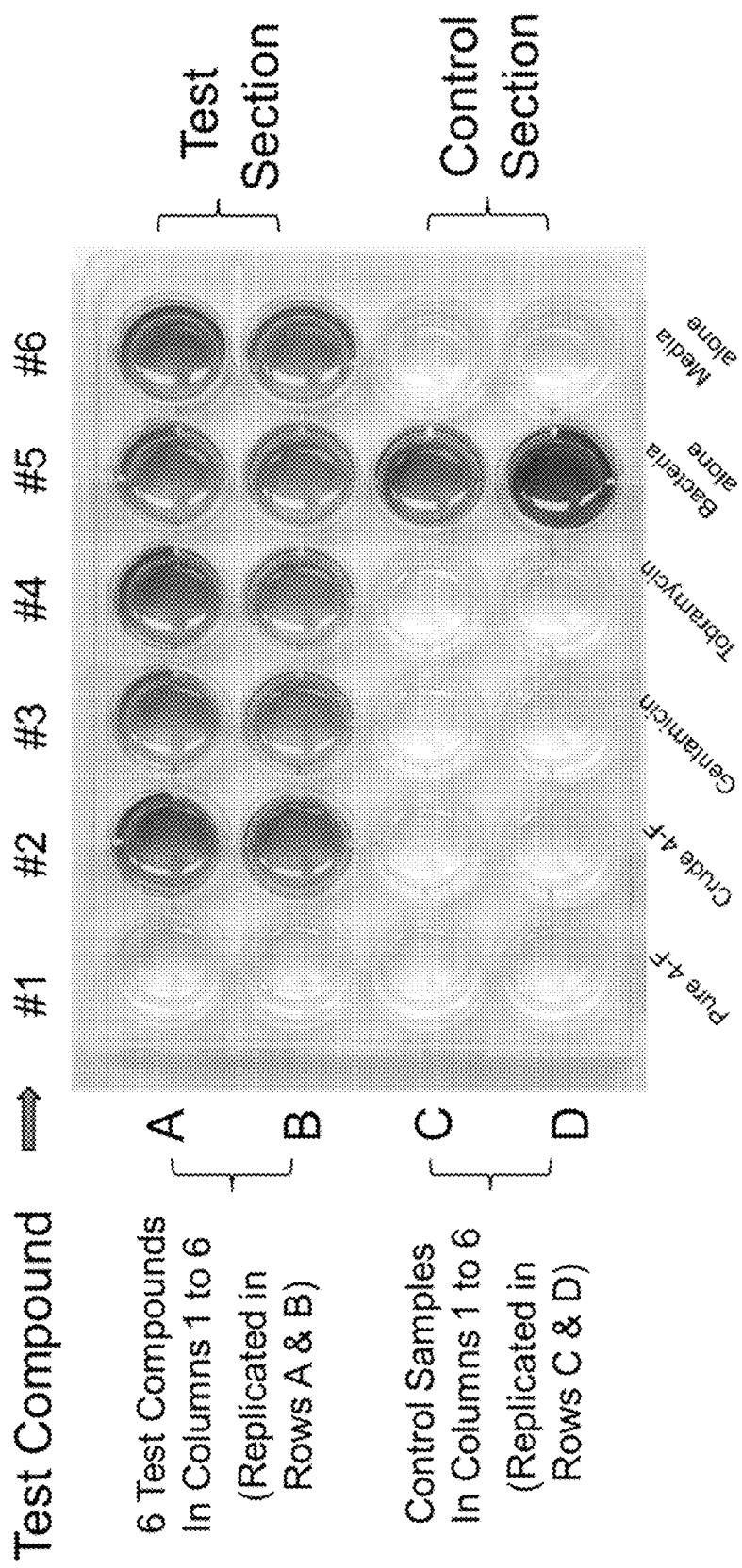
FIG. 3. Schematic diagram illustrating a reproducible *P. aeruginosa* Biofilm Assay.
Figure 4:
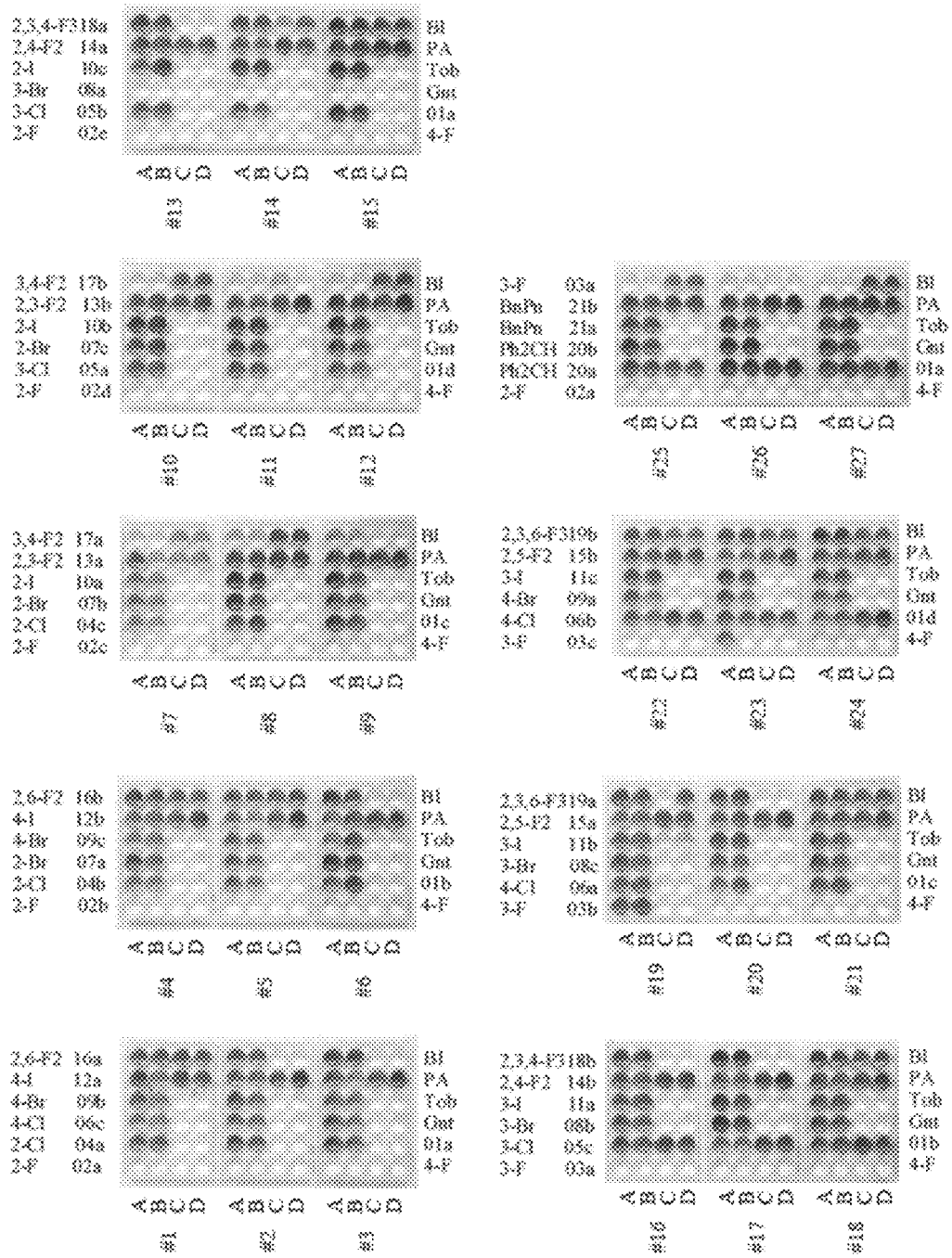
FIG. 4. Photographs showing the effects of some compounds on the growth of *P. aeruginosa* as indicated by biofilm formation. Gentamicin (Gent) and Tobramycin (Tob) were used as positive controls.
Figure 5:
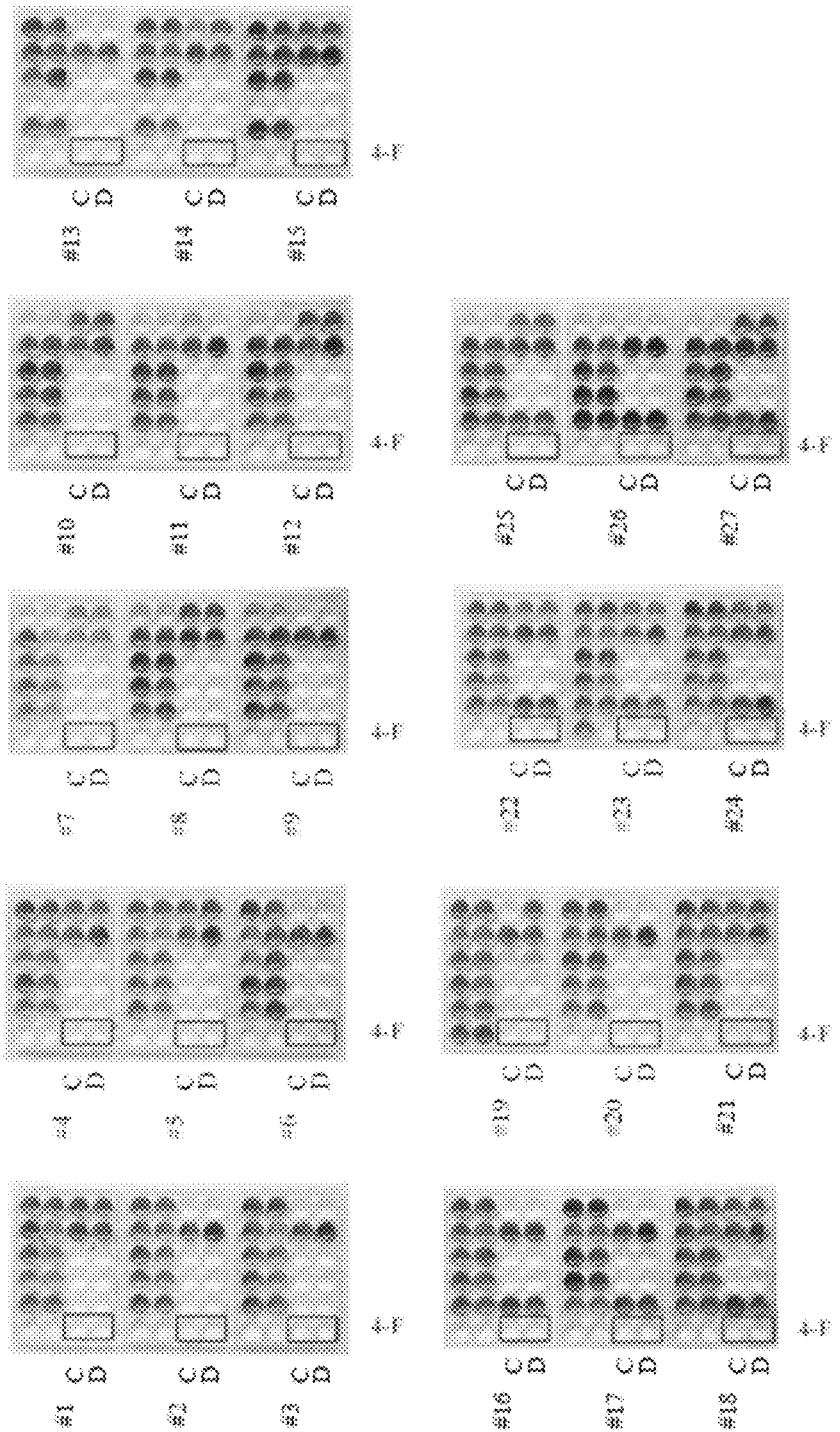
FIG. 5. Photographs showing the effects of 4-fluorophenylalanine (4-F; red box) the growth of *P. aeruginosa* as indicated by biofilm formation.
Figure 6:
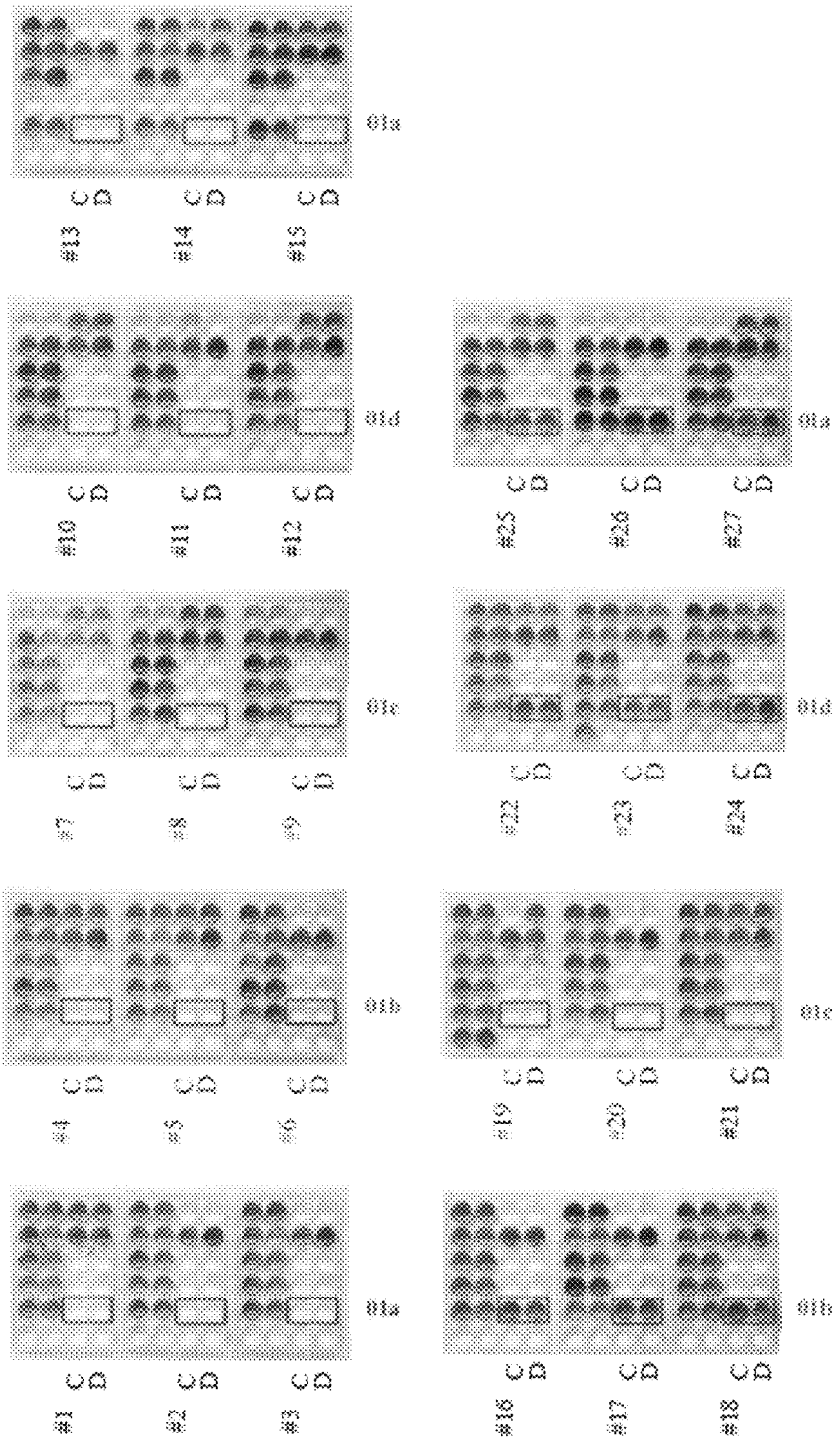
FIG. 6. Photographs showing the effects of some separately synthesized crude lots of 4-fluorophenylalanine (1a-1d; red box) on the growth of *P. aeruginosa* as indicated by biofilm formation.
Figure 7:
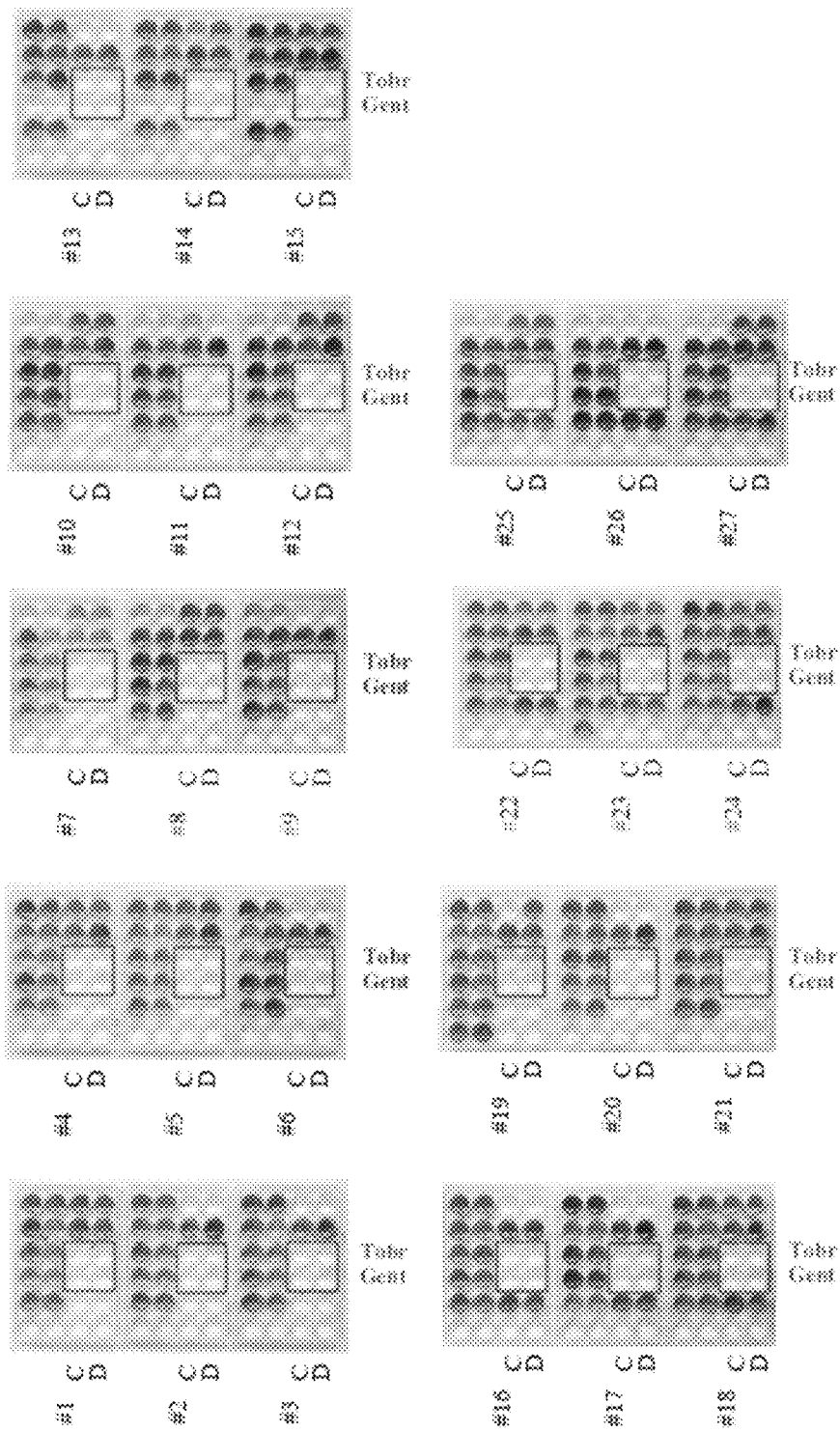
FIG. 7. Photographs showing the effects of Gentamicin (Gent; red box) and Tobramycin (Tob; red box) on the growth of *P. aeruginosa* as indicated by biofilm formation.
Figure 8:
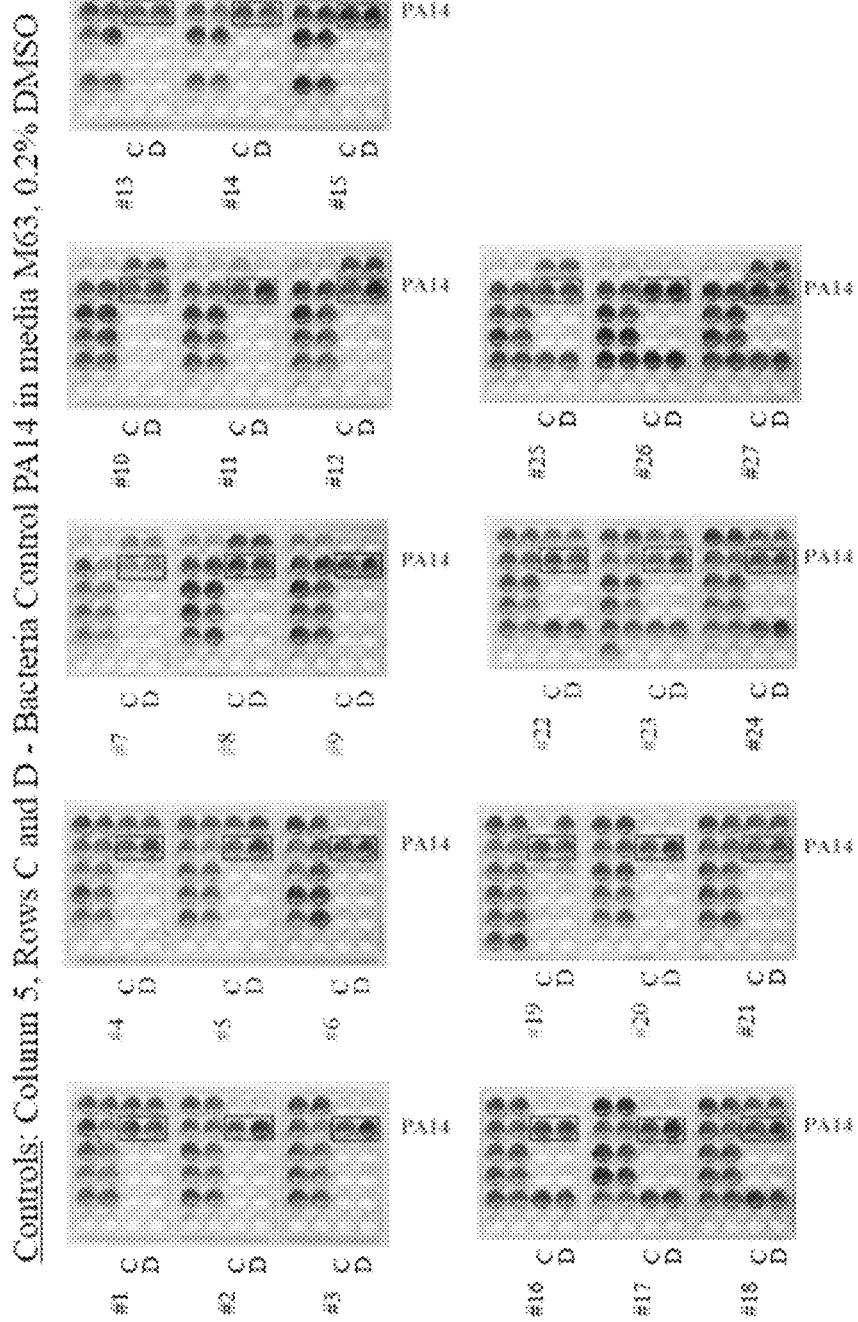
FIG. 8. Photographs showing the effects of bacteria alone (PA14; red box) on the growth of *P. aeruginosa* as indicated by biofilm formation.
Figure 9:
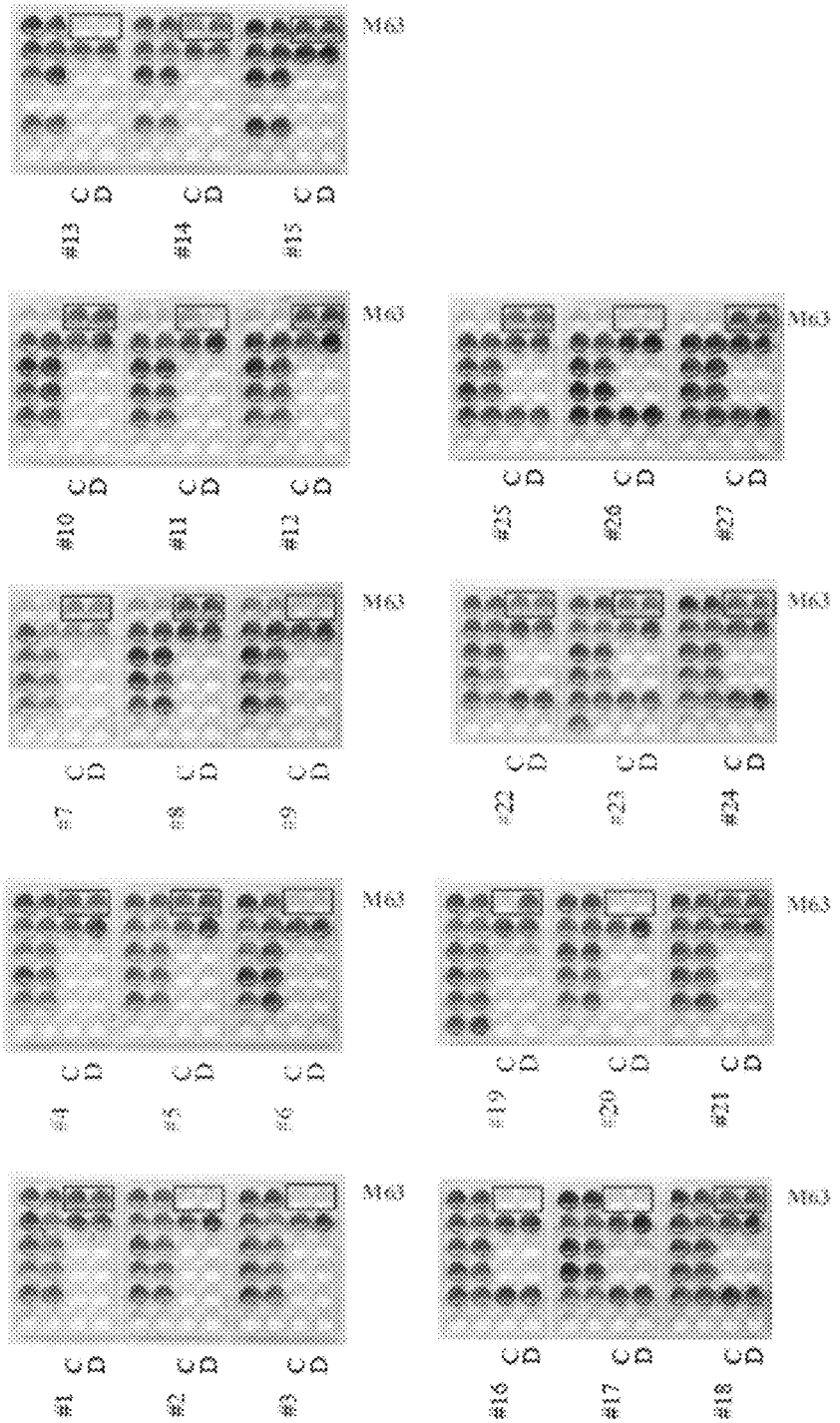
FIG. 9. Photographs showing the effects of media alone (M63; red box) on the growth of *P. aeruginosa* as indicated by biofilm formation.
Figure 10:
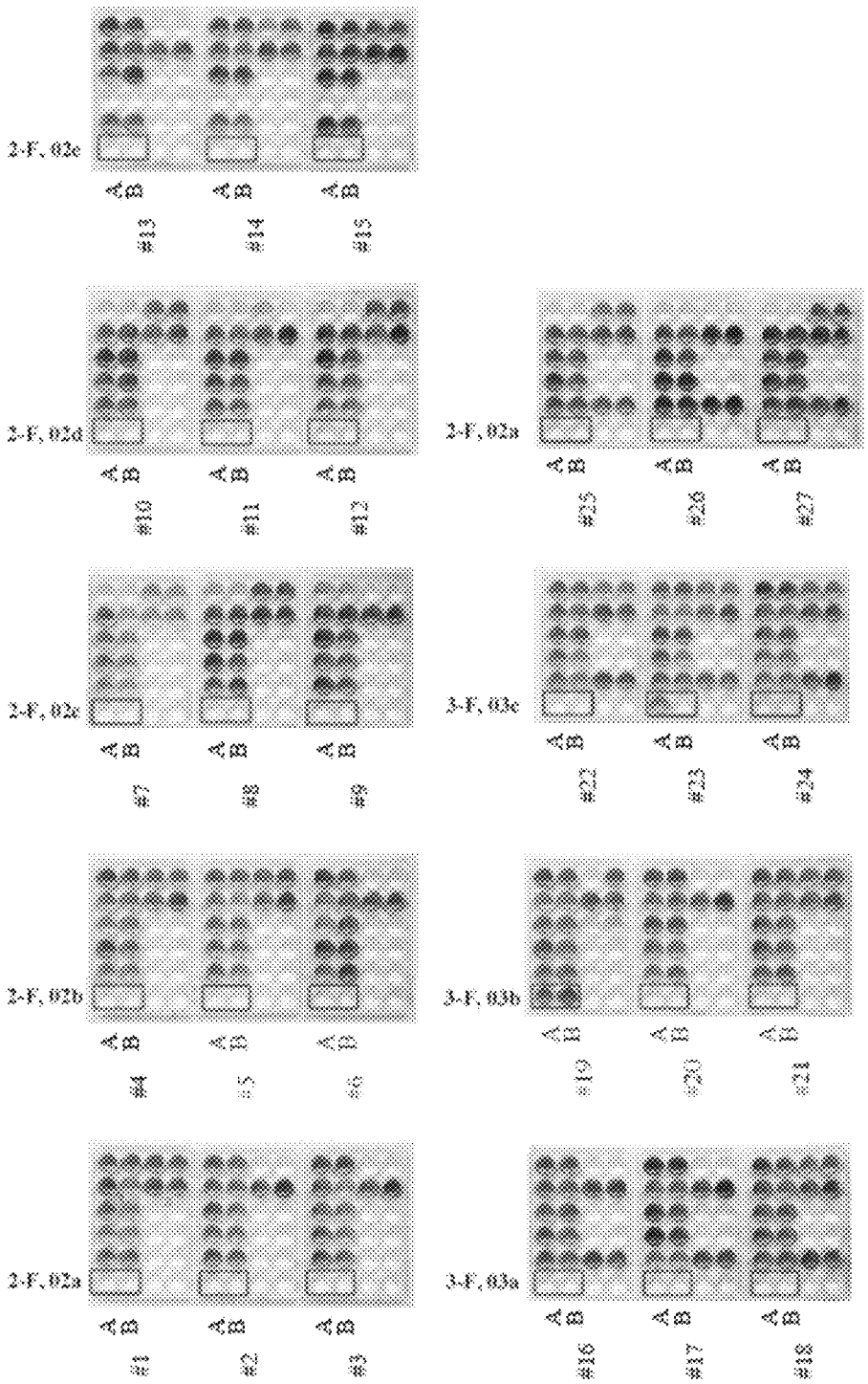
FIG. 10. Photographs showing the effects of separate lots of either crude 2-fluorophenylalanine (2-F, lots 02a, 02b, 02c, 02d, and 02e; red box) or crude 3-fluorophenylalanine (3-F, lots 031, 03b, or 03c; red box) on the growth of *P. aeruginosa* as indicated by biofilm formation.
Figure 11:
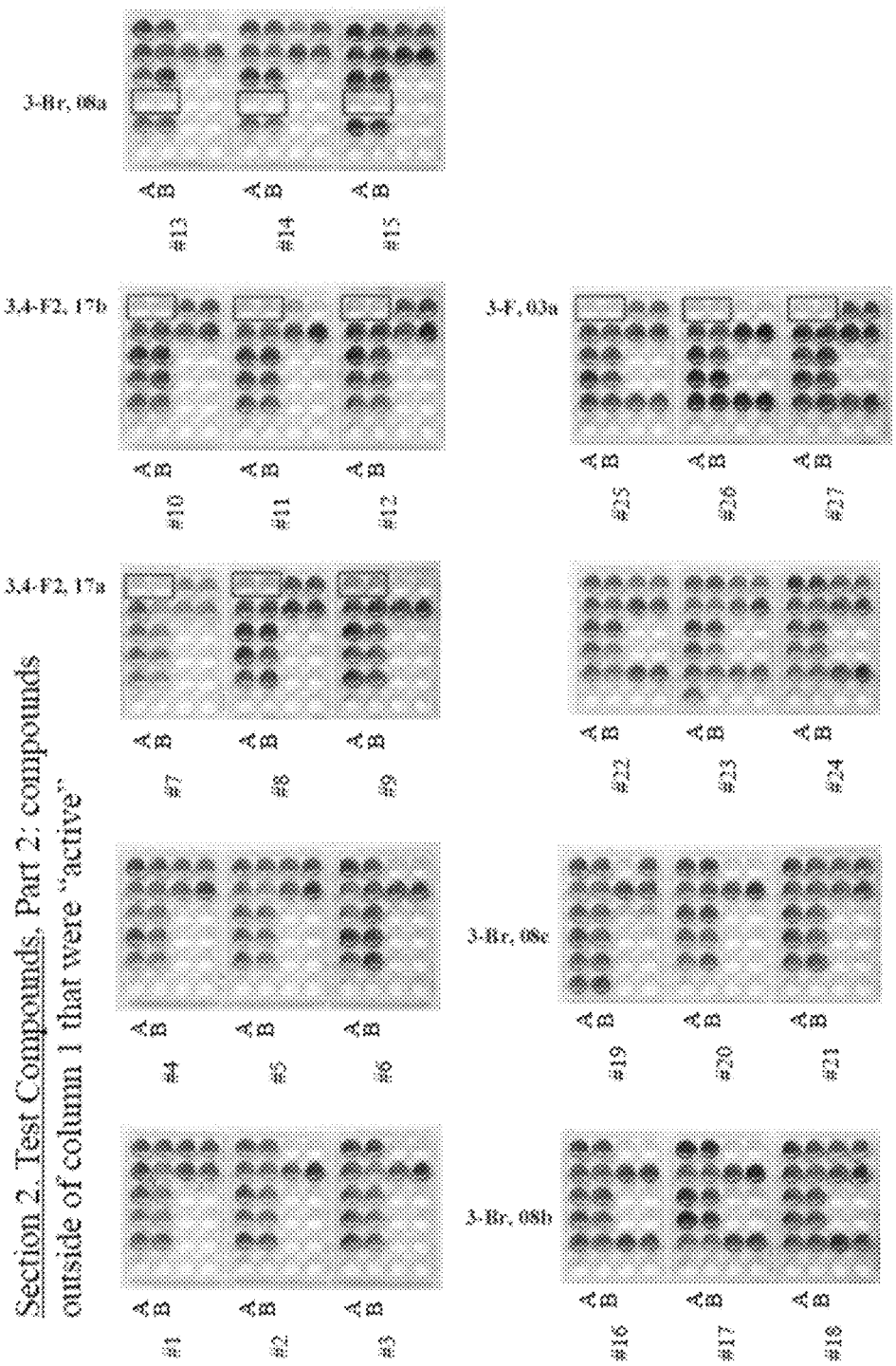
FIG. 11. Photographs showing the effects of separate lots of 3,4-difluorophenylalanine (3,4-F2; red box), lot 08a of 3-bromophenylalanine (3-Br; red box), and lot 03a of 3-fluorophenylalanine (3-F; red box) on the growth of *P. aeruginosa* as indicated by biofilm formation.
Figure 12:
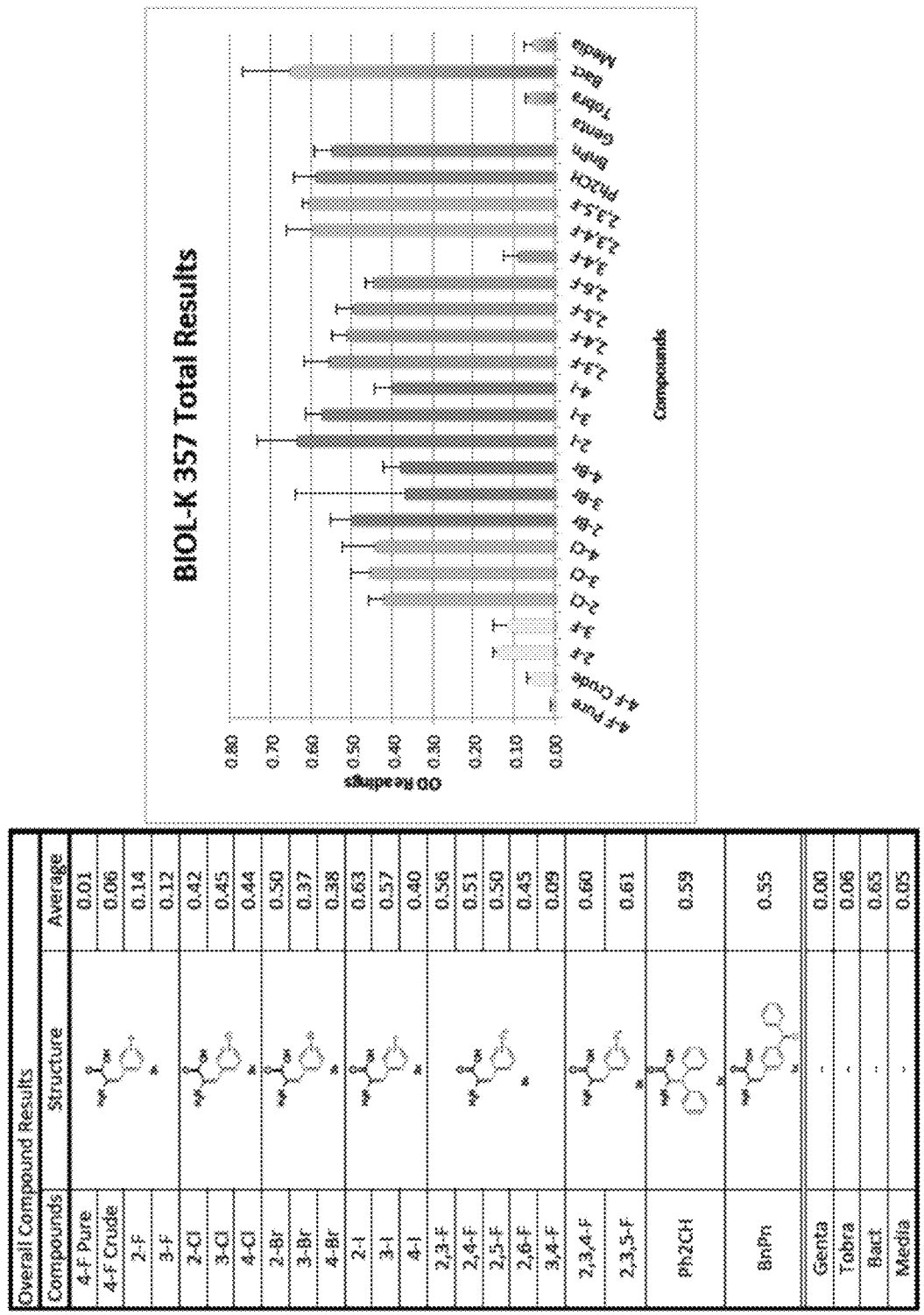
FIG. 12. Graph summarizing the effects of some compounds on the growth of *P. aeruginosa* as indicated by biofilm formation.
Figure 13:
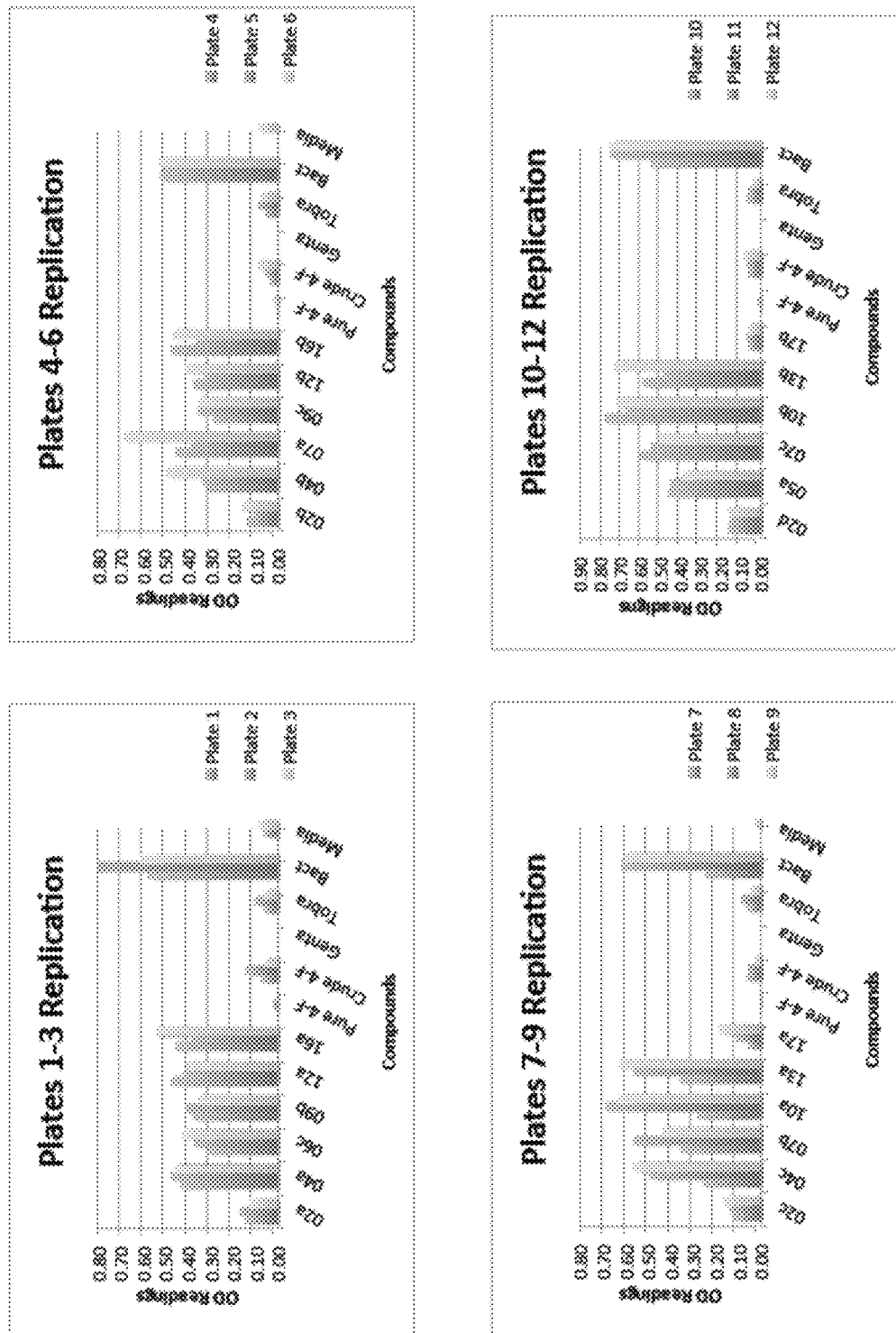
FIG. 13. Graphs illustrating the effects of some compounds on the growth of *P. aeruginosa* as indicated by biofilm formation determine in microtiter plates.
Figure 14:
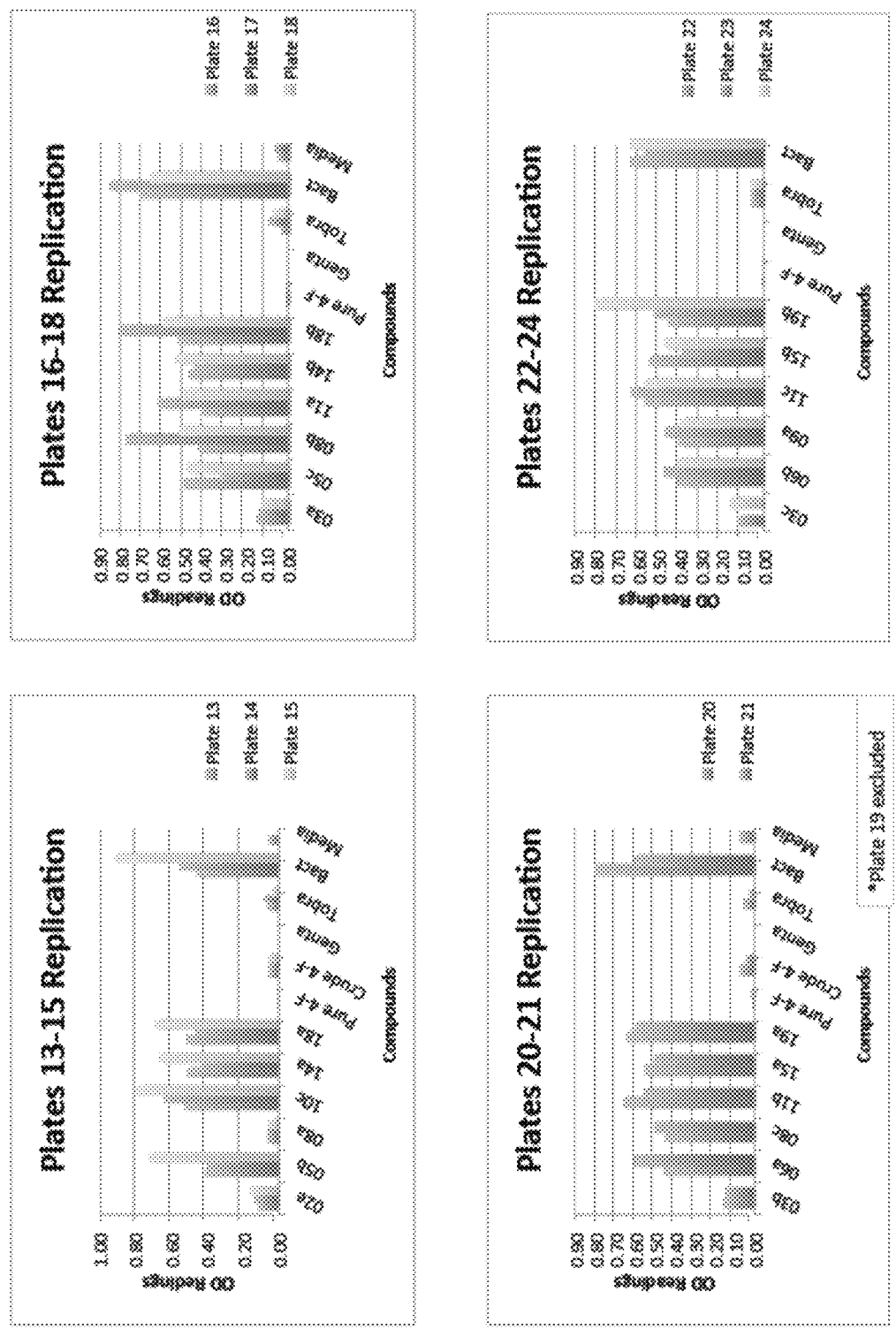
FIG. 14. Graphs illustrating the effects of some compounds on the growth of *P. aeruginosa* with biofilm formation determined in microtiter plates.
Figure 15:
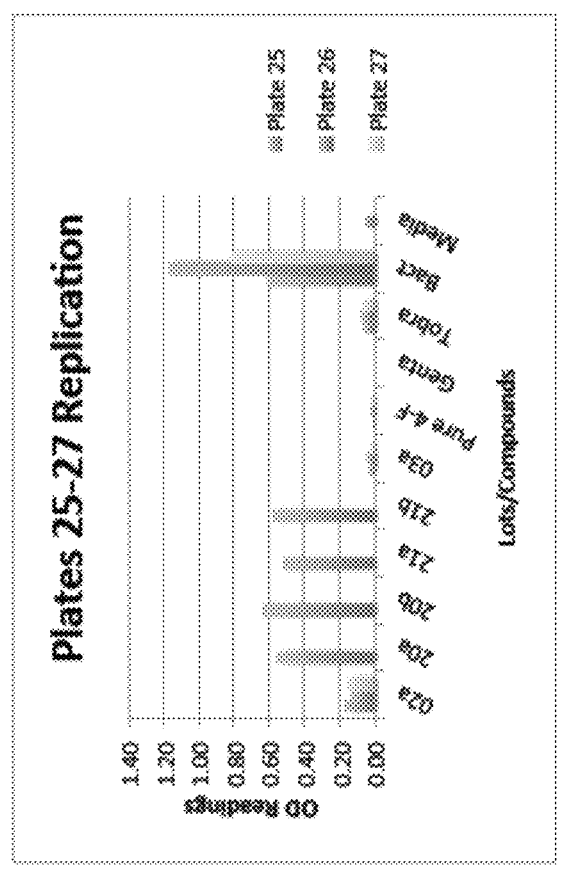
FIG. 15. Graph illustrating the effects of some compounds on the growth of *P. aeruginosa* with biofilm formation determine in microtiter plates.
Figure 16:
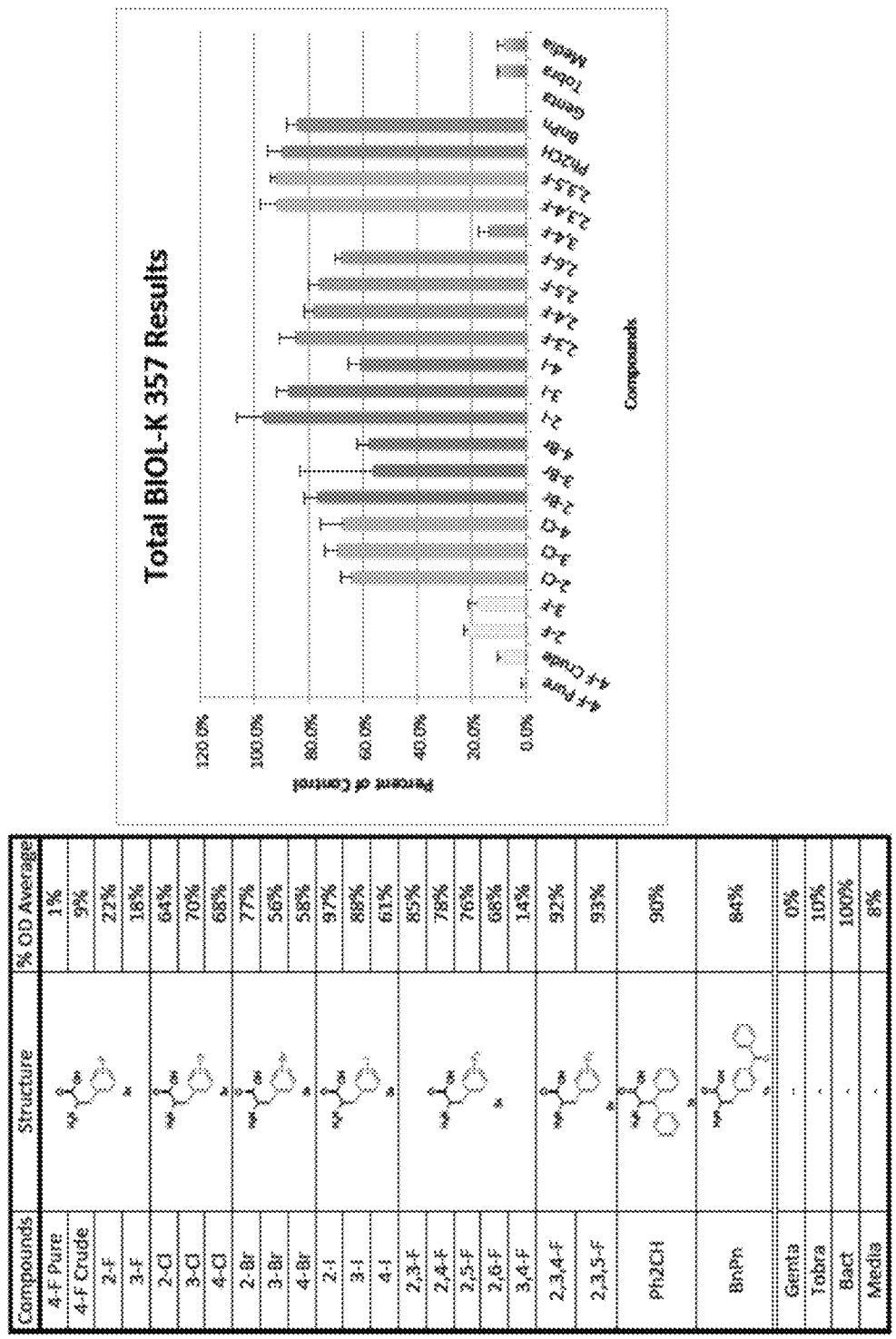
FIG. 16. Graph summarizing the effects of some compounds on the growth of *P. aeruginosa* as indicated by biofilm formation.
Figure 17:
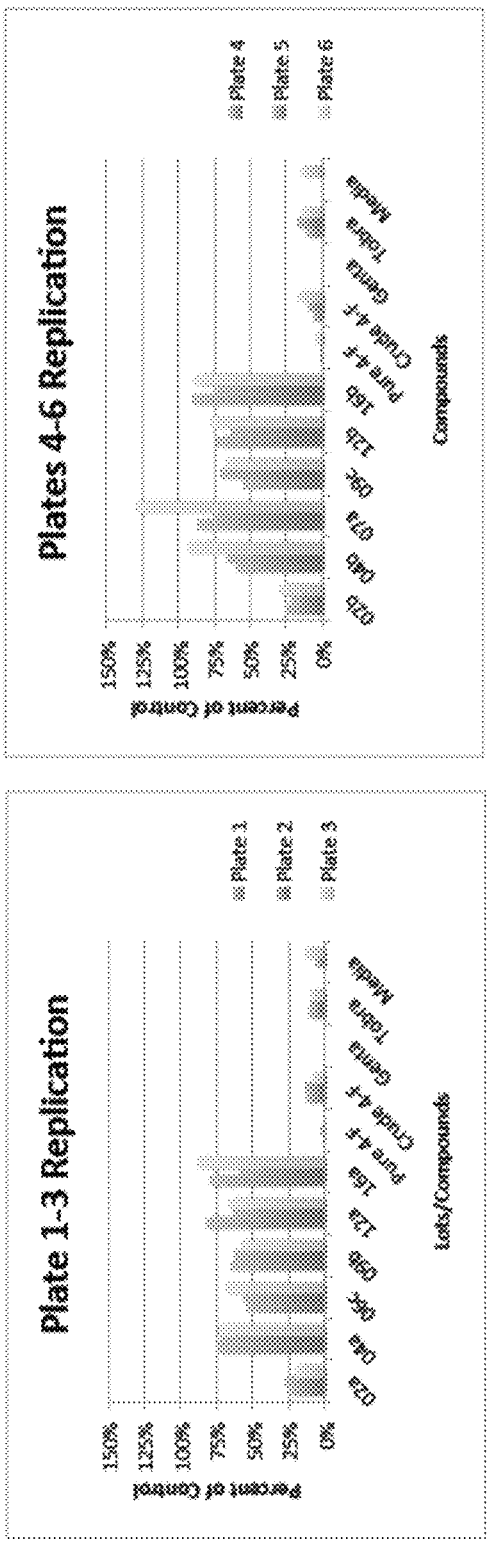
FIG. 17. Graphs illustrating the effects of some compounds on the growth of *P. aeruginosa* with biofilm formation determined in microtiter plates.
Figure 17:
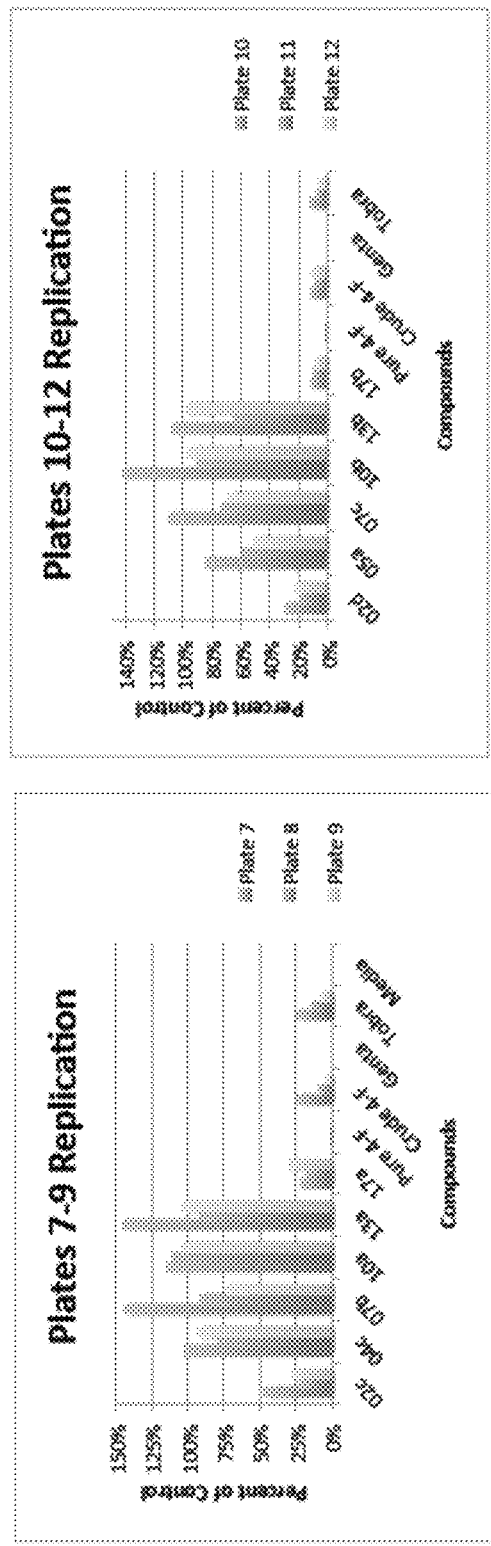
Figure 18:
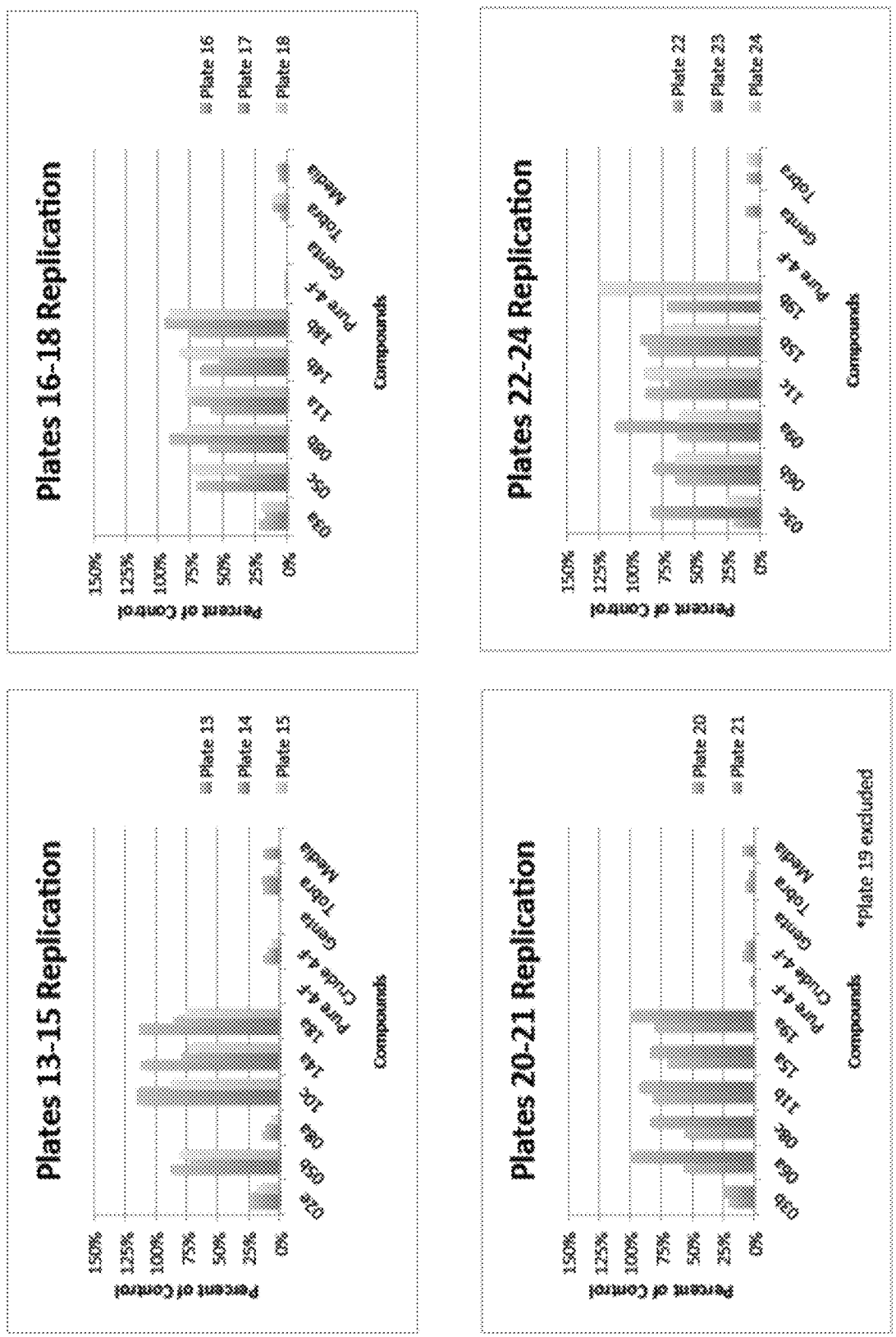
FIG. 18. Graphs illustrating the effects of some compounds on the growth of *P. aeruginosa* with biofilm formation determined in microtiter plates.
Figure 19:
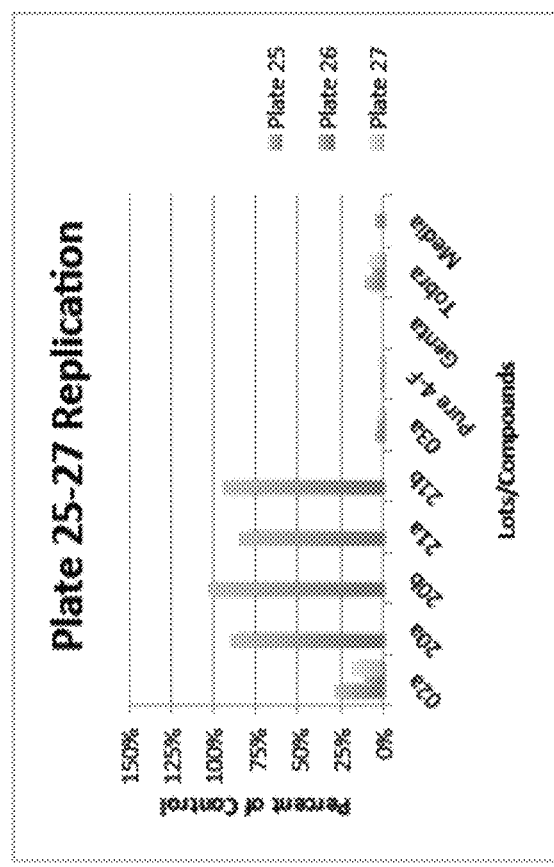
FIG. 19. Graph illustrating the effects of some compounds on the growth of *P. aeruginosa* with biofilm formation determined in microtiter plates.
Figure 20:
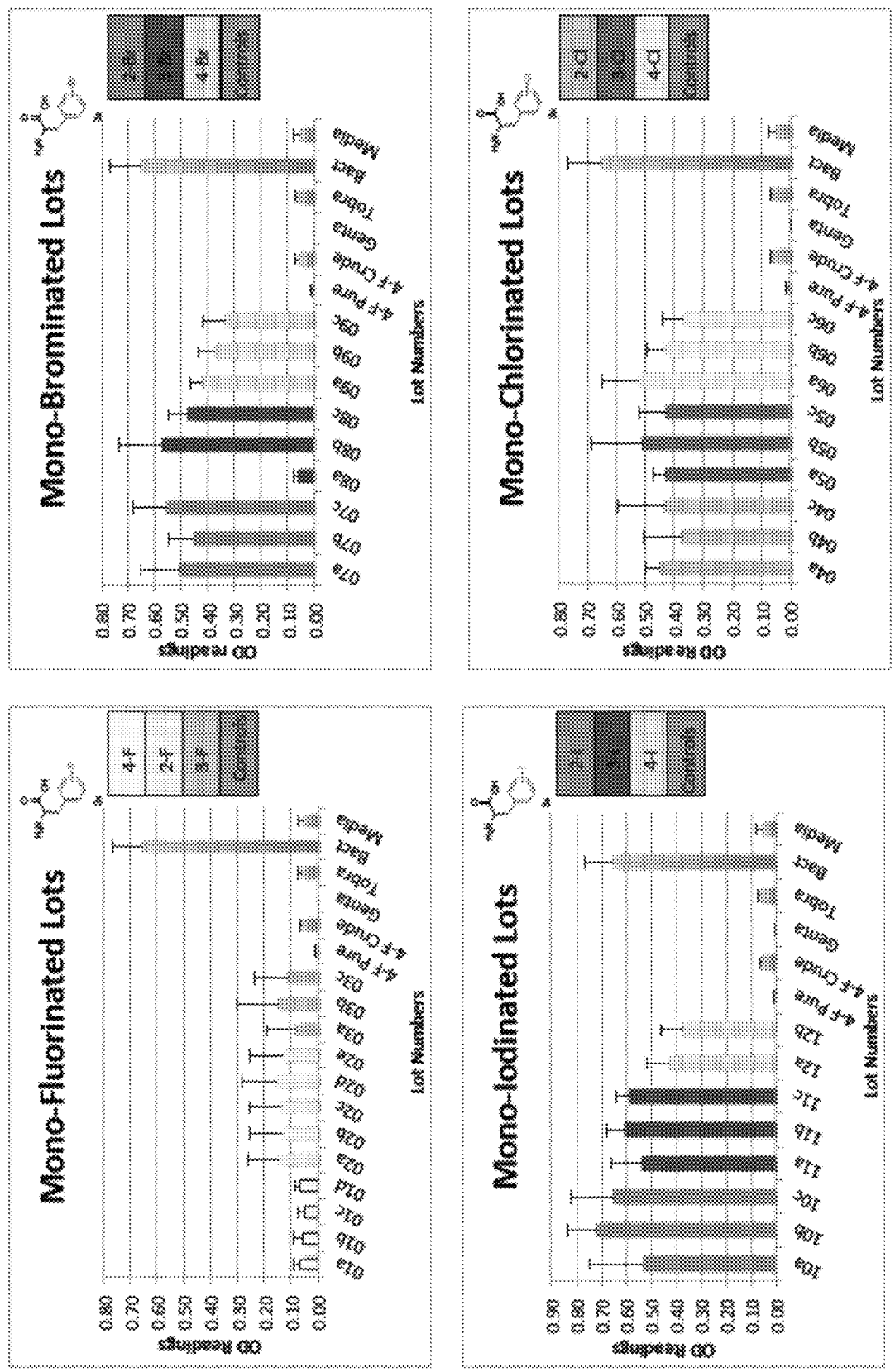
FIG. 20. Graphs illustrating the effects of some mono-fluorinated lots, mono-brominated lots, mono-iodinated lots, and mono-chlorinated lots on the growth of *P. aeruginosa* as indicated by biofilm formation.
Figure 21:
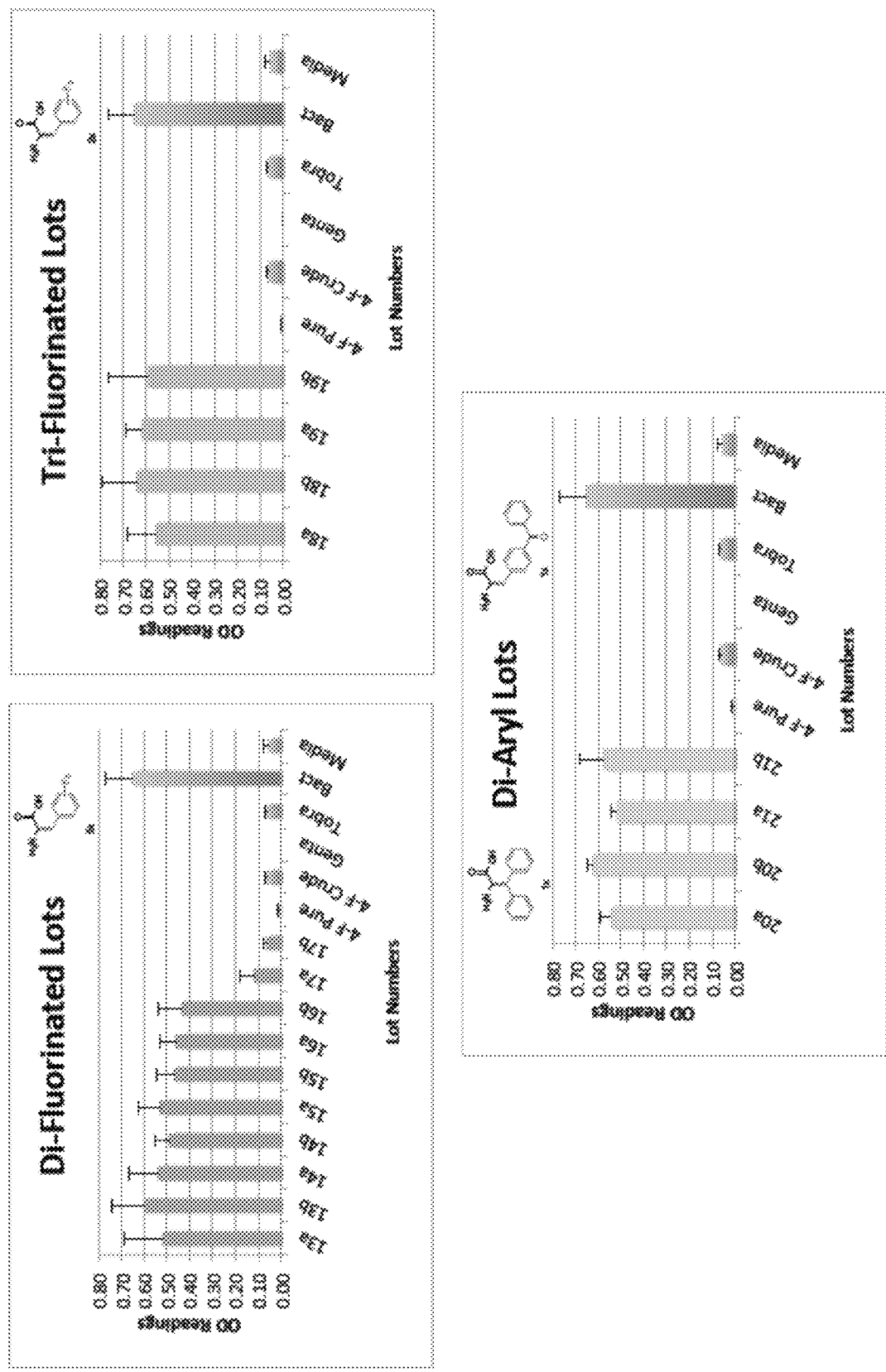
FIG. 21. Graphs illustrating the effects of some di-fluorinated lots, tri-fluorinated lots, di-aryl lots on the growth of *P. aeruginosa* as indicated by biofilm formation.
Figure 22:
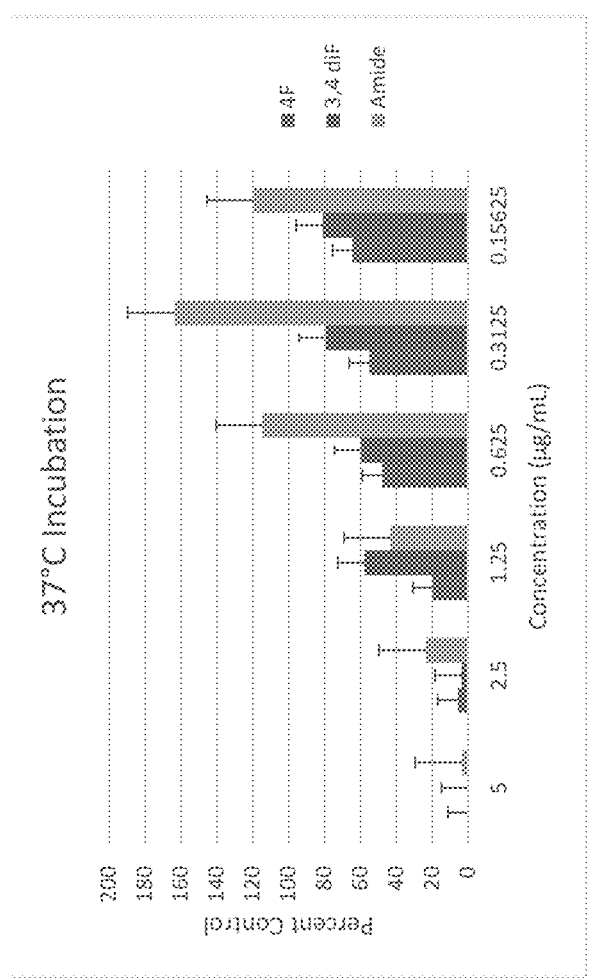
FIG. 22. Graph illustrating the dose dependent effects of 4-fluorophenylalanine (4-F), 3,4-difluorophenylalanine (3,4 diF), and amide on the growth of *P. aeruginosa* as indicated by biofilm formation.

Referring now to FIG. 3, reproducible *P. aeruginosa* Biofilm Assays were carried out using newly synthesized twenty-one "unnatural" amino acids. See George A. O'Toole, Microtiter Dish Biofilm Formation Assay, J. Vis Exp. 2011; (47): 2437, disclosures of which are incorporated by reference in its entirety to the extent that they are not inconsistent with the explicit teachings of this specification.

Figure 23:
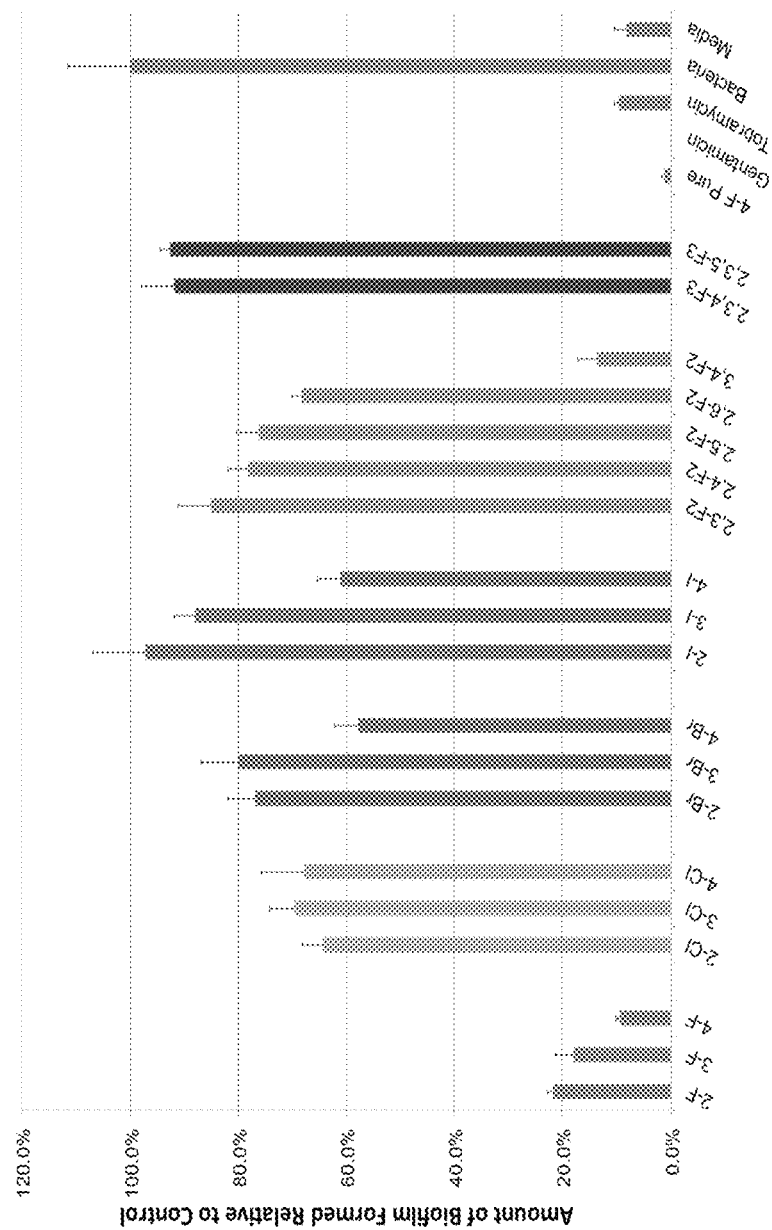
FIG. 23. Graph summarizing the effects of some compounds on the growth of *P. aeruginosa* as indicated by biofilm formation.
Figure 24:
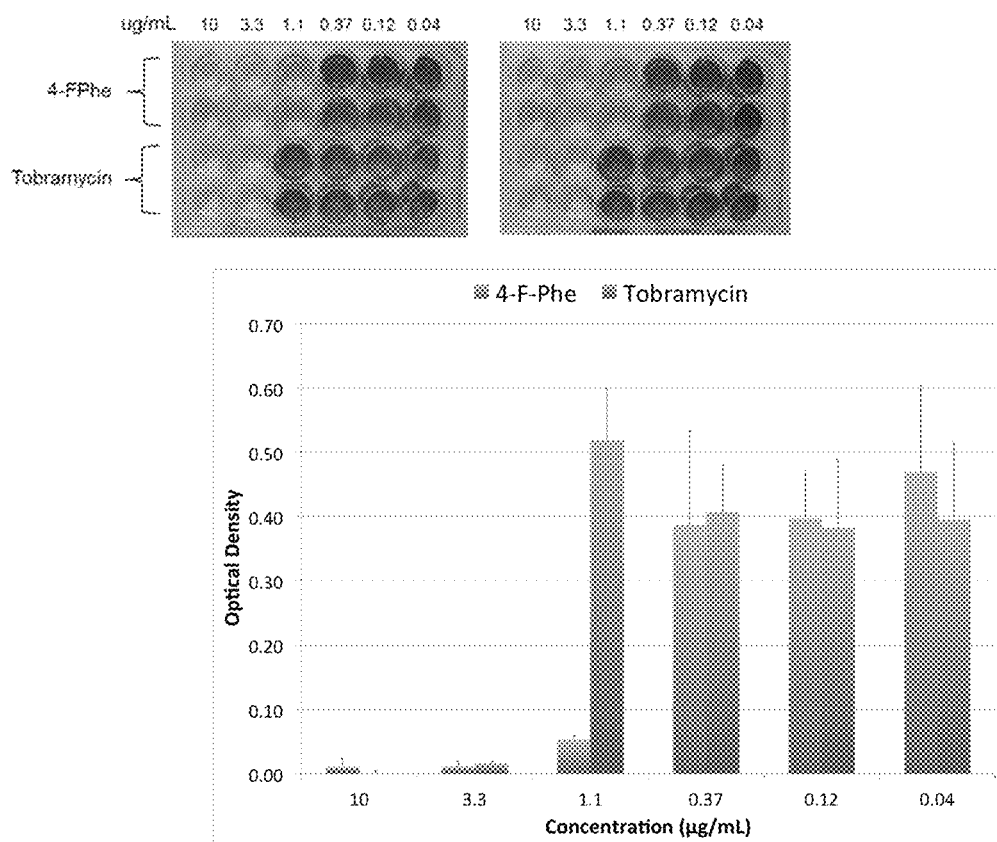
FIG. 24. Photographs of microtiter plates showing the effects of 4-fluorophenylalanine and Tobramycin on the growth of *P. aeruginosa* as indicated by biofilm formation, and a graph illustrating the effects of 4-fluorophenylalanine and Tobramycin on the growth of *P. aeruginosa* as indicated by biofilm formation.
Figure 26:
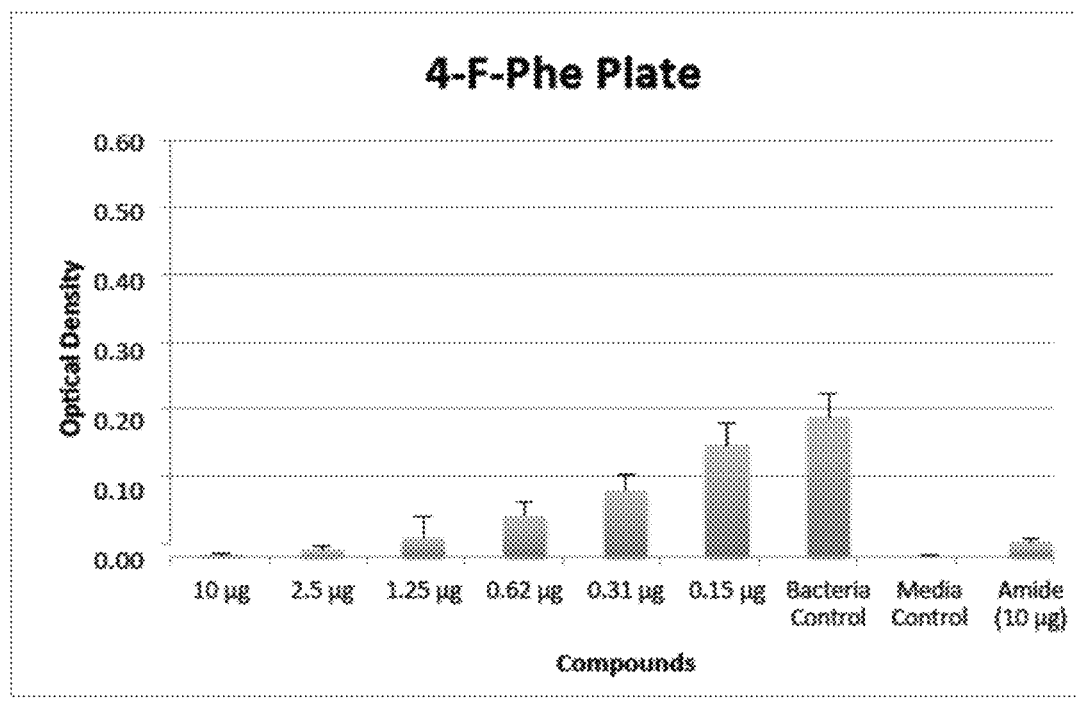
FIG. 26. Graph illustrating the dose dependent effects of 4-fluorophenylalanine (4-F-Phe) and 3-fluorophenylalanine (3-F-Phe) on the growth of *P. aeruginosa* as indicated by biofilm formation.
Figure 26:
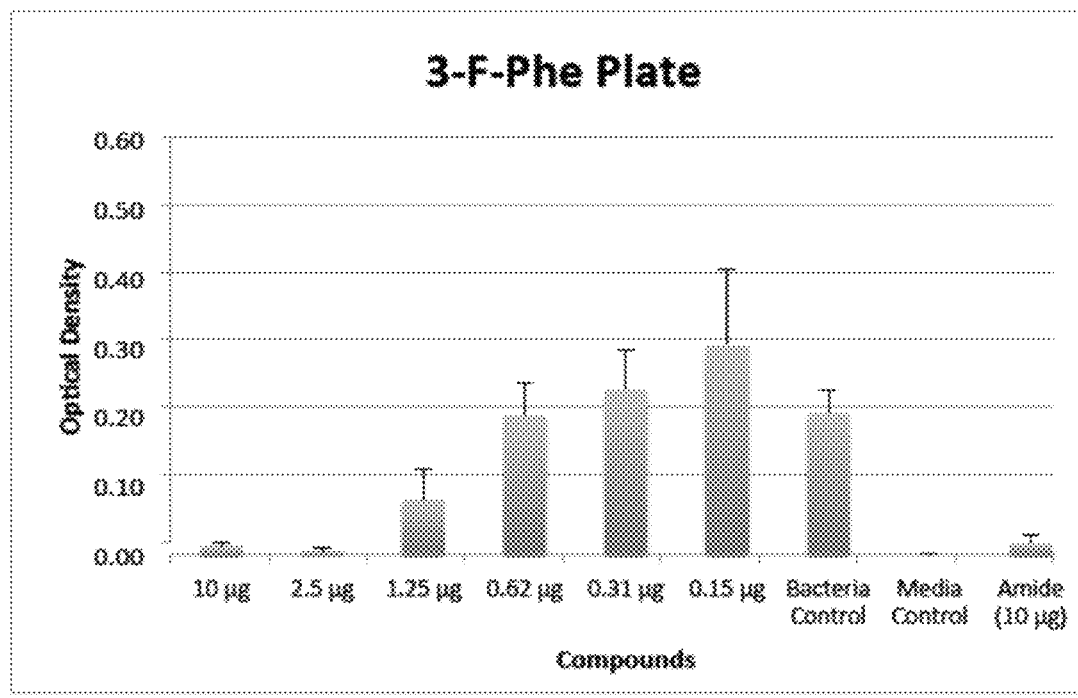
Figure 27:
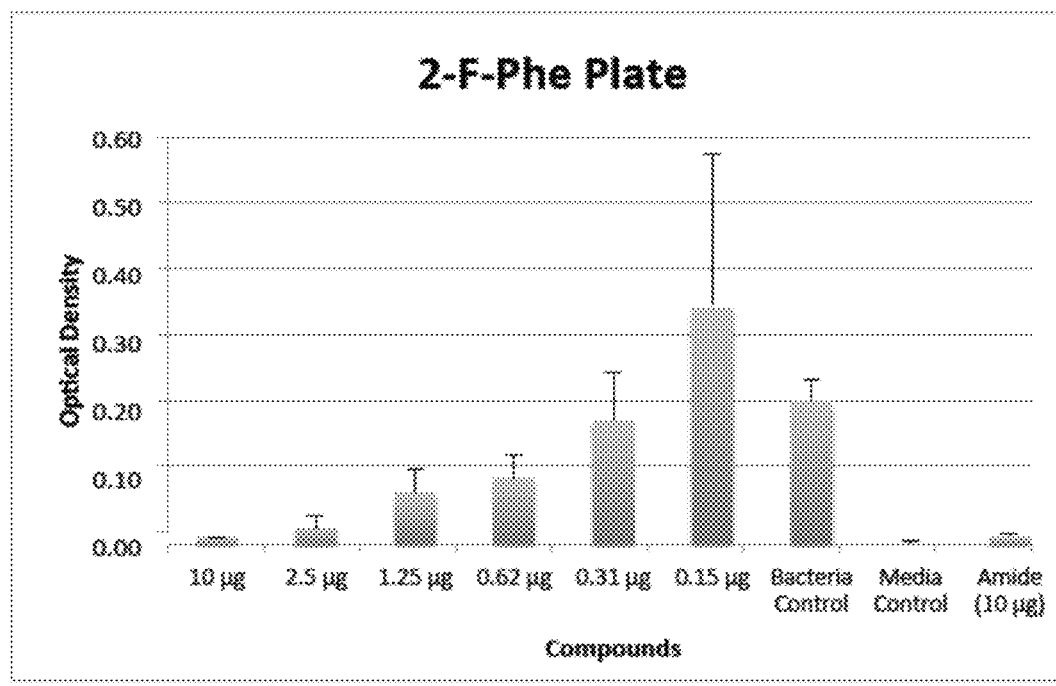
FIG. 27. Graph illustrating the dose dependent effects of 2-fluorophenylalanine (2-F-Phe) and 3,4-difluorophenylalanine (3,4-diF-Phe) on the growth of *P. aeruginosa* as indicated by biofilm formation.
Figure 27:
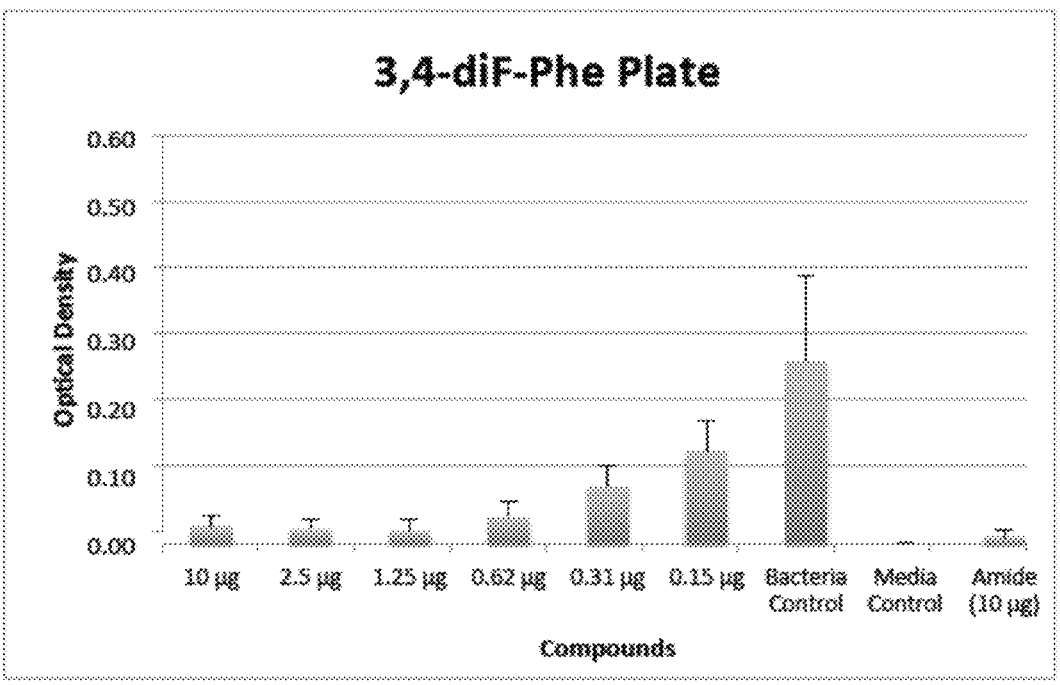
Figure 28:
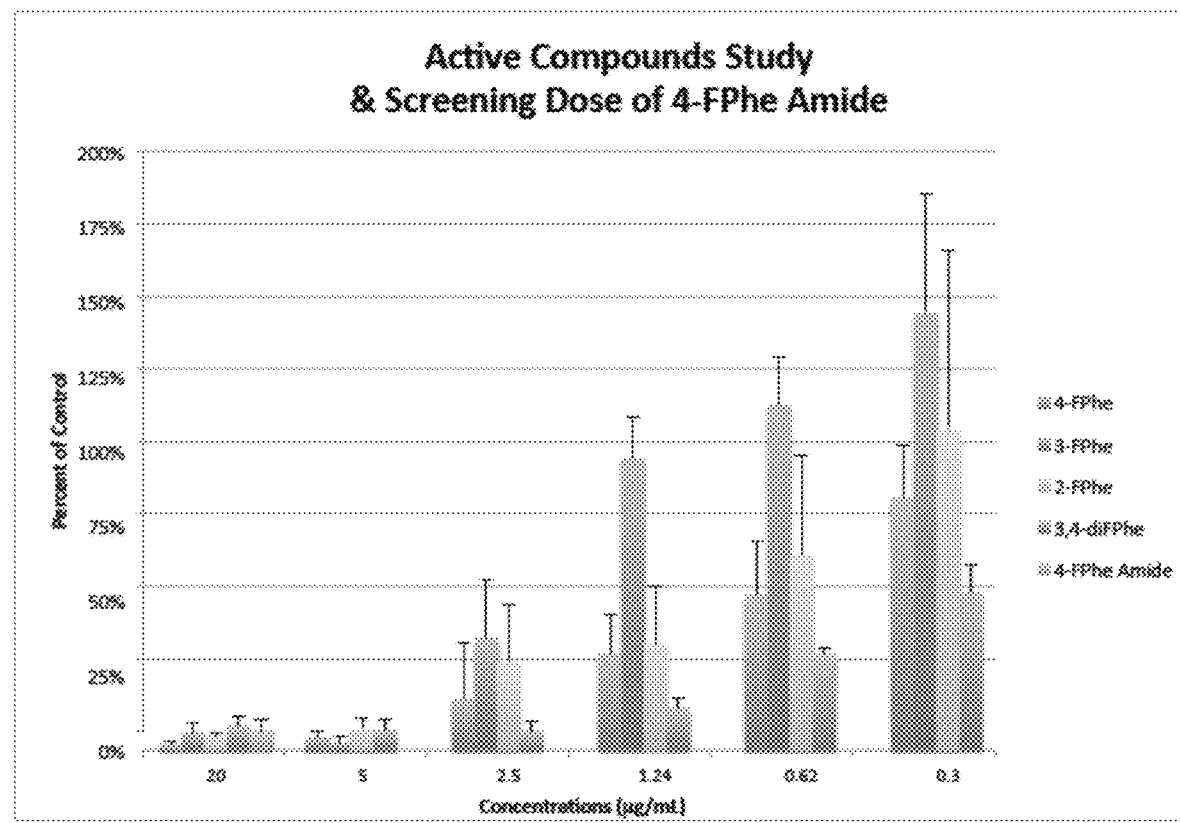
FIG. 28. Graph summarizing the dose dependent effects of 4-fluorophenylalanine (4-F-Phe), 3-fluorophenylalanine (3-F-Phe), 2-fluorophenylalanine (2-F-Phe), 3,4-difluorophenylalanine (3,4-diF-Phe), 4-fluorophenylalanine amide on the growth of *P. aeruginosa* as indicated by biofilm formation.
Figure 29:
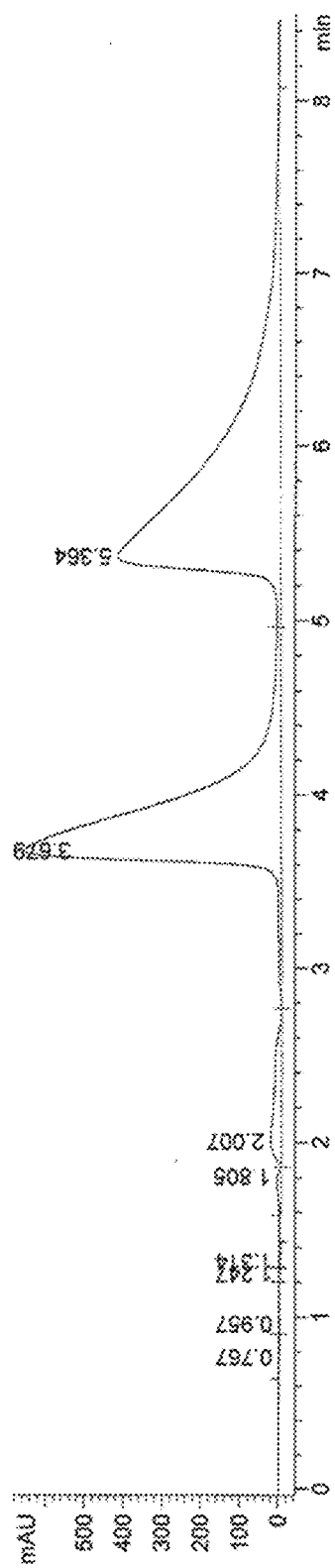
FIG. 29. Graph illustrating separation of D and L forms of racemic 4-fluorophenylalanine (4-F-Phe). Mass of D form of racemic 4-fluorophenylalanine (D-4-F-Phe): 33.1 µg (amount injected: 34.5 µg); Mass of L form of racemic 4-fluorophenylalanine (L-4-F-Phe): 30.4 µg (amount injected: 34.5 µg).
Figure 30:
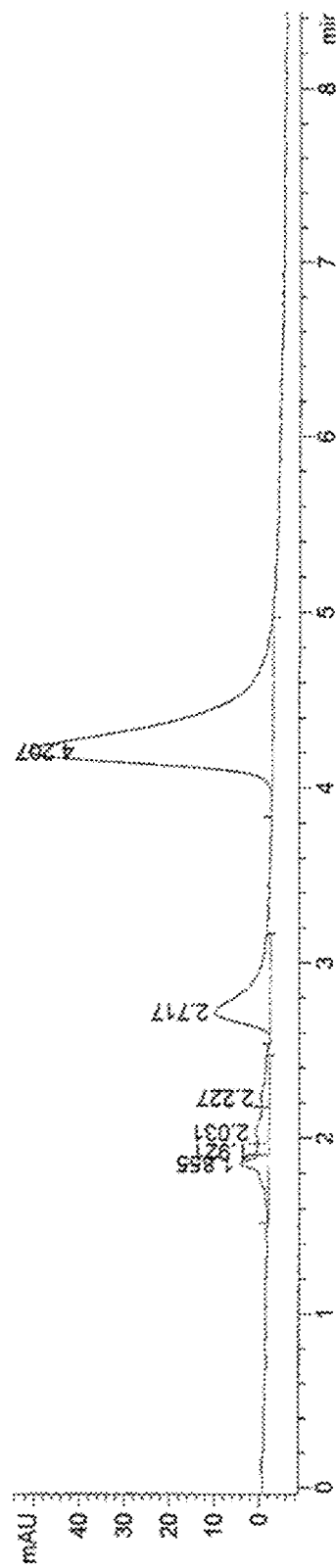
FIG. 30. Graph illustrating an enantiopure D-4-F-Phe.
Figure 31:
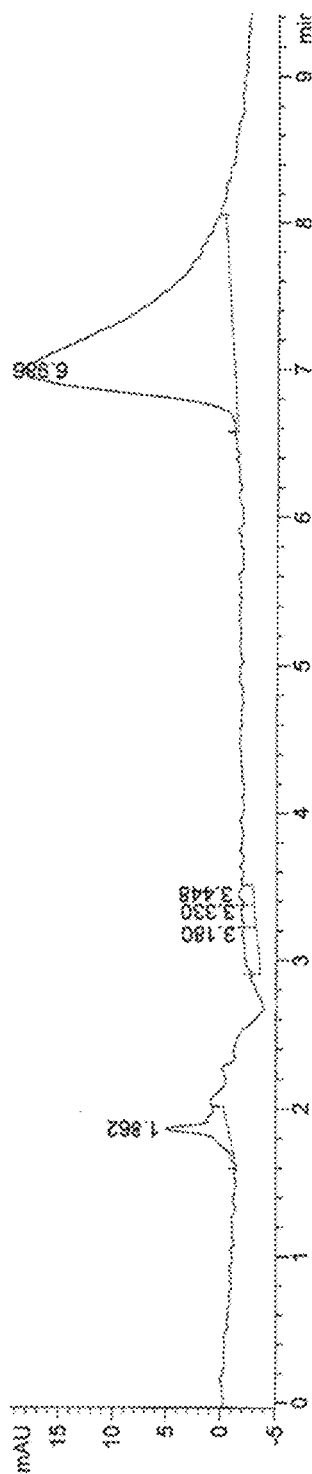
FIG. 31. Graph illustrating an enantiopure L-4-F-Phe.
Figure 32:
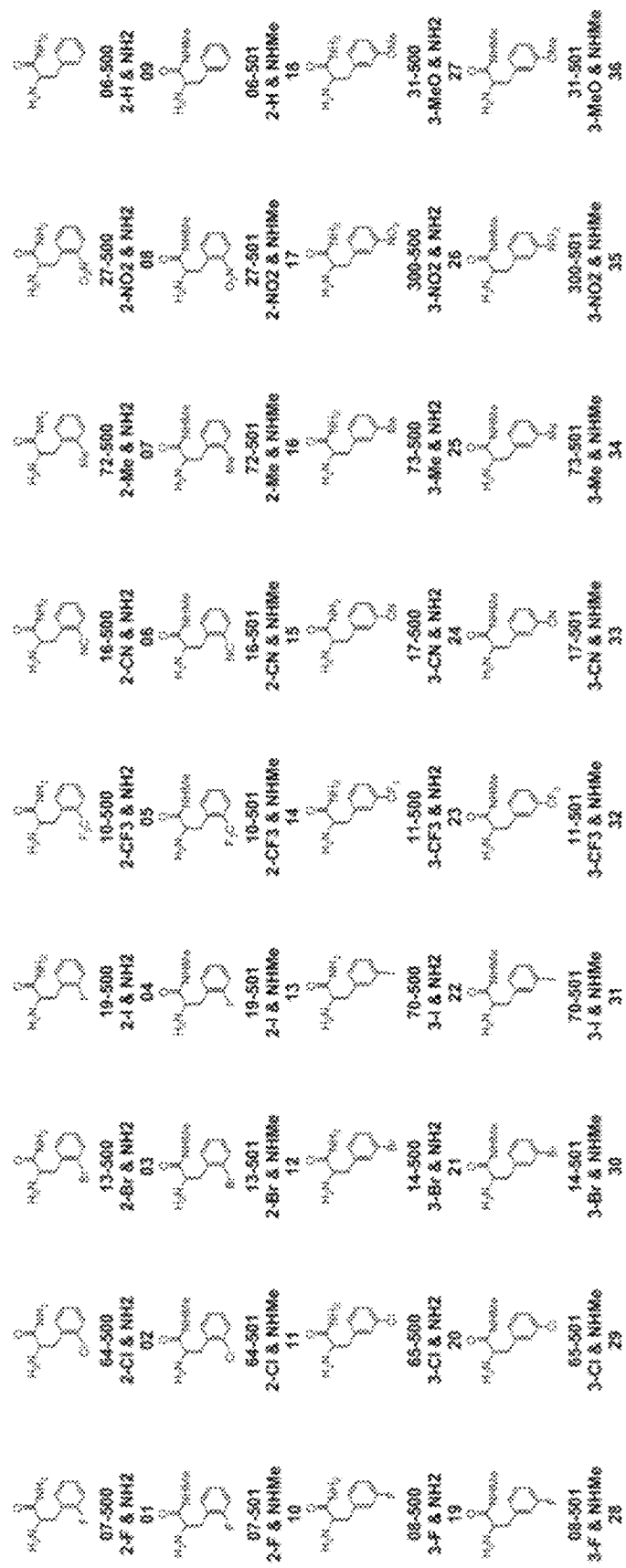
FIG. 32. Exemplary structures of some primary amides and N-methyl amides.
Figure 33:
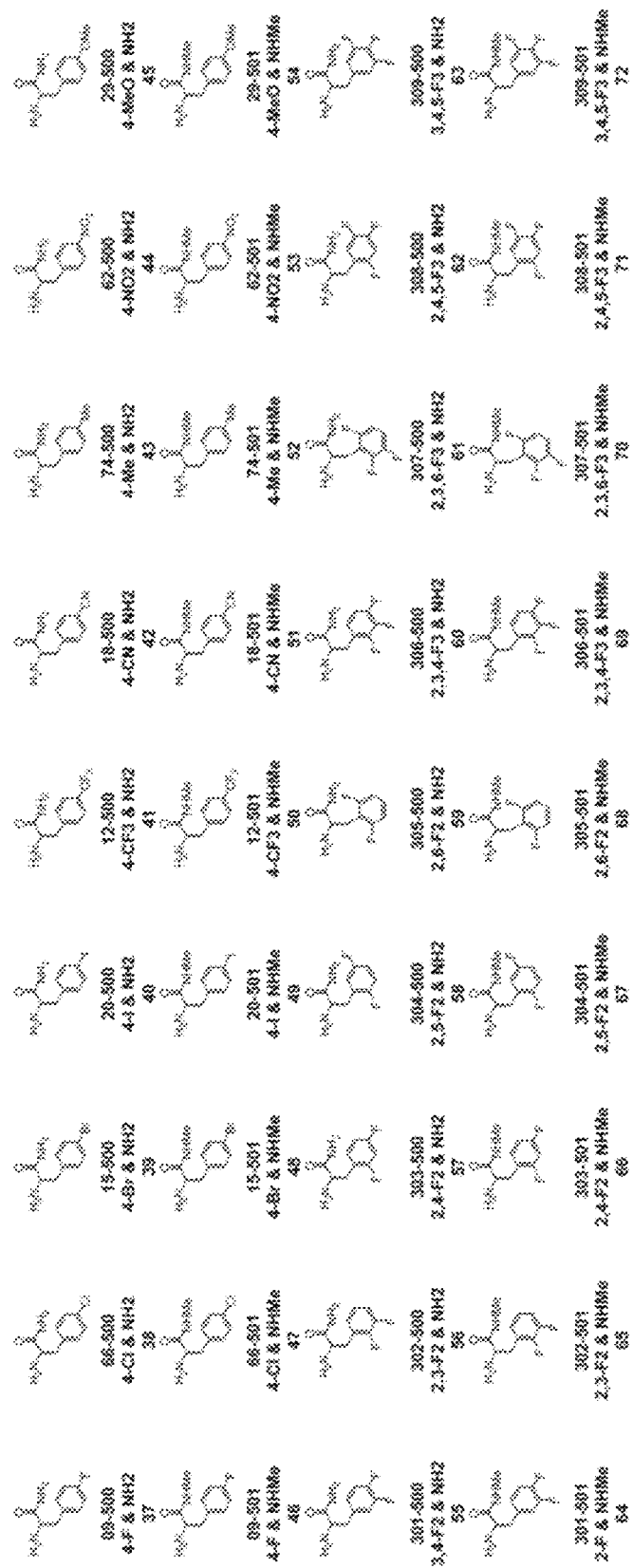
FIG. 33. Exemplary structures of some primary amides and N-methyl amides.

Referring now to FIG. 23, four compounds (2-F, 3-F, 4-F, and 3,4-F2) showed activity in the Biofilm Assay. Subsequent assay of a purified sample of these compounds confirmed this activity, and the compounds were active in a dose dependent manner (FIGS. 26-28). Referring now to FIG. 24, in the biofilm assay 4-F was shown to be as potent as tobramycin (the current treatment for *P. aeruginosa* infections in patients with Cystic Fibrosis).

Exemplary Separation of Enantiomers

Enantiomers were separated by chiral chromatography using a Regis Technologies (Morton Grove, Ill.) Chirosil SCA (−) 4.6×150 mm, 5-micron column using 7/3 MeOH/H$_2$O with 10 mM AcOH at a flow rate of 1.0 mL/min and detection at 214, 230, and 254 nm. A typical injection volume was 30 µL (34.5 µg) of a 1.15 mg/mL solution of purified, racemic compound in 7/3 MeOH/H$_2$O. Each enantiomer was collected manually in separate test tubes. The process was repeated a second time. Combined solutions of individual enantiomers were evaporated to dryness and the residues were dissolved in 200 µL of 7/3 MeOH/H$_2$O. These solutions were then each analyzed on the chiral column (5-4 injections) to verify enantiopurity and then on an Agilent Technologies (Santa Clara, Calif.) Zorbax SB C18, 4.6×150 mm, 5-micron column (30% 1:1 MeOH:MeCN with 5 mM NH$_4$OAc-70% H$_2$O with 5 mM NH$_4$OAc, 1.0 mL/min, 210, 214, 254 nm) to determine mass quantities from peak areas using the calibration equation.

Initially, un-purified samples of two of these compounds, of structures 4-fluorophenylalanine (4-F) and 2-fluorophenylalanine (2-F), were found to be active in the K357 biofilm assay. Subsequent assay of a purified sample of 4-F confirmed this activity. It was then demonstrated that in the biofilm assay 4-F is as potent as tobramycin (the current treatment for *P. aeruginosa* infections in patients with Cystic Fibrosis).

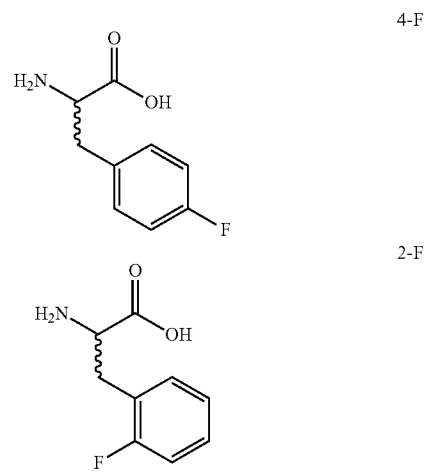

Expanding on these initial results an enantiomeric purification was carried out and the resolved enantiomers were tested in the bioassay. Using these preparations it was established that one of the enantiomers of 4-F is primarily responsible for the direct or indirect potent inhibition of biofilm formation by *P. aeruginosa*. The other enantiomer of 4-F appears to have some activity but at a significantly higher concentration. A Structure Activity Relationship (SAR) was developed to provide a means for improving the utility of these compounds in modulating biofilm formation, and/or inhibiting growth. Critical findings reported in these studies are the potent activity, in addition to 4-F and 2-F, of molecules 3-fluorophenylalanine (3-F) and 3,4-difluorophenylalanine (3,4-F). Also determined using a similar experimental approach is that the amide derivative (4-fluorophenylalanine amide) of 4-F is very potent inhibitor of biofilm development.

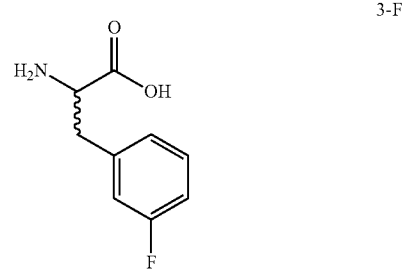

-continued

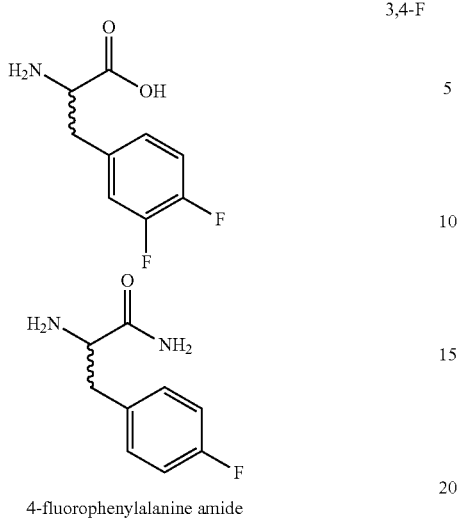

3,4-F 4-fluorophenylalanine amide

Figure 25:
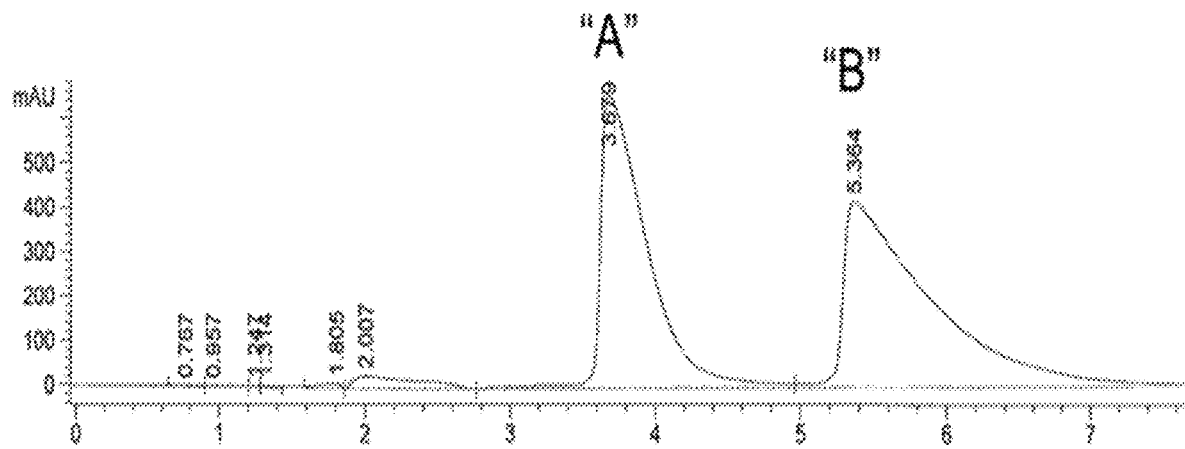
FIG. 25. Graphs illustrating the existence of individual 4-fluorophenylalanine (4-F-Phe) enantiomer and the effects of enantiomer A and B on the growth of *P. aeruginosa* as indicated by biofilm formation.
Figure 25:
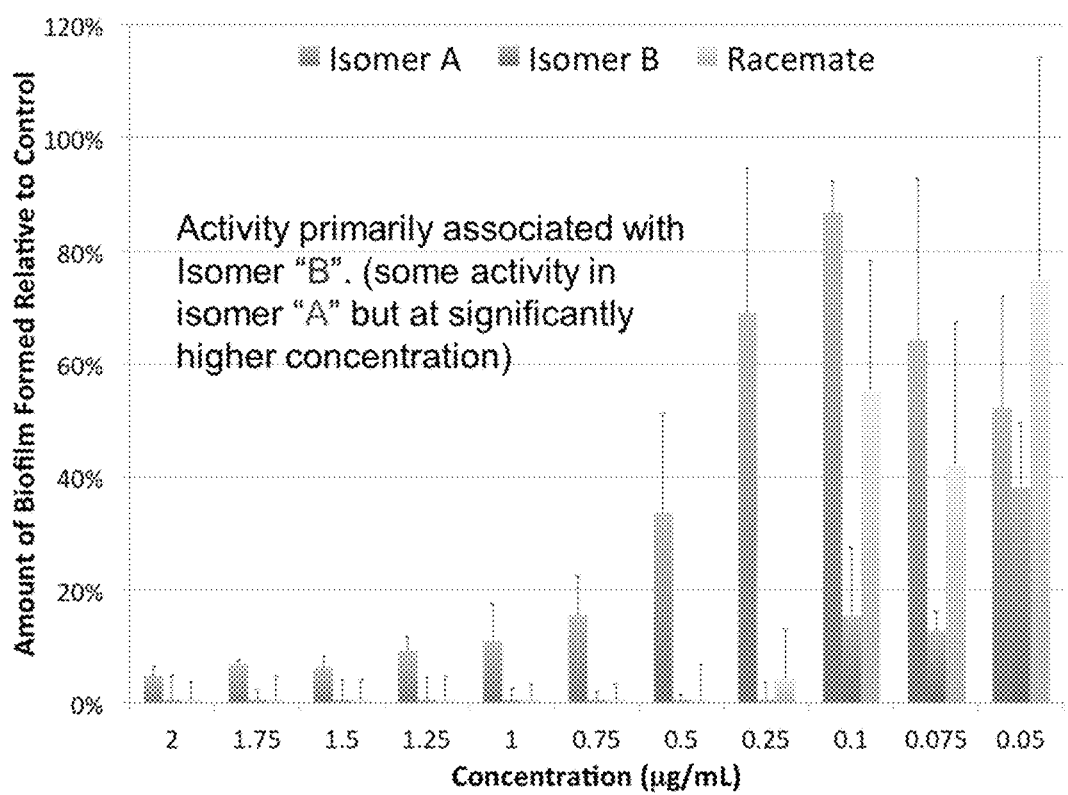

Referring now to FIG. 25, one of the enantiomers ("Isomer B") was found to be primarily responsible for the direct or indirect potent inhibition of biofilm formation by *P. aeruginosa*. The other enantiomer ("Isomer A") appears to have some activity but at a significantly higher concentration.

Figure 34:
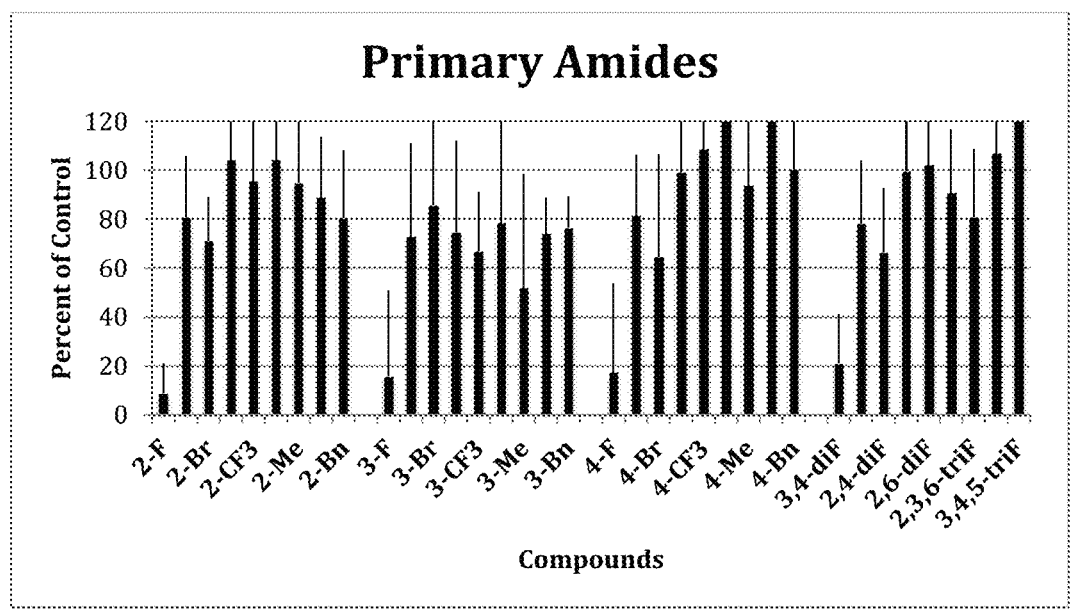
FIG. 34. Graph summarizing the effects of 2-, 3-, 4-, and 3,4-substituted phenylalanine primary amides on the growth of *P. aeruginosa* as indicated by biofilm formation. Results were expressed as % biofilm formation (control=bacteria alone=100% biofilm formation).
Figure 35:
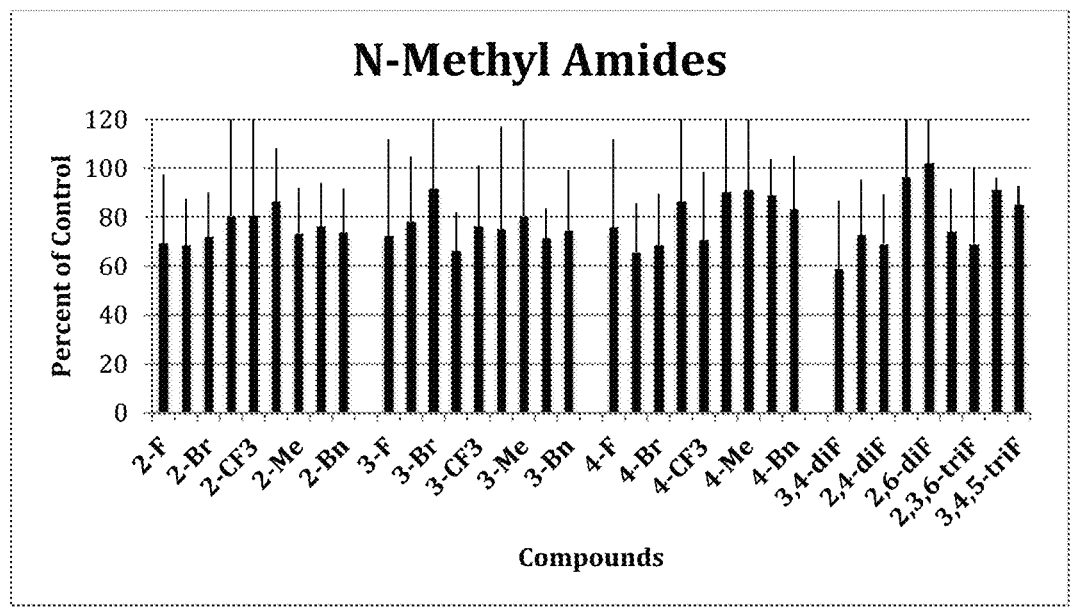
FIG. 35. Graph summarizing the effects of some 2-, 3-, 4-, and 3,4-substituted phenylalanine N-methyl amides on the growth of *P. aeruginosa* as indicated by biofilm formation. Results were expressed as % biofilm formation (control=bacteria alone=100% biofilm formation).

Referring now to FIGS. 34-35, newly synthesized compounds were prepared according to the schemes described above. These compounds include, but not limited to, compounds having the formula:

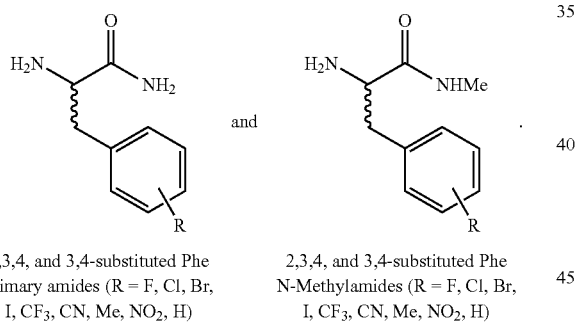

2,3,4, and 3,4-substituted Phe primary amides (R = F, Cl, Br, I, CF$_3$, CN, Me, NO$_2$, H)   and   2,3,4, and 3,4-substituted Phe N-Methylamides (R = F, Cl, Br, I, CF$_3$, CN, Me, NO$_2$, H)

Referring to FIGS. 34-35, all newly synthesized compounds prepared according to the schemes described above were assayed for biofilm formation in multiplicate 24 well plates at a screening dose of 20 μg/mL using crystal violet optical density (OD) readings as the readout. Results were expressed as % biofilm formation relative to a control (control=bacteria alone=100% biofilm formation). The procedure for the biofilm assay was the same as that used by students in the K357 biofilm laboratory.

Figure 36:
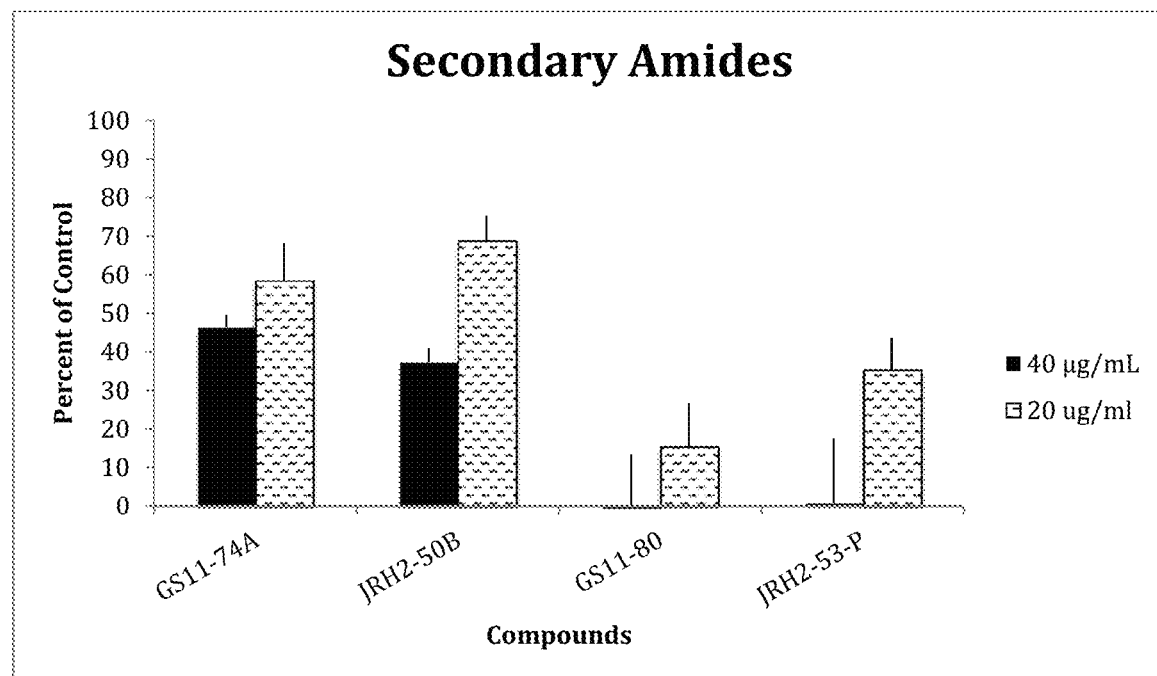
FIG. 36. Graph summarizing the dose dependent effects of some secondary amides on the growth of *P. aeruginosa* as indicated by biofilm formation. Results are expressed as biofilm formation (control=bacteria alone=100% biofilm formation).
Figure 37:
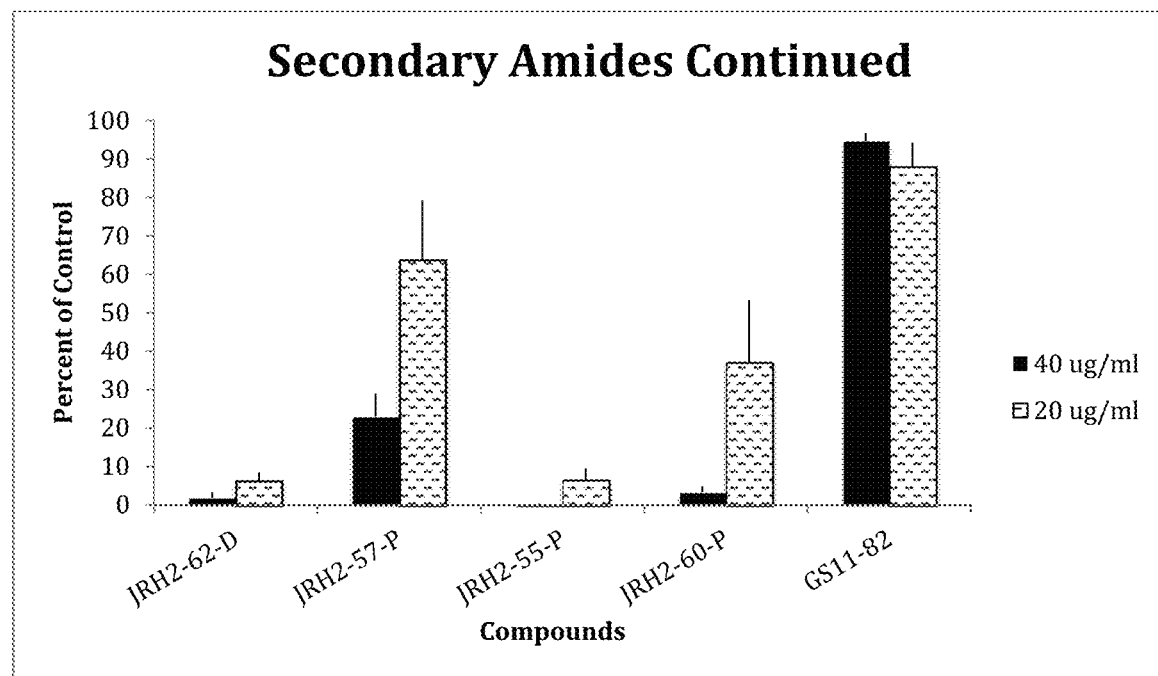
FIG. 37. Graph summarizing the dose dependent effects of some secondary amides on the growth of *P. aeruginosa* as indicated by biofilm formation. Results were expressed as % biofilm formation (control=bacteria alone=100% biofilm formation).
Figure 38:
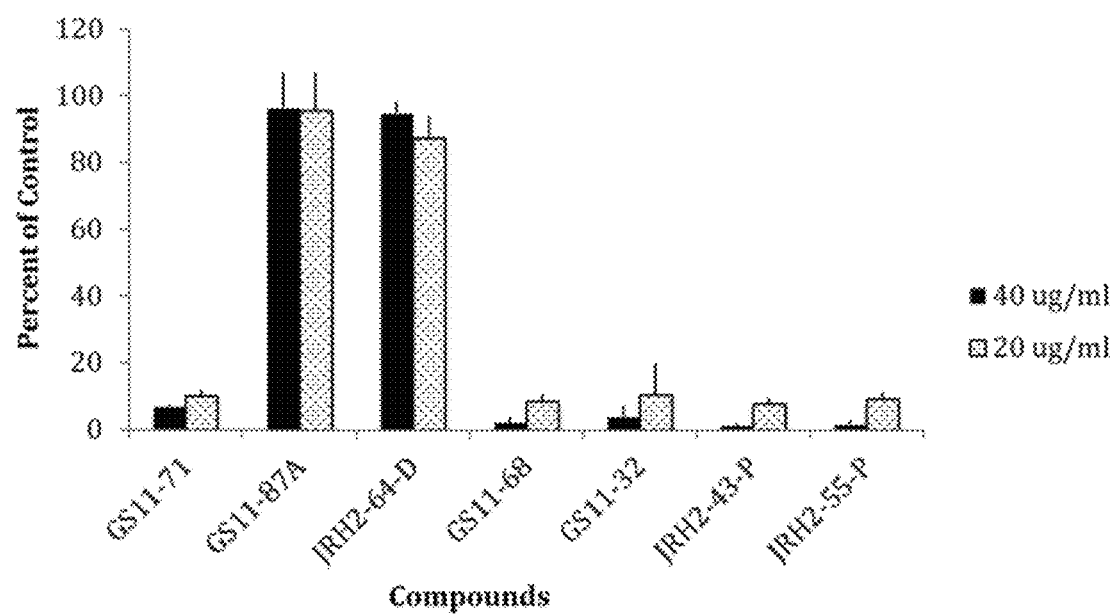
FIG. 38. Graph summarizing the dose dependent effects of some secondary and tertiary amides on the growth of *P. aeruginosa* as indicated by biofilm formation. Results were expressed as % biofilm formation (control=bacteria alone=100% biofilm formation).

Referring now to FIGS. 36-38, all compounds assayed in either 96 well or 24 well plates at a screening dose of either 20 or 40 μg/mL, using a biofilm assay with crystal violet optical density (OD) readings as the readout. Results were expressed as % biofilm formation (control=bacteria alone=100% biofilm formation). The procedure for the biofilm assay was the same as that used by students in the K357 biofilm laboratory.

Newly synthesized compounds used in FIGS. 36-38 include:

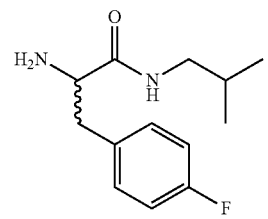

GS11-74A

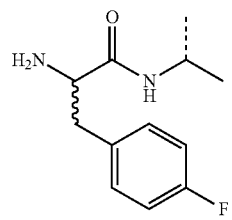

JRH2-50B

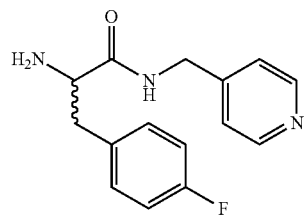

GS11-80

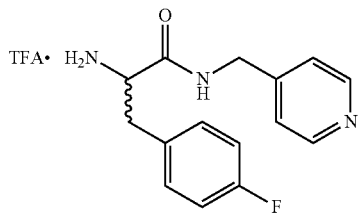

JRH2-53-P

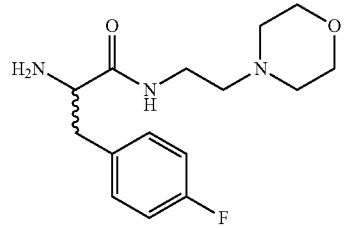

JRH2-62-D

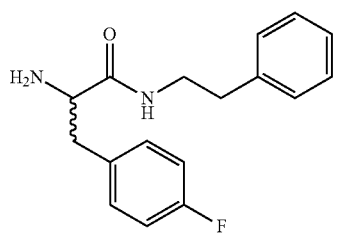

JRH2-57-P

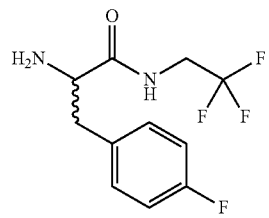

J2H2-55-P

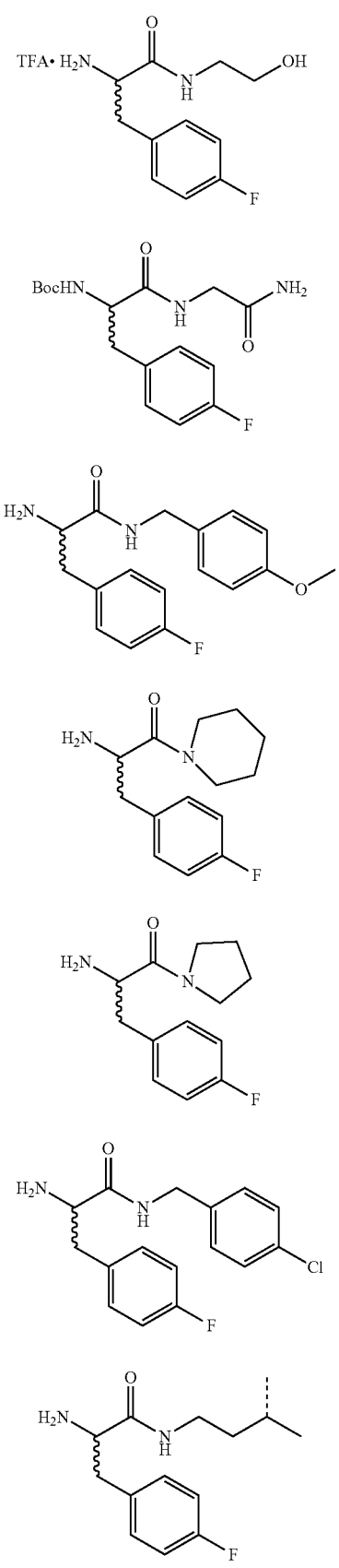
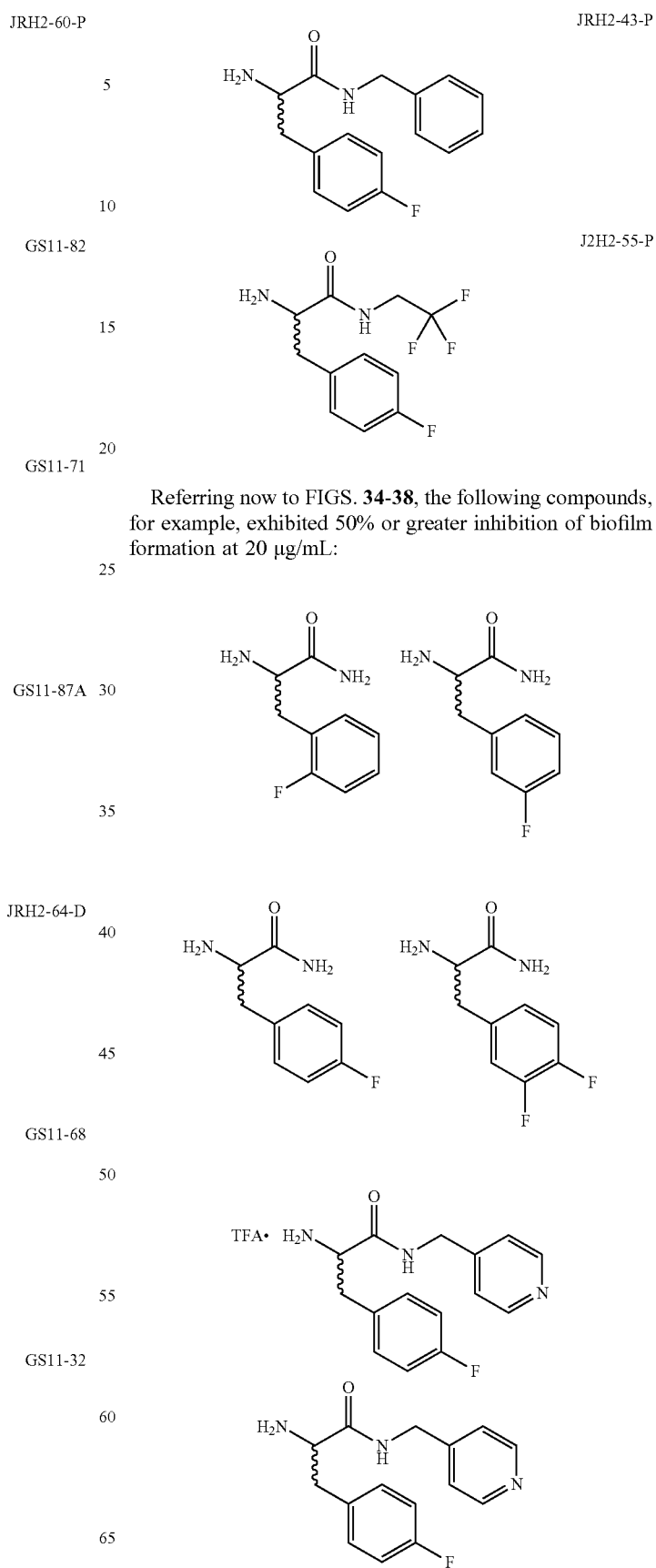
Referring now to FIGS. 34-38, the following compounds, for example, exhibited 50% or greater inhibition of biofilm formation at 20 μg/mL:

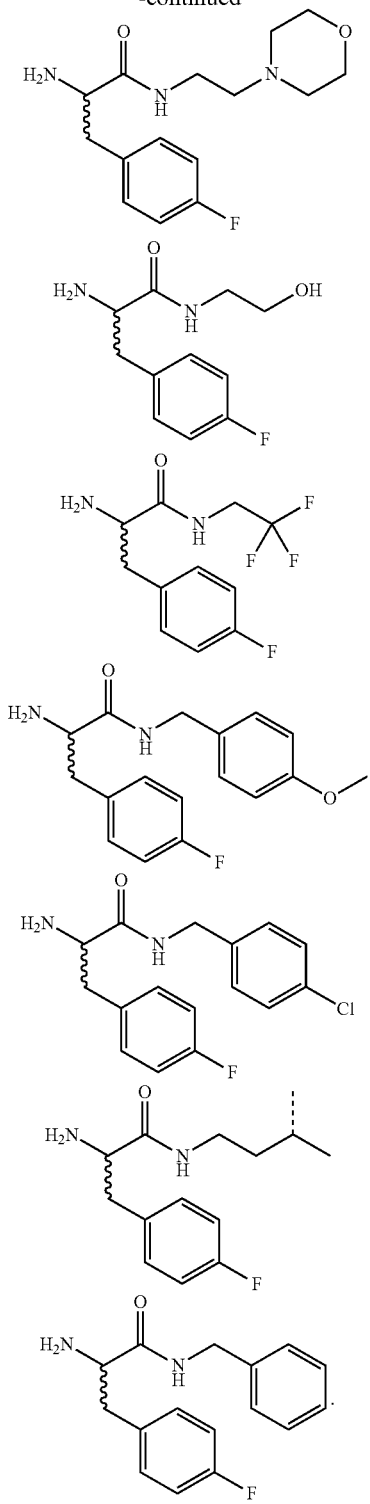

examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method for reducing the growth of bacteria, comprising the steps of:
    treating bacteria with at least one compound of the formula:

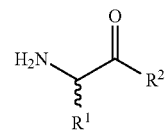

wherein:
  $R^1$ is selected from the group consisting of: benzyl substituted with 1 to 3 halogens, $C_1$-$C_6$ alkyl, $C_1$-$C_6$ alkoxy, —$NH_2$, —$NO_2$, —CN, or —$CF_3$, and phenyl substituted with 1 to 3 halogens, $C_1$-$C_6$ alkyl, $C_1$-$C_6$ alkoxy, —$NH_2$, —$NO_2$, —CN, or —$CF_3$;
  $R^2$ is $NR^3R^4$;
  $R^3$ is H;
  $R^4$ is —$(CH_2)_n$—$R^5$;
  $R^5$ is methyl, —OH, —$CF_3$, morpholinyl, pyridinyl, or phenyl substituted with 1 to 3 halogen, $C_1$-$C_6$ alkyl, $C_1$-$C_6$ alkoxy, —OH, —$NH_2$, —$NO_2$, —CN, or —$CF_3$; and
  n is 1, 2, 3, or 4;
  or a pharmaceutically acceptable salt thereof.

2. The method according to claim 1, wherein the at least one compound is selected from the group consisting of:

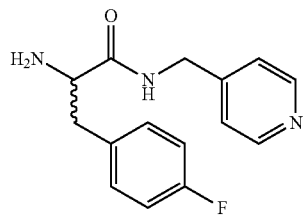

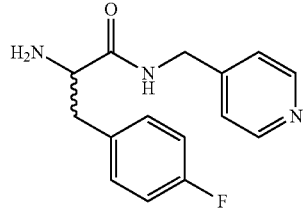

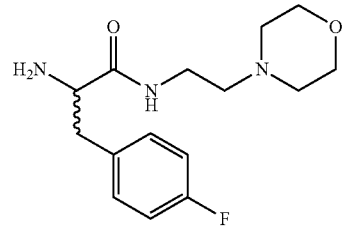

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific -continued

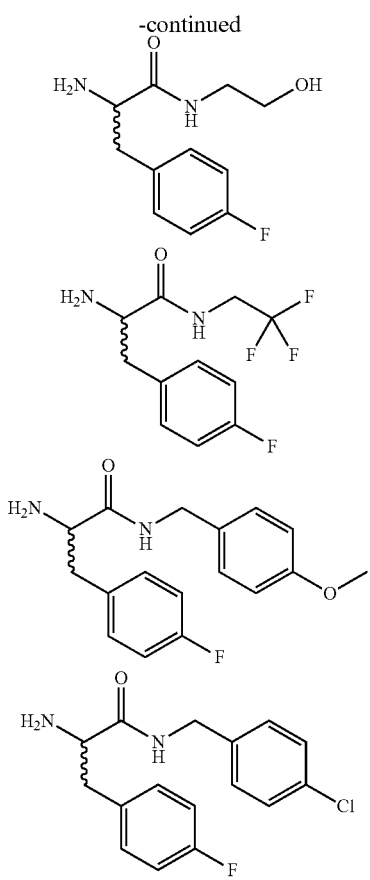

or a pharmaceutically acceptable salt thereof.

3. The method according to claim 1, wherein the bacteria is gram-negative bacteria.

4. The method according to claim 1, wherein the bacteria is *Pseudomonas aeruginosa*.

5. The method according to claim 1, further comprising the step of:

reducing biofilm formation of the bacteria.

6. The method according to claim 1, further comprising the step of:

treating an area that has been infected by the bacteria.

7. The method according to claim 6, wherein the area comprises surfaces or hair of an animal, a human, or a plant.

8. A method of treating bacterial infections, comprising the steps of:

administering to a patient at least one therapeutically effective dose of at least one compound of the formula:

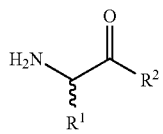

wherein:

R$^1$ is selected from the group consisting of: benzyl substituted with 1 to 3 halogens, C$_1$-C$_6$ alkyl, C$_1$-C$_6$ alkoxy, —NH$_2$, —NO$_2$, —CN, or —CF$_3$, and phenyl substituted with 1 to 3 halogens, C$_1$-C$_6$ alkyl, C$_1$-C$_6$ alkoxy, —NH$_2$, —NO$_2$, —CN, or —CF$_3$;

R$^2$ is NR$^3$R$^4$;

R$^3$ is H;

R$^4$ is —(CH$_2$)$_n$—R$^5$;

R$^5$ is methyl, —OH, —CF$_3$, morpholinyl, pyridinyl, or phenyl substituted with 1 to 3 halogen, C$_1$-C$_6$ alkyl, C$_1$-C$_6$ alkoxy, —OH, —NH$_2$, —NO$_2$, —CN, or —CF$_3$; and n is 1, 2, 3, or 4;

or a pharmaceutically acceptable salt thereof.

9. The method according to claim 8, further comprising the step of:

diagnosing a patient with bacterial infections, wherein the bacterial infections are caused by gram-negative bacteria.

10. The method according to claim 9, wherein the gram-negative bacteria is *Pseudomonas aeruginosa*.

11. The method according to claim 8, wherein the at least one compound is selected from the group consisting of:

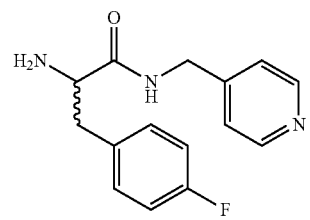

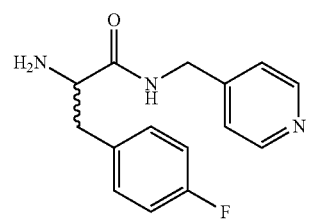

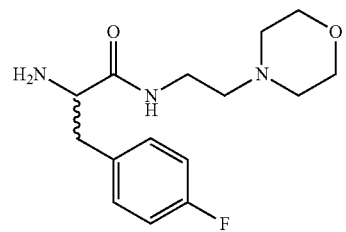

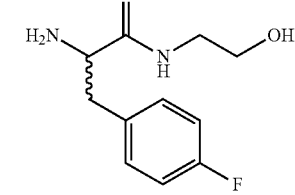

-continued

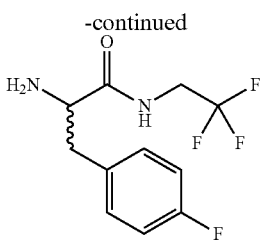

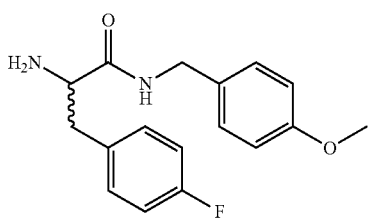

-continued

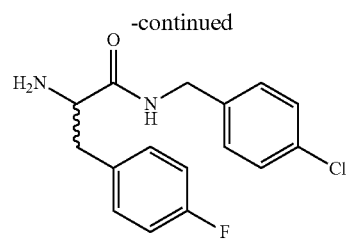

or a pharmaceutically acceptable salt thereof.

12. The method according to claim 8, wherein the therapeutically effective dose of the at least one compound is on the order of between about 1 mg/kg to about 7 mg/kg and the dose of the compound is administered to the patient at least once per day.

13. The method according to claim 12, wherein the therapeutically effective dose of the at least one compound is on the order of between about 3 mg/kg to about 5 mg/kg and the dose of the compound is administered to the patient at least once per day.

14. The method according to claim 8, wherein the therapeutically effective dose of the at least one compound is administered by intravenous or intramuscular injections.

* * * * *